(12) United States Patent
Hung et al.

(10) Patent No.: US 10,519,494 B2
(45) Date of Patent: Dec. 31, 2019

(54) METHODS AND SYSTEMS FOR NUCLEIC ACID ANALYSIS AND QUANTIFICATION

(71) Applicant: Combinati Incorporated, Palo Alto, CA (US)

(72) Inventors: Ju-Sung Hung, Palo Alto, CA (US); Megan Dueck, Brisbane, CA (US); Andrew Zayac, San Leandro, CA (US)

(73) Assignee: COMBINATI INCORPORATED, Palo Alto, CA (US)

( * ) Notice: Subject to any disclaimer, the term of this patent is extended or adjusted under 35 U.S.C. 154(b) by 0 days.

(21) Appl. No.: 16/408,041

(22) Filed: May 9, 2019

(65) Prior Publication Data

US 2019/0264260 A1  Aug. 29, 2019

Related U.S. Application Data

(63) Continuation of application No. PCT/US2017/062078, filed on Nov. 16, 2017.

(60) Provisional application No. 62/423,601, filed on Nov. 17, 2016.

(51) Int. Cl.
*B01L 3/00* (2006.01)
*C12Q 1/686* (2018.01)

(52) U.S. Cl.
CPC ........ *C12Q 1/686* (2013.01); *B01L 3/502715* (2013.01); *B01L 2200/0684* (2013.01); *B01L 2200/16* (2013.01); *B01L 2300/0816* (2013.01); *B01L 2300/0864* (2013.01)

(58) Field of Classification Search
None
See application file for complete search history.

(56) References Cited

U.S. PATENT DOCUMENTS

| | | | |
|---|---|---|---|
| 5,807,522 A | 9/1998 | Brown et al. | |
| 8,871,446 B2 | 10/2014 | Hong et al. | |
| 9,213,042 B2 | 12/2015 | Oldham et al. | |
| 9,845,499 B2 | 12/2017 | Hung et al. | |

(Continued)

FOREIGN PATENT DOCUMENTS

| | | |
|---|---|---|
| WO | WO-2015085181 A1 | 6/2015 |
| WO | WO-2017176699 A1 | 10/2017 |
| WO | WO-2018094091 A1 | 5/2018 |

OTHER PUBLICATIONS

Karlsson et al., Active liquid degassing in microfluidic systems, Lab Chip, 2013, 13, 4366-4373, Aug. 21, 2013.*

(Continued)

*Primary Examiner* — Aaron A Priest
(74) *Attorney, Agent, or Firm* — Wilson Sonsini Goodrich & Rosati

(57) ABSTRACT

The present disclose provides methods and systems for amplifying and quantifying nucleic acids and for detecting the presence or absence of a target in a sample. The methods and systems provided herein may utilize a device comprising a plurality of partitions separated from an external environment by a gas-permeable barrier. Certain methods disclosed herein involve subjecting nucleic acid molecules in the plurality of partitions to conditions sufficient to conduct nucleic acid amplification reactions. The nucleic acid molecules may be subjected to controlled heating in the plurality of partitions to generate data indicative of a melting point(s) of the nucleic acid molecules.

21 Claims, 27 Drawing Sheets

Specification includes a Sequence Listing.

(56) References Cited

U.S. PATENT DOCUMENTS

| | | | |
|---|---|---|---|
| 10,252,266 | B2 | 4/2019 | Hung et al. |
| 2009/0250347 | A1 | 10/2009 | Powell et al. |
| 2011/0003699 | A1 | 1/2011 | Yoder et al. |
| 2012/0107818 | A1 | 5/2012 | Rothmann et al. |
| 2013/0130232 | A1* | 5/2013 | Weibel ............. G01N 33/54386 435/5 |
| 2014/0291558 | A1 | 10/2014 | Laermer et al. |
| 2014/0323358 | A1 | 10/2014 | Oldham et al. |
| 2016/0025761 | A1 | 1/2016 | West et al. |
| 2016/0214112 | A1* | 7/2016 | Saito ...................... C12Q 1/686 |
| 2016/0228874 | A1* | 8/2016 | Lee ...................... C12Q 1/6851 |
| 2016/0318023 | A1 | 11/2016 | Marble et al. |
| 2017/0096705 | A1* | 4/2017 | Stern ................. B01L 3/502738 |
| 2018/0078935 | A1 | 3/2018 | Hung et al. |

OTHER PUBLICATIONS

Lochovsky et al., Bubbles no more: in-plane trapping and removal of bubbles in microfluidic devices, Lab Chip. Feb. 7, 2012;12(3): 595-601. doi: 10.1039/c1lc20817a. Epub Dec. 13, 2011.*
Xu et al., Use of a porous membrane for gas bubble removal in microfluidic channels: physical mechanisms and design criteria, Microfluidics and Nanofluidics, Oct. 2010, vol. 9, Issue 4-5, pp. 765-772.*
Zhu, Micro/nanoporous membrane based gas-water separation in microchannel, Journal Microsystem Technologies archive, vol. 15 Issue 9, Sep. 2009, pp. 1459-1465.*
Beer et al. On-Chip, Real-Time, Single-Copy Polymerase Chain Reaction in Picoliter Droplets. Anal Chem 79:8471-8475 (2007).
Co-pending U.S. Appl. No. 16/270,457, filed Feb. 7, 2019.
Espira, Inc. Digital PCR. http://www.espirainc.com/digital-per.html (1 pg.) (Feb. 15, 2017).
Formulatrix. Constellation Digital PCR. http://formulatrix.com/per/index.html (3 pgs.) (Feb. 15, 2017).
JN Medsys, Clarity™ Digital PCR Technology,< http://www.jnmedsys.com/digital-per-description/ (11 pgs.) (Feb. 15, 2017).
Men et al. Digital Polymerase Chain Reaction in an Array of Femtoliter Polydimethylsiloxane Microreactors. Anal Chem 84:4262-4266 (2012).
Morrison et al. Nanoliter high through quantitative PCR. Nucleic Acids Res 34(18):e123 (2006).
Ottesen et al. Microfluidic digital PCR enables multigene analysis of individual environmental bacteria. Science 314(5804):1464-1467 (2006).
PCT/US2017/025873 International Search Report and Written Opinion dated Aug. 25, 2017.
PCT/US2017/025873 Invitation to Pay Additional Fees dated Jun. 19, 2017.
PCT/US2017/062078 International Search Report and Written Opinion dated Jan. 30, 2018.
PCT/US2018/025873 International Preliminary Report on Patentability dated Oct. 18, 2018.
PCT/US2019/025539 Invitation to Pay Additional Fees dated Jun. 10, 2019.
Ramakrishnan et al. Integrated Fluidic Circuits (IFCs) for digital PCR. Methods Mol Biol 949:423-431 (2013).
Saiki, et al. Primer-directed enzymatic amplification of DNA with a thermostable DNA polymerase. Science, 239(4839):487-491 (Jan. 29, 1988).
Shen et al. Digital PCR on a SlipChip. Lab Chip 10:2666-2672 (2010).
Stilla. Crystal Digital PCR. http://www.stilla.fr/index.html#crystal-digital-perhttp://www.stilla.fr/index.html (6 pgs.) (Feb. 15, 2017).
U.S. Appl. No. 16/026,827 Office Action dated Aug. 16, 2018.
Vogelstein et al. Digital PCR. PNAS 96(16):9236-9241 (1999).
U.S. Appl. No. 15/783,743 Office Action dated Sep. 26, 2019.
Vykoukal et al. Quantitative Detection of Bioassays with a Low-Cost Image-Sensor Array for Integrated Microsystems. Angewandte Chemie 48:7649-7654 (2009).

* cited by examiner

SEQUENCE LISTING

<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic

```
        primer

<400> SEQUENCE: 1
gcctcaataa agcttgcctt ga                                          22

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggggcgcact gctagaga                                               18

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
ccagagtcac acaacagacg ggcaca                                      26
```

METHODS AND SYSTEMS FOR NUCLEIC ACID ANALYSIS AND QUANTIFICATION

CROSS-REFERENCE

This application is a continuation of PCT Application Ser. No. PCT/US2017/062078, filed Nov. 16, 2017, which claims the benefit of U.S. Provisional Patent Application Ser. No. 62/423,601, filed Nov. 17, 2016, each of which is entirely incorporated herein by reference.

GOVERNMENT INTEREST STATEMENT

This invention was made with government support under Small Business Innovation Research grant number 1R43OD023028-01 and 1R43HG009640 awarded by the National Institute of Health. The U.S. government has certain rights in the invention.

SEQUENCE LISTING

The instant application contains a Sequence Listing which has been submitted electronically in ASCII format and is hereby incorporated by reference in its entirety. The ASCII copy, created on May 8, 2019, is named 51674703301SL.txt and is 1,021 bytes is size.

BACKGROUND

Microfluidic devices are devices that contain structures that handle fluids on a small scale. Typically, a microfluidic device operates on a sub-millimeter scale and handles micro-liters, nano-liters, or smaller quantities of fluids. In microfluidic devices, a major fouling mechanism is trapped air, or bubbles, inside the micro-structure. This can be particularly problematic when using a thermoplastic material to create the microfluidic structure, as the gas permeability of thermoplastics is very low.

In order to avoid fouling by trapped air, previous microfluidic structures use either simple straight channel or branched channel designs with thermoplastic materials, or else manufacture the device using high gas permeability materials such as elastomers. However, simple designs limit possible functionality of the microfluidic device, and elastomeric materials are both difficult and expensive to manufacture, particularly at scale.

One application of microfluidic structures is in digital polymerase chain reaction (dPCR). dPCR dilutes a nucleic acid sample down to one or less nucleic acid template in each partition of a microfluidic structure providing an array of many partitions, and performs a PCR reaction across the array. By counting the partitions in which the template was successfully PCR amplified and applying Poisson statistics to the result, the target nucleic acid is quantified. Unlike the popular quantitative real-time PCR (qPCR) where templates are quantified by comparing the rate of PCR amplification of an unknown sample to the rate for a set of known qPCR standards, dPCR has proven to exhibit higher sensitivity, better precision and greater reproducibility.

For genomic researchers and clinicians, dPCR is particularly powerful in rare mutation detection, quantifying copy number variants, and Next Gen Sequencing library quantification. The potential use in clinical settings for liquid biopsy with cell free DNA and viral load quantification further increases the value of dPCR technology. Existing dPCR solutions have used elastomeric valve arrays, silicon through-hole approaches, and microfluidic encapsulation of droplets in oil. Despite the growing number of available dPCR platforms, dPCR has been at a disadvantage when compared to the older qPCR technology which relies on counting the number of PCR amplification cycles. The combination of throughput, ease of use, performance and cost are the major barriers for gaining adoption in the market for dPCR.

SUMMARY

Provided herein are methods and systems that may be useful for amplifying and quantifying nucleic acids and detecting the presence or absence of targets (e.g., actual or suspected targets), such as, for example, pathogens (e.g., bacteria). The present disclosure provides methods, systems, and devices that may enable sample preparation, sample amplification, and sample analysis through the use of digital polymerase chain reaction (dPCR). This may enable a nucleic acid to be amplified and quantified at a reduced cost and complexity as compared to other systems and methods.

Methods and systems of the present disclosure may employ high resolution melting (HRM) analysis for detecting nucleic acid (e.g., deoxyribonucleic acid, DNA) sequence variants. HRM methods of the present disclosure can create sequence-dependent melting curves with single nucleotide resolution, all completed through seamless integration with nucleic acid amplification, such as polymerase chain reaction (PCR), in some cases without any post amplification processing steps. Coupled with broad-range PCR, HRM methods and systems of the present disclosure can greatly expand the breadth of sequence variants which can be identified.

Recognized herein are various limitations associated with melt curve approaches that are currently available. Conventional bulk PCR/HRM analysis design may be limited in addressing several critical needs in genetic and epigenetic analyses. One critical limitation is inadequate sensitivity due to interference from PCR inhibitors or excess background human DNA. Another critical limitation is its inability to dissect multiple sequence variants in a heterogeneous population and accurately quantify each variant.

Recognized herein is the need to determine absolute quantities of rare allelic variants and relative allelic ratios. In infectious diseases, accurate detection and identification of minute pathogen load, and quantitative resolution of mixed microbial populations to differentiate infection from colonization or contamination further underscore the importance in quantitatively distinguishing variants co-existing in a sample.

The present disclosure provides a digital HRM analysis platform that integrates absolute quantification in digital PCR (dPCR) with HRM analysis. This can provide for deep analyses at the single-molecule level and in a high-throughput manner.

In an aspect, the present disclosure provides a method for analyzing a plurality of nucleic acid molecules comprising providing a device comprising a plurality of partitions, wherein at least a subset of the plurality of partitions comprises the plurality of nucleic acid molecules, wherein each partition of the at least the subset of the plurality of partitions is configured to permit gas flow from the at least the subset of the plurality of partitions to an environment external to the at least the subset of the plurality of partitions through at least one barrier separating the at least the subset of the plurality of partitions from the external environment; while subjecting the at least the subset of the plurality of partitions to controlled heating, collecting signals from the at least the subset of the plurality of partitions; and processing the collected signals to yield data indicative of a melting point of at least a subset of the plurality of nucleic acid molecules in the at least the subset of the plurality of partitions.

In some embodiments, the method further comprises, prior to providing the device comprising the plurality of nucleic acid molecules, performing nucleic acid amplification reactions on a nucleic acid sample under conditions sufficient to yield the plurality of nucleic acid molecules as amplification products of the nucleic acid sample. In some embodiments, the method further comprises loading the nucleic acid sample into the at least the subset of the plurality of partitions prior to performing the nucleic acid amplification reactions. In some embodiments, the nucleic acid amplification reactions are performed in the at least the subset of the plurality of partitions. In some embodiments, performing nucleic acid amplification reactions on the nucleic acid sample comprises amplifying at least a portion of an internal transcribed spacer region of at least a subset of the nucleic acid molecules of the nucleic acid sample. In some embodiments, nucleic acid amplification reactions use one or more reagents selected from the group consisting of primers, deoxyribonucleotides, buffers, co-factors, intercalating dyes, and polymerases. In some embodiments, the one or more reagents comprise a fluorophore or fluorescent label. In some embodiments, the method further comprises, prior to performing nucleic acid amplification reactions on the nucleic acid sample, contacting at least a subset of the nucleic acid molecules of the nucleic acid sample with an intercalating dye.

In some embodiments, collecting signals from the at least the subset of the plurality of partitions while subjecting the at least the subset of the plurality of partitions to controlled heating is performed over a plurality of time points.

In some embodiments, collecting signals from the at least the subset of the plurality of partitions while subjecting the at least the subset of the plurality of partitions to controlled heating comprises imaging the at least the subset of the plurality of partitions to collect the signals.

In some embodiments, processing the collected signals comprises using the signals to generate signal versus temperature data for the at least the subset of the plurality of nucleic acid molecules in the at least the subset of the plurality of partitions.

In some embodiments, the plurality of nucleic acid molecules are derived from a sample containing or suspected of containing a pathogen. In some embodiments, the pathogen is at least one bacterium. In some embodiments, the at least one bacterium is selected from the group consisting of *Bacillus anthracis, Bacillus cereus, Bacillus halodurans, Bacillus mycoides, Bacillus polymexa, Bacillus subtilis, Bacillus thuringensis, Staphylococcus capitis, Staphylococcus caprae, Staphylococcus haemolyticus, Staphylococcus hominis, Staphylococcus lentus, Staphylococcus lugdunensis, Staphylococcus saprophyticus, Staphylococcus xylosus, Propionibacterium acnes, Enterococcus faecalis*, Actinobacteria, Alphaproteobacteria, Bacteroidetes, Betaproteobacteria, Chlamydiaes, Epsilonproteobacteria, Firmicutes, Gammaproteobacteria, Spirochaetales, and Tenericutes. In some embodiments, the method further comprises, prior to providing the device comprising the plurality of nucleic acid molecules, isolating or extracting the plurality of nucleic acid molecules, or a subset thereof, from the at least one bacterium. In some embodiments, the method further comprises using the data indicative of a melting point to determine the presence or absence of the pathogen in each partition of the at least the subset of the plurality of partitions.

In some embodiments, the sample from which the plurality of nucleic acid molecules is derived is a biological sample. In some embodiments, the biological sample comprises a bodily fluid selected from the group consisting of blood, urine, semen, mucus, and saliva. In other embodiments, the sample from which the plurality of nucleic acid molecules is derived is an environmental sample.

In some embodiments, providing the device further comprises loading the plurality of nucleic acid molecules into the plurality of partitions, wherein during the loading, gas in the at least the subset of the plurality of partitions is subjected to flow from the at least the subset of the plurality of partitions to the environment external to the at least the subset of the plurality of partitions.

In some embodiments, the barrier comprises a polymeric material. In some embodiments, the polymeric material is a thermoplastic material. In some embodiments, the barrier is at least partially permeable to a gas under a pressure differential applied across the barrier. In some embodiments, the barrier is substantially optically transparent. In some embodiments, the barrier has a thickness from about 50 μm to about 200 μm.

In some embodiments, the device comprises at least one microchannel comprising at least one inlet, at least one outlet, and a plurality of siphon apertures, wherein each of the at least the subset of the plurality of partitions is in fluid communication with the at least one microchannel by the plurality of siphon apertures.

In some embodiments, the plurality of partitions comprises from about 1,000 to about 20,000 partitions.

In some embodiments, the plurality of nucleic acid molecules is deoxyribonucleic acid molecules. In other embodiments, the plurality of nucleic acid molecules is ribonucleic acid molecules.

In another aspect, the present disclosure provides a method for analyzing a plurality of nucleic acid molecules, comprising: providing a device comprising a plurality of partitions, wherein at least a subset of the plurality of partitions comprises the plurality of nucleic acid molecules, wherein each partition of the at least the subset of the plurality of partitions is configured to permit gas flow from the at least the subset of the plurality of partitions to an environment external to the at least the subset of the plurality of partitions through at least one barrier separating the at least the subset of the plurality of partitions from the external environment; subjecting the at least the subset of the plurality of partitions to conditions sufficient to conduct nucleic acid amplification reactions using the plurality of nucleic acid molecules to generate amplification products from at least a subset of the plurality of nucleic acid molecules; while subjecting the at least the subset of the plurality of partitions to the conditions, collecting signals from the at least the subset of the plurality of partitions over a plurality of time points; and processing the signals to determine a number of nucleic acid molecules in the at least the subset of the plurality of partitions.

In some embodiments, subjecting the at least the subset of the plurality of partitions to conditions sufficient to conduct nucleic acid amplification reactions comprises thermal cycling, and collecting signals comprises collecting signals from each partition of the at least the subset of the plurality of partitions more than once per thermal cycle. In some embodiments, the thermal cycling comprises a denaturation phase, an extension phase, and an annealing phase. In some embodiments, the thermal cycling is performed using a flat block thermal cycler.

In some embodiments, the nucleic acid amplification reactions use or one or more reagents selected from the group consisting of primers, deoxyribonucleotides, buffers, co-factors, intercalating dyes, and polymerases. In some embodiments, the one or more reagents comprise a fluorophore or fluorescent label. In some embodiments, collecting signals from the at least the subset of the plurality of partitions over a plurality of time points comprises imaging the at least the subset of the plurality of partitions to collect the signals. In some embodiments, the at least the subset of the plurality of partitions are imaged simultaneously. In some embodiments, imaging is performed using a detector that detects fluorescence emission at two or more wavelengths. In some embodiments, processing signals to determine a number of nucleic acid molecules in the at least the subset of the plurality of partitions comprises determining an optical intensity for each partition of the at least the subset of the plurality of partitions, wherein the optical intensity is proportional to the amount of amplification products in each of the at least the subset of the plurality of partitions.

In some embodiments, providing the device comprising the plurality of nucleic acid molecules further comprises loading the plurality of nucleic acid molecules into the plurality of partitions, wherein during the loading, gas in the at least the subset of the plurality of partitions is subjected to flow from the at least the subset of the plurality of partitions to the environment external to the at least the subset of the plurality of partitions.

In some embodiments, the barrier comprises a polymeric material. In some embodiments, the polymeric material is a thermoplastic material. In some embodiments, the barrier is at least partially permeable to a gas under a pressure differential applied across the barrier. In some embodiments, the barrier is substantially optically transparent. In some embodiments, the barrier has a thickness from about 50 µm to about 200 µm.

In some embodiments, the device comprises at least one microchannel comprising at least one inlet, at least one outlet, and a plurality of siphon apertures, wherein each of the at least the subset of the plurality of partitions is in fluid communication with the at least one microchannel by the plurality of siphon apertures.

In some embodiments, the plurality of partitions comprises from about 1,000 to about 20,000 partitions.

In some embodiments, the plurality of nucleic acid molecules are deoxyribonucleic acid molecules. In other embodiments, the plurality of nucleic acid molecules are ribonucleic acid molecules.

In a further aspect, the present disclosure provides a system for analyzing a plurality of nucleic acid molecules comprising: a support unit configured to accept a device comprising a plurality of partitions, wherein each partition of the at least the subset of the plurality of partitions is configured to permit gas flow from the at least the subset of the plurality of partitions to an environment external to the at least the subset of the plurality of partitions through at least one barrier separating the at least the subset of the plurality of partitions from the external environment; a detector configured to collect signals from the at least the subset of the plurality of partitions over a plurality of time points; and one or more computer processors operatively coupled to the detector, wherein the one or more computer processors are individually or collectively programmed to: (i) subject the at least the subset of the plurality of partitions to conditions sufficient to conduct nucleic acid amplification reactions using the plurality of nucleic acid molecules to generate amplification products from at least a subset of the plurality of nucleic acid molecules; (ii) while subjecting the at least the subset of the plurality of partitions to the conditions in (i), receive the signals collected from the at least the subset of the plurality of partitions by the detector over the plurality of time points; and (iii) process the signals to determine a number of nucleic acid molecules in the at least the subset of the plurality of partitions.

In some embodiments, the system further comprises a fluid flow unit that is configured to direct the plurality of nucleic acid molecules to the plurality of partitions. In some embodiments, the one or more computer processors are individually or collectively programmed to direct the fluid flow unit to load the plurality of nucleic acid molecules into the plurality of partitions.

In another aspect, the present disclosure provides a system for analyzing a plurality of nucleic acid molecules, comprising: a support unit configured to accept a device comprising a plurality of partitions, wherein each partition of the at least the subset of the plurality of partitions is configured to permit gas flow from the at least the subset of the plurality of partitions to an environment external to the at least the subset of the plurality of partitions through at least one barrier separating the at least the subset of the plurality of partitions from the external environment; a thermal unit configured to subject the at least the subset of the plurality of partitions to controlled heating; a detector configured to collect signals from at least a subset of the plurality of partitions; and one or more computer processors operatively coupled to the thermal unit and the detector, wherein the one or more computer processors are individually or collectively programmed to: (i) direct the thermal unit to subject the at least the subset of the plurality of partitions to controlled heating; (ii) receive the signals collected from the at least the subset of the plurality of partitions by the detector while the at least the subset of the plurality of partitions are subjected to controlled heating; and (iii) process the signals collected in (ii) to yield data indicative of a melting point of at least a subset of the plurality of nucleic acid molecules in the at least the subset of the plurality of partitions.

In some embodiments, the system further comprises a fluid flow unit that is configured to direct the plurality of nucleic acid molecules to the plurality of partitions. In some embodiments, the one or more computer processors are individually or collectively programmed to direct the fluid flow unit to load the plurality of nucleic acid molecules into the plurality of partitions.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1A shows the structure from an overhead view, while FIG. 1B illustrates a cross-section of the structure;

FIG. 2A shows an embodiment in which parallel sub-channels and one or more cross-channels are used to form a grid of microchambers; FIG. 2B shows an embodiment in which a single microchannel in a serpentine pattern forms a hexagonal grid of microchambers;

FIG. 3A shows a step of applying reagent at low pressure; FIG. 3B shows a step of applying a pressure differential across the microfluidic device to force partitioning and outgassing; FIG. 3C shows a step of applying fluid at low pressure to clear the microchannel; FIG. 3D shows the state of the system after the completion of the method;

FIG. 8A shows a microfluidic device formed by micromolding a thermoplastic; FIG. 8B show fluorescent images of the sample partitioning process;

FIG. 10A shows zero copies per partition (NTC) after amplification; FIG. 10B shows nucleic acid amplification of partitions containing approximately one copy per partition; FIG. 10C shows a plot of NTC fluorescence intensity of both fluorescent colors; and FIG. 10D shows a plot of fluorescence intensity of both fluorescent colors of the amplified sample;

FIG. 11A shows a representation of the partitions of an exemplary microfluidic device; FIG. 11B shows the amplification dynamics of the samples in each partition of the exemplary device; FIG. 11C shows the results of a qdPCR process applied to the amplification dynamics shown in FIG. 11B;

FIG. 12A show the device; FIG. 12B illustrates an arrangement of a portion of the partitions within one reaction array of the device;

FIG. 14A illustrates the flat-block thermal cycling unit; FIG. 14B illustrates the flat block thermal cycling unit of FIG. 14A with the addition of a pneumatic clamp, with the clamp opened so that a device such as the device of FIG. 12A may be loaded into the thermal cycling unit;

FIG. 17A shows the entire example system for processing a nucleic acid molecule; FIG. 17B shows the portion of the example system including imaging components and a device for sample processing and/or analysis;

FIG. 20A shows images of a subset of partitions in a device including different numbers of nucleic acid molecules; FIG. 20B shows a Poisson analysis of the images of FIG. 20A;

FIG. 22A illustrates the differences between digital and bulk HRM analyses; FIG. 22B shows HRM curves for different bacterial species and their use to determine occupation of partitions;

FIG. 23A shows 16S and internal transcribed spacer (ITS) composite derivative HRM curves for various bacteria; FIG. 23B shows HRM curves for different species of the *Bacilus* genus; FIG. 23C shows HRM curves for different species of the *Staphylococcus* genus; FIG. 23D shows ITS HRM curves for different species of *S. pneumonia*; FIG. 23E shows a heat map of ITS sequence homology for different bacterial species organized by phylum;

FIG. 24A illustrates partitioning of DNA from a sample including a plurality of DNA molecules; FIG. 24B shows temperature dependent fluorescent signal corresponding to different theoretical partition populations;

DETAILED DESCRIPTION

Figure 1A:
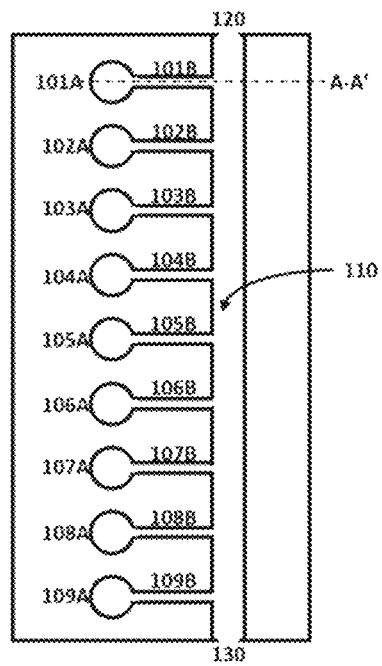
FIGS. 1A and 1B illustrate an example of a microfluidic structure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the terms "amplification" and "amplify" are used interchangeably and generally refer to generating one or more copies or "amplified product" of a nucleic acid. Such amplification may be using polymerase chain reaction (PCR) or isothermal amplification, for example.

As used herein, the term "nucleic acid" generally refers to a polymeric form of nucleotides of any length (e.g., at least 2, 3, 4, 5, 6, 7, 8, 9, 10, 100, 500, or 1000 nucleotides), either deoxyribonucleotides or ribonucleotides, or analogs thereof. A nucleic acid may include one or more subunits selected from adenosine (A), cytosine (C), guanine (G), thymine (TO, and uracil (U), or variants thereof. A nucleotide can include A, C, G, T, or U, or variants thereof. A nucleotide can include any subunit that can be incorporated into a growing nucleic acid strand. Such subunit can be A, C, G, T, or U, or any other subunit that is specific to one of more complementary A, C, G, T, or U, or complementary to a purine (i.e., A or G, or variant thereof) or pyrimidine (i.e., C, T, or U, or variant thereof). In some examples, a nucleic acid may be single-stranded or double stranded, in some cases, a nucleic acid molecule is circular. Non-limiting examples of nucleic acids include deoxyribonucleic acid (DNA) and ribonucleic acid (RNA). Nucleic acids can include coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs.

As used herein, the terms "polymerase chain reaction reagent" or "PCR reagent" are used interchangeably and generally refer to a composition comprising reagents necessary to complete a nucleic acid amplification reaction (e.g., DNA amplification), with non-limiting examples of such reagents including primer sets or priming sites (e.g., nick) having specificity for a target nucleic acid, polymerases, suitable buffers, co-factors (e.g., divalent and monovalent cations), dNTPs, and other enzymes. A PCR reagent may also include probes, indicators, and molecules that comprise probes and indicators.

As used herein, the term "probe" generally refers to a molecule that comprises a detectable moiety, the presence or absence of which may be used to detect the presence or absence of an amplified product. Non-limiting examples of detectable moieties may include radiolabels, stable isotope labels, fluorescent labels, chemiluminescent labels, enzymatic labels, colorimetric labels, or any combination thereof.

As used herein, the term "extension" generally refers to incorporation of nucleotides into a nucleic acid in a template directed fashion. Extension may occur via the aid of an enzyme. For example, extension may occur via the aid of a polymerase. Conditions at which extension may occur include an "extension temperature" that generally refers to a temperature at which extension is achieved and an "extension duration" that generally refers to an amount of time allotted for extension to occur.

As used herein, the term "indicator molecule" generally refers to a molecule that comprises a detectable moiety, the presence or absence of which may be used to indicate sample partitioning. Non-limiting examples of detectable moieties may include radiolabels, stable isotope labels, fluorescent labels, chemiluminescent labels, enzymatic labels, colorimetric labels, or any combination thereof.

The term "sample," as used herein, generally refers to any sample containing or suspected of containing a nucleic acid molecule. The nucleic acid molecule may be in or from a cellular sample or organism, such as, for example, a bacterium or bacteria. For example, a sample can be a biological sample containing one or more nucleic acid molecules. The biological sample can be obtained (e.g., extracted or isolated) from or include one or more components selected from the group consisting of blood (e.g., whole blood), plasma, serum, urine, saliva, mucosal excretions, sputum, stool, and tears. The biological sample may be a fluid or tissue sample (e.g., skin sample). The sample may be obtained from a cell-free bodily fluid, such as whole blood. A sample from a cell-free bodily fluid may include cell-free DNA and/or cell-free RNA. The sample may include circulating tumor cells. The sample may be taken from a subject and the analysis of nucleic acids included therein used for diagnostic purposes. Alternatively, the sample may be an environmental sample (e.g., soil, waste, ambient air and etc.), industrial sample (e.g., samples from any industrial processes), or food sample (e.g., dairy products, vegetable products, and meat products).

As used herein, the term "fluid" generally refers to a liquid or a gas. A fluid cannot maintain a defined shape and will flow during an observable time frame to fill the container into which it is put. Thus, the fluid may have any suitable viscosity that permits flow. If two or more fluids are present, each fluid may be independently selected among essentially any fluids (liquids, gases, and the like) by those of ordinary skill in the art.

As used herein, the term "partition" generally refers to a division into or distribution into portions or shares. For example, a partitioned sample is a sample that is isolated from other samples. Examples of structures that enable sample partitioning include wells and microchambers.

As used herein, the term "microfluidic" generally refers to a chip, area, device, article, or system including at least one microchannel, a plurality of siphon apertures, and an array of microchambers. The microchannel may have a cross-sectional dimension less than or equal to about 10 millimeters (mm), less than or equal to about 5 mm, less than or equal to about 4 mm, less than or equal to about 3 mm, less than or equal to about 2 mm, less than or equal to about 1.5 mm, less than or equal to about 1 mm, less than or equal to about 750 micrometers (μm), less than or equal to about 500 μm, less than or equal to about 250 μm, less than or equal to about 100 μm, or less.

As used herein, the term "depth" generally refers to the distance measured from the bottom of the microchannel, siphon aperture, or partition (e.g., microchamber) to the thin film that caps the microchannel, plurality of siphon apertures, and array of partitions (e.g., microchambers).

As used herein, the terms "cross-section" or "cross-sectional" may be used interchangeably and generally refer to a dimension or area of a microchannel or siphon aperture that is substantially perpendicularly to the long dimension of the feature.

The present disclosure describes methods involving the use of and systems comprising a microfluidic device formed out of a polymeric material, such as a thermoplastic material, and incorporating a thin film to allow for pressurized outgassing while serving as a gas barrier when pressure is released. The use of thermoplastic to form the microfluidic structure may allow for the use of an inexpensive and highly scalable injection molding process, while the thin film may provide the ability to outgas via pressurization, avoiding the fouling problems that may be present some microfluidic structures that do not incorporate such thin films.

One use for this structure is a microfluidic design incorporating an array of dead-ended microchambers connected by microchannels, formed, e.g., out of thermoplastics. This design can be used, e.g., in a digital PCR (dPCR) or quantitative dPCR (qdPCR) application to partition reagents into the array of microchambers and thereby used to quantify nucleic acids or in a high resolution melt (HRM) analysis to analyze the quantity and characteristics of nucleic acids partitioned amongst the array of microchambers.

Microfluidic Device for Analyzing Samples

In an aspect, the present disclosure provides methods of using and systems comprising a microfluidic device for processing and/or analyzing samples. The device may comprise a microchannel connected to an inlet and an outlet. The microfluidic device may also include a plurality of microchambers and a plurality of siphon apertures. The plurality of microchambers may be connected to the microchannel by the plurality of siphon apertures. The microfluidic device may include a thermoplastic thin film which caps and seals (e.g., hermetically seals) the microchannel, microchambers, and siphon apertures. The thermoplastic thin film may be at least partially gas permeable when a pressure differential is applied across the thermoplastic thin film.

Figure 1B:
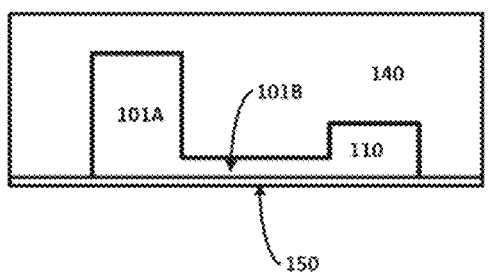

FIGS. 1A and 1B show examples of a microfluidic structure according to certain embodiments of the present disclosure. FIG. 1A shows an example microfluidic device from a top view. The microfluidic device comprises a microchannel 110, with an inlet 120, and an outlet 130. The microchannel is connected to a plurality of siphon apertures 101B-109B. The plurality of siphon apertures connects the microchannel to a plurality of microchambers 101A-109A. FIG. 1B shows a cross-sectional view of a single microchamber along the dashed line marked A-A'. The single microchamber 101A is connected to the microchannel 110 by a siphon aperture 101B. The microfluidic device body 140 may be formed from a rigid plastic material (e.g., a thermoplastic material). The microstructures of the microfluidic device may be capped and sealed by a thin film 150. Thin film 150 may be gas impermeable when a small pressure differential is applied across the film and gas permeable when a large pressure differential is applied across the film. This may allow for outgassing through thin film 150 when a pressure is applied to the interior structure of the microfluidic device. Alternatively, outgassing may occur when a vacuum is applied external to the microfluidic device.

The gas permeability of the thin film may be induced by elevated pressures. The pressure induced gas permeable thin film may cover the array of microchambers, or a subset thereof, and the microchannel and siphon apertures may be covered by a non-gas permeable film. Alternatively, the pressure induced gas permeable thin film may cover the array of microchambers, or a subset thereof, and the siphon apertures and the microchannel may be covered by a non-gas permeable film. Alternatively, the pressure induced gas permeable thin film may cover the array of microchambers, or a subset thereof, the siphon apertures, and the microchannel. The thickness of the thin film may be less than or equal to about 500 micrometers (μm), less than or equal to about 250 μm, less than or equal to about 200 μm, less than or equal to about 150 μm, less than or equal to about 100 μm, less than or equal to about 75 μm, less than or equal to about 50 μm, less than or equal to about 25 μm, or less. The thickness of the thin film may be from about 0.1 μm to about 200 μm or about 0.5 μm to about 150 μm. For example, the thickness of the thin film may be from about 50 μm to about 200 μm. In some examples, the thickness of the thin film may be from about 100 μm to about 200 μm. For example, the thickness of the thin film is about 100 μm to about 150 μm. In an example, the thin film is approximately 100 μm in thickness. The thickness of the film may be selected by manufacturability of the thin film, the air permeability of the thin film, the volume of each partition to be out-gassed, the available pressure, and/or the desired time to complete the siphoning process, among other factors.

The microfluidic device may comprise a single array of microchambers. Alternatively, the microfluidic device may comprise multiple arrays of microchambers, each array of microchambers isolated from the others. The arrays of microchambers may be arranged in a row, in a grid configuration, in an alternating pattern, or in any other configuration. The microfluidic device may have at least about 1, at least about 2, at least about 3, at least about 4, at least about 5, at least about 10, at least about 15, at least about 20, at least about 30, at least about 40, at least about 50, or more arrays of microchambers. The arrays of microchambers may be identical. The microfluidic device may comprise multiple arrays of microchambers that are not identical. The arrays of microchambers may all have the same external dimension (i.e., the length and width of the array of microchambers that encompasses all features of the array of microchambers) or the arrays of microchambers may have different external dimensions.

An array of microchambers may have a width of at most about 100 mm, about 75 mm, about 50 mm, about 40 mm, about 30 mm, about 20 mm, about 10 mm, about 8 mm, about 6 mm, about 4 mm, about 2 mm, about 1 mm, or less. The array of microchambers may have a length of at most about 50 mm, about 40 mm, about 30 mm, about 20 mm, about 10 mm, about 8 mm, about 6 mm, about 4 mm, about 2 mm, 1 mm, or less. The width may be from about 1 mm to 100 mm, or 10 mm to 50 mm. The length may be from about 1 mm to 50 mm, or 5 mm to 20 mm.

In some examples, the array of microchambers may have a width of about 100 mm and a length of about 40 mm. In some examples, the array of microchambers may have a width of about 80 mm and a length of about 30 mm. In some examples, the array of microchambers may have a width of about 60 mm and a length of about 25 mm. In some examples, the array of microchambers may have a width of about 40 mm and a length of about 15 mm. In some examples, the array of microchambers may have a width of about 30 mm and a length of about 10 mm. In some examples, the array of microchambers may have a width of about 20 mm and a length of about 8 mm. In some examples, the array of microchambers may have a width of about 10 mm and a length of about 4 mm. The external dimension may be determined by the total number of microchambers desired, the dimension of each microchamber, and the minimum distance between each microchamber for manufacturability.

The microchannel may be substantially parallel or substantially perpendicular to the long dimension of the microfluidic device. Alternatively, the microchannel may be neither substantially parallel nor substantially perpendicular to the long dimension of the microfluidic device. The angle between the microchannel and the long dimension of the microfluidic device may be at least about 5°, at least about 10°, at least about 15°, at least about 20°, at least about 30°, at least about 40°, at least about 50°, at least about 60°, at least about 70°, at least about 90°, at least about 100°, at least about 110°, at least about 120°, at least about 130°, at least about 140°, at least about 150°, at least about 160°, or at least about 170°. The microchannel may be a single long channel. The microchannel may have bends, curves, or angles. The microchannel may have a long dimension that is less than or equal to 100 mm, less than or equal to about 75 mm, less than or equal to about 50 mm, less than or equal to about 40 mm, less than or equal to about 30 mm, less than or equal to about 20 mm, less than or equal to about 10 mm, less than or equal to about 8 mm, less than or equal to about 6 mm, less than or equal to about 4 mm, less than or equal to about 2 mm, or less. The length of the microchannel may be bounded by the external length or width of the microfluidic device. The microchannel may have a depth of less than or equal to about 500 µm, less than or equal to about 250 µm, less than or equal to about 100 µm, less than or equal to about 80 µm, less than or equal to about 60 µm, less than or equal to about 30 µm, less than or equal to about 20 µm, less than or equal to about 10 µm, or less. The microchannel may have a cross-sectional dimension (e.g., width) of less than or equal to about 500 µm, less than or equal to about 250 µm, less than or equal to about 100 µm, less than or equal to about 75 µm, less than or equal to about 50 µm, less than or equal to about 40 µm, less than or equal to about 30 µm, less than or equal to about 20 µm, less than or equal to about 10 µm, or less.

In some examples, the cross-sectional dimensions of the microchannel may be about 100 µm wide by about 100 µm deep. In some examples, the cross-sectional dimensions of the microchannel may be about 100 µm wide by about 80 µm deep. In some examples, the cross-sectional dimensions of the microchannel may be about 100 µm wide by about 60 µm deep. In some examples, the cross-sectional dimensions of the microchannel may be about 100 µm wide by about 40 µm deep. In some examples, the cross-sectional dimensions of the microchannel may be about 100 µm wide by about 20 µm deep. In some examples, the cross-sectional dimensions of the microchannel may be about 100 µm wide by about 10 µm deep. In some examples, the cross-sectional dimensions of the microchannel may be about 80 µm wide by about 100 µm deep. In some examples, the cross-sectional dimensions of the microchannel may be about 60 µm wide by about 100 µm deep. In some examples, the cross-sectional dimensions of the microchannel may be about 40 µm wide by about 100 µm deep. In some examples, the cross-sectional dimensions of the microchannel may be about 20 µm wide by about 100 µm deep. In some examples, the cross-sectional dimensions of the microchannel may be about 10 µm wide by about 100 µm deep. In some examples, the cross-sectional dimensions of the microchannel may be about 80 µm wide by about 80 µm deep. In some examples, the cross-sectional dimensions of the microchannel may be about 60 µm wide by about 60 µm deep. In some examples, the cross-sectional dimensions of the microchannel may be about 40 µm wide by about 40 µm deep. In some examples, the cross-sectional dimensions of the microchannel may be about 20 µm wide by about 20 µm deep. In some examples, the cross-sectional dimensions of the microchannel may be about 10 µm wide by about 10 µm deep. The cross-sectional shape of the microchannel may be any suitable cross-sectional shape including, but not limited to, circular, oval, triangular, square, or rectangular. The cross-sectional area of the microchannel may be constant along the length of the microchannel. Alternatively, or in addition, the cross-sectional area of the microchannel may vary along the length of the microchannel. The cross-sectional area of the microchannel may vary between about 50% and 150%, between about 60% and 125%, between about 70% and 120%, between about 80% and 115%, between about 90% and 110%, between about 95% and 100%, or between about 98% and 102%. The cross-sectional area of the microchannel may be less than or equal to about 10,000 micrometers squared ($\mu m^2$), less than or equal to about 7,500 $\mu m^2$, less than or equal to about 5,000 $\mu m^2$, less than or equal to about 2,500 $\mu m^2$, less than or equal to about 1,000 $\mu m^2$, less than or equal to about 750 $\mu m^2$, less than or equal to about 500 $\mu m^2$, less than or equal to about 400 $\mu m^2$, less than or equal to about 300 $\mu m^2$, less than or equal to about 200 $\mu m^2$, less than or equal to about 100 $\mu m^2$, or less.

The microchannel may have a single inlet and a single outlet. Alternatively, the microchannel may have multiple inlets, multiple outlets, or multiple inlets and multiple outlets. The inlets and outlets may have the same diameter or they may have different diameters. The inlets and outlets may have diameters less than or equal to about 2.5 millimeters (mm), less than or equal to about 2 mm, less than or equal to about 1.5 mm, less than or equal to about 1 mm, less than about 0.5 mm, or less.

The array of microchambers may have at least about 1,000 microchambers, at least about 5,000 microchambers, at least about 10,000 microchambers, at least about 20,000 microchambers, at least about 30,000 microchambers, at least about 40,000 microchambers, at least about 50,000 microchambers, at least about 100,000 microchambers, or more. In some examples, the microfluidic device may have from about 10,000 to about 30,000 microchambers. In some examples, the microfluidic device may have from about 15,000 to about 25,000 microchambers. The microchambers may be cylindrical in shape, hemispherical in shape, or a combination of cylindrical and hemispherical in shape. The microchambers may have diameters of less than or equal to about 500 µm, less than or equal to about 250 µm, less than or equal to about 100 µm, less than or equal to about 80 µm, less than or equal to about 60 µm, less than or equal to about 30 µm, less than or equal to about 15 µm, or less. The depth of the microchambers may be less than or equal to about 500 µm, less than or equal to about 250 µm, less than or equal to about 100 µm, less than or equal to about 80 µm, less than or equal to about 60 µm, less than or equal to about 30 µm, less than or equal to about 15 µm, or less. In some examples, the microchambers may have a diameter of about 30 µm and a depth of about 100 µm. In some examples, the microchambers may have a diameter of about 35 µm and a depth of about 80 µm. In some examples, the microchambers may have a diameter of about 40 µm and a depth of about 70 µm. In some examples, the microchambers may have a diameter of about 50 µm and a depth of about 60 µm. In some examples, the microchambers may have a diameter of about 60 µm and a depth of about 40 µm. In some examples, the microchambers may have a diameter of about 80 µm and a depth of about 35 µm. In some examples, the microchambers may have a diameter of about 100 µm and a depth of about 30 µm. The microchambers and the microchannel may have the same depth. Alternatively, the microchambers and the microchannel may have different depths.

The lengths of the siphon apertures may be constant. Alternatively, the lengths of the siphon apertures may vary. The siphon apertures may have a long dimension that is less than or equal to about 150 µm, less than or equal to about 100 µm, less than or equal to about 50 µm, less than or equal to about 25 µm, less than or equal to about 10 µm, less than or equal to about 5 µm, or less. The depth of the siphon aperture may be less than or equal to about 50 µm, less than or equal to about 25 µm, less than or equal to about 10 µm, less than or equal to about 5 µm or less. The siphon apertures may have a cross-sectional width less than or equal to about 50 µm, less than or equal to about 40 µm, less than or equal to about 30 µm, less than or equal to about 20 µm, less than or equal to about 10 µm, less than or equal to about 5 µm, or less.

In some examples, the cross-sectional dimensions of the siphon aperture may be about 50 µm wide by about 50 µm deep. In some examples, the cross-sectional dimensions of the siphon aperture may be about 50 µm wide by about 40 µm deep. In some examples, the cross-sectional dimensions of the siphon aperture may be about 50 µm wide by about 30 µm deep. In some examples, the cross-sectional dimensions of the siphon aperture may be about 50 µm wide by about 20 µm deep. In some examples, the cross-sectional dimensions of the siphon aperture may be about 50 µm wide by about 10 µm deep. In some examples, the cross-sectional dimensions of the siphon aperture may be about 50 µm wide by about 5 µm deep. In some examples, the cross-sectional dimensions of the siphon aperture may be about 40 µm wide by about 50 µm deep. In some examples, the cross-sectional dimensions of the siphon aperture may be about 30 µm wide by about 50 µm deep. In some examples, the cross-sectional dimensions of the siphon aperture may be about 20 µm wide by about 50 µm deep. In some examples, the cross-sectional dimensions of the siphon aperture may be about 10 µm wide by about 50 µm deep. In some examples, the cross-sectional dimensions of the siphon aperture may be about 5 µm wide by about 50 µm deep. In some examples, the cross-sectional dimensions of the siphon aperture may be about 40 µm wide by about 40 µm deep. In some examples, the cross-sectional dimensions of the siphon aperture may be about 30 µm wide by about 30 µm deep. In some examples, the cross-sectional dimensions of the siphon aperture may be about 20 µm wide by about 20 µm deep. In some examples, the cross-sectional dimensions of the siphon aperture may be about 10 µm wide by about 10 µm deep. In some examples, the cross-sectional dimensions of the siphon aperture may be about 5 µm wide by about 5 µm deep. The cross-sectional shape of the siphon aperture may be any suitable cross-sectional shape including, but not limited to, circular, oval, triangular, square, or rectangular. The cross-sectional area of the siphon aperture may be constant along the length of the siphon aperture. Alternatively, or in addition, the cross-sectional area of the siphon aperture may vary along the length of the siphon aperture. The cross-sectional area of the siphon aperture may be greater at the connection to the microchannel than the cross-sectional area of the siphon aperture at the connection to the microchamber. Alternatively, the cross-sectional area of the siphon aperture at the connection to the microchamber may be greater than the cross-sectional area of the siphon aperture at the connection to the microchannel. The cross-sectional area of the siphon aperture may vary between about 50% and 150%, between about 60% and 125%, between about 70% and 120%, between about 80% and 115%, between about 90% and 110%, between about 95% and 100%, or between about 98% and 102%. The cross-sectional area of the siphon aperture may be less than or equal to about 2,500 µm$^2$, less than or equal to about 1,000 µm$^2$, less than or equal to about 750 µm$^2$, less than or equal to about 500 µm$^2$, less than or equal to about 250 µm$^2$, less than or equal to about 100 µm$^2$, less than or equal to about 75 µm$^2$, less than or equal to about 50 µm$^2$, less than or equal to about 25 µm$^2$, or less. The cross-sectional area of the siphon aperture at the connection to the microchannel may be less than or equal to the cross-sectional area of the microchannel. The cross-sectional area of the siphon aperture at the connection to the microchannel may be less than or equal to about 98%, less than or equal to about 95%, less than or equal to about 90%, less than or equal to about 85%, less than or equal to about 80%, less than or equal to about 75%, less than or equal to about 70%, less than or equal to about 60%, less than or equal to about 50%, less than or equal to about 40%, less than or equal to about 30%, less than or equal to about 20%, less than or equal to about 10%, less than or equal to about 5%, less than or equal to about 1%, or less than or equal to about 0.5% of the cross-sectional area of the microchannel.

The siphon apertures may be substantially perpendicular to the microchannel. Alternatively, the siphon apertures may not be substantially perpendicular to the microchannel. An angle between the siphon apertures and the microchannel may be at least about 5°, at least about 10°, at least about 15°, at least about 20°, at least about 30°, at least about 40°, at least about 50°, at least about 60°, at least about 70°, at least about 90°, at least about 100°, at least about 110°, at least about 120°, at least about 130°, at least about 140°, at least about 150°, at least about 160°, or at least about 170°.

Figure 2A:
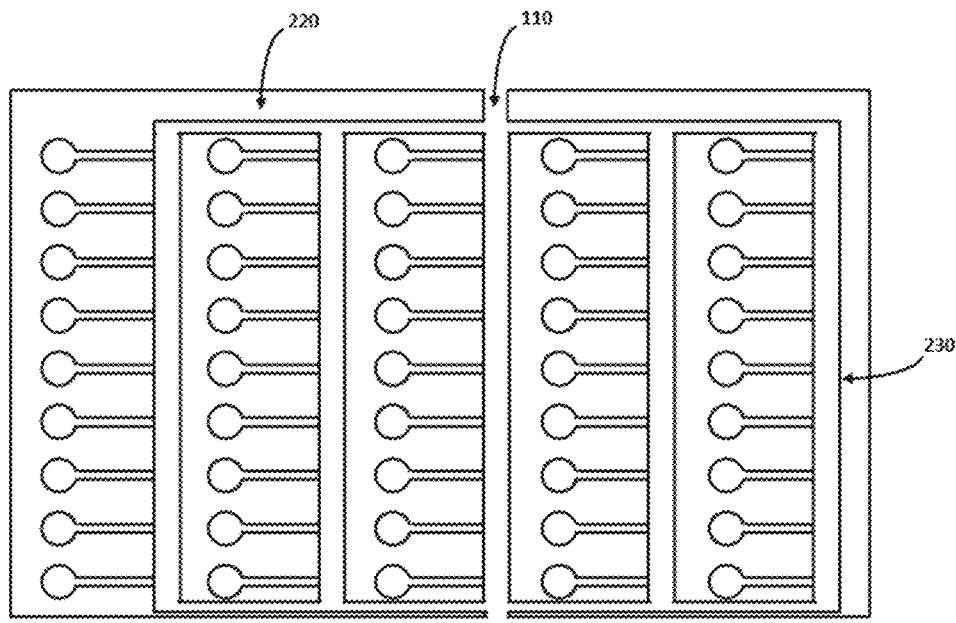
FIGS. 2A and 2B schematically illustrates example arrangements of microchambers, siphon apertures, and microchannels within a microfluidic device.
Figure 2B:
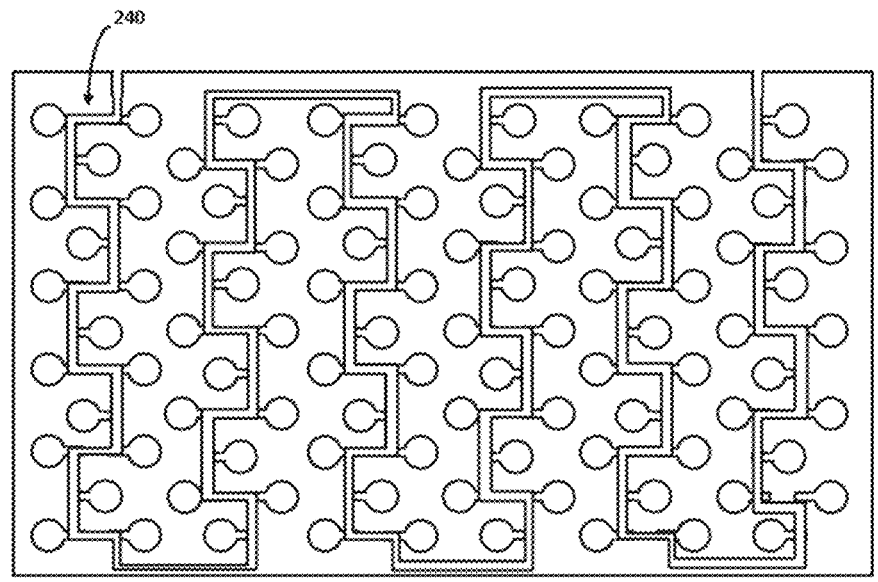

The microchambers may be arranged in a variety of patterns. FIGS. 2A and 2B illustrate exemplary patterns of microchamber, siphon aperture, and microchannel arrangements. Multiple microchannels may be employed, or a single microchannel may be used. A microchannel may comprise a group of sub-channels. The group of sub-channels may be connected by one or more cross-channels. The sub-channels may be substantially parallel to one another so that the array of microchambers forms a grid of microchambers. FIG. 2A illustrates an embodiment in which parallel sub-channels 230 and one or more cross-channels 220 are used to form a grid of microchambers.

Microchambers may be constructed so as to form a hexagonal grid of microchambers, with curved or angled sub-channels connecting the microchambers. A hexagonal grid of microchambers may also be formed and connected by a single microchannel, such as by a microchannel that forms a serpentine pattern 240 across the microfluidic device. FIG. 2B illustrates an embodiment in which a single microchannel in a serpentine pattern forms a hexagonal grid of microchambers. Another example of microchambers arranged in a serpentine configuration is shown in FIG. 12B.

The lengths of the sub-channels may be constant. Alternatively, the lengths of the sub-channel may vary. The sub-channel may have a long dimension that is less than or equal to 100 mm, less than or equal to about 75 mm, less than or equal to about 50 mm, less than or equal to about 40 mm, less than or equal to about 30 mm, less than or equal to about 20 mm, less than or equal to about 10 mm, less than or equal to about 8 mm, less than or equal to about 6 mm, less than or equal to about 4 mm, less than or equal to about 2 mm, or less. The length of the sub-channel may be bounded by the external length or width of the microfluidic device. The sub-channel may have the same cross-sectional dimension as the microchannel. Alternatively, the sub-channel may have different cross-sectional dimension than the microchannel. The sub-channel may have the same depth as the microchannel and a different cross-sectional dimension. Alternatively, the sub-channel may have the same cross-sectional dimension as the microchannel and a different depth. For example, the sub-channel may have a depth of less than or equal to about 500 µm, less than or equal to about 250 µm, less than or equal to about 100 µm, less than or equal to about 80 µm, less than or equal to about 60 µm, less than or equal to about 30 µm, less than or equal to about 15 µm, or less. The sub-channel may have a cross-section width of less than or equal to about 500 µm, less than or equal to about 250 µm, less than or equal to about 100 µm, less than or equal to about 75 µm, less than or equal to about 50 µm, less than or equal to about 40 µm, less than or equal to about 30 µm, less than or equal to about 20 µm, less than or equal to about 10 µm, or less.

In some examples, the cross-sectional dimensions of the sub-channel may be about 100 µm wide by about 100 µm deep. In some examples, the cross-sectional dimensions of the sub-channel may be about 100 µm wide by about 80 µm deep. In some examples, the cross-sectional dimensions of the sub-channel may be about 100 µm wide by about 60 µm deep. In some examples, the cross-sectional dimensions of the sub-channel may be about 100 µm wide by about 40 µm deep. In some examples, the cross-sectional dimensions of the sub-channel may be about 100 µm wide by about 20 µm deep. In some examples, the cross-sectional dimensions of the sub-channel may be about 100 µm wide by about 10 µm deep. In some examples, the cross-sectional dimensions of the sub-channel may be about 80 µm wide by about 100 µm deep. In some examples, the cross-sectional dimensions of the sub-channel may be about 60 µm wide by about 100 µm deep. In some examples, the cross-sectional dimensions of the sub-channel may be about 40 µm wide by about 100 µm deep. In some examples, the cross-sectional dimensions of the sub-channel may be about 20 µm wide by about 100 µm deep. In some examples, the cross-sectional dimensions of the sub-channel may be about 10 µm wide by about 100 µm deep. In some examples, the cross-sectional dimensions of the sub-channel may be about 80 µm wide by about 80 µm deep. In some examples, the cross-sectional dimensions of the sub-channel may be about 60 µm wide by about 60 µm deep. In some examples, the cross-sectional dimensions of the sub-channel may be about 40 µm wide by about 40 µm deep. In some examples, the cross-sectional dimensions of the sub-channel may be about 20 µm wide by about 20 µm deep. In some examples, the cross-sectional dimensions of the sub-channel may be about 10 µm wide by about 10 µm deep. The cross-sectional shape of the sub-channel may be any suitable cross-sectional shape including, but not limited to, circular, oval, triangular, square, or rectangular. The cross sectional shape of the sub-channel may be different than the cross-sectional shape of the microchannel. The cross-sectional shape of the sub-channel may be the same as the cross-sectional shape of the microchannel. The cross-sectional area of the sub-channel may be constant along the length of the sub-channel. Alternatively, or in addition, the cross-sectional area of the sub-channel may vary along the length of the microchannel. The cross-sectional area of the sub-channel may vary between about 50% and 150%, between about 60% and 125%, between about 70% and 120%, between about 80% and 115%, between about 90% and 110%, between about 95% and 100%, or between about 98% and 102%. The cross-sectional area of the sub-channel may be less than or equal to about 10,000 µm$^2$, less than or equal to about 7,500 µm$^2$, less than or equal to about 5,000 µm$^2$, less than or equal to about 2,500 µm$^2$, less than or equal to about 1,000 µm$^2$, less than or equal to about 750 µm$^2$, less than or equal to about 500 µm$^2$, less than or equal to about 400 µm$^2$, less than or equal to about 300 µm$^2$, less than or equal to about 200 µm$^2$, less than or equal to about 100 µm$^2$, or less. The cross-sectional area of the sub-channel may be the same as the cross-sectional area of the microchannel. The cross-sectional area of the sub-channel may be less than or equal to the area of the cross-sectional area of the microchannel. For example, the cross-sectional area of the sub-channel may be less than or equal to about 98%, less than or equal to about 95%, less than or equal to about 90%, less than or equal to about 85%, less than or equal to about 80%, less than or equal to about 75%, less than or equal to about 70%, less than or equal to about 60%, less than or equal to about 50%, less than or equal to about 40%, less than or equal to about 30%, less than or equal to about 20%, less than or equal to about 20%, or less of the cross-sectional area of the microchannel.

The lengths of the cross-channels may be constant. Alternatively, the lengths of the cross-channel may vary. The cross-channel may have a long dimension that is less than or equal to about 100 mm, less than or equal to about 75 mm, less than or equal to about 50 mm, less than or equal to about 40 mm, less than or equal to about 30 mm, less than or equal to about 20 mm, less than or equal to about 10 mm, less than or equal to about 8 mm, less than or equal to about 6 mm, less than or equal to about 4 mm, less than or equal to about 2 mm, or less. The length of the cross-channel may be bounded by the external length or width of the microfluidic device. The cross-channel may have the same cross-sectional dimension as the microchannel. Alternatively, the cross-channel may have a different cross-sectional dimension than the microchannel. The cross-channel may have the same depth as the microchannel and a different cross-sectional dimension. Alternatively, the cross-channel may have the same cross-sectional dimension as the microchannel and a different depth. For example, the cross-channel may have a depth of less than or equal to about 500 µm, less than or equal to about 250 µm, less than or equal to about 100 µm, less than or equal to about 80 µm, less than or equal to about 60 µm, less than or equal to about 30 µm, less than or equal to about 15 µm, or less. The cross-channel may have a cross-section width of less than or equal to about 500 µm, less than or equal to about 250 µm, less than or equal to about 100 µm, less than or equal to about 75 µm, less than or equal to about 50 µm, less than or equal to about 40 µm, less than or equal to about 30 µm, less than or equal to about 20 µm, less than or equal to about 10 µm, or less.

In some examples, the cross-sectional dimensions of the cross-channel may be about 100 µm wide by about 100 µm deep. In some examples, the cross-sectional dimensions of the cross-channel may be about 100 µm wide by about 80 µm deep. In some examples, the cross-sectional dimensions of the cross-channel may be about 100 µm wide by about 60 µm deep. In some examples, the cross-sectional dimensions of the cross-channel may be about 100 µm wide by about 40 µm deep. In some examples, the cross-sectional dimensions of the cross-channel may be about 100 μm wide by about 20 μm deep. In some examples, the cross-sectional dimensions of the cross-channel may be about 100 μm wide by about 10 μm deep. In some examples, the cross-sectional dimensions of the cross-channel may be about 80 μm wide by about 100 μm deep. In some examples, the cross-sectional dimensions of the cross-channel may be about 60 μm wide by about 100 μm deep. In some examples, the cross-sectional dimensions of the cross-channel may be about 40 μm wide by about 100 μm deep. In some examples, the cross-sectional dimensions of the cross-channel may be about 20 μm wide by about 100 μm deep. In some examples, the cross-sectional dimensions of the cross-channel may be about 10 μm wide by about 100 μm deep. In some examples, the cross-sectional dimensions of the cross-channel may be about 80 μm wide by about 80 μm deep. In some examples, the cross-sectional dimensions of the cross-channel may be about 60 μm wide by about 60 μm deep. In some examples, the cross-sectional dimensions of the cross-channel may be about 40 μm wide by about 40 μm deep. In some examples, the cross-sectional dimensions of the cross-channel may be about 20 μm wide by about 20 μm deep. In some examples, the cross-sectional dimensions of the cross-channel may be about 10 μm wide by about 10 μm deep.

The cross-sectional shape of the cross-channel may be any suitable cross-sectional shape including, but not limited to, circular, oval, triangular, square, or rectangular. The cross sectional shape of the cross-channel may be different than the cross-sectional shape of the microchannel. The cross-sectional shape of the cross-channel may be the same as the cross-sectional shape of the microchannel. The cross-sectional area of the cross-channel may be constant down the length of the cross-channel. Alternatively, or in addition, the cross-sectional area of the cross-channel may vary down the length of the microchannel. The cross-sectional area of the cross-channel may vary between about 50% and 150%, between about 60% and 125%, between about 70% and 120%, between about 80% and 115%, between about 90% and 110%, between about 95% and 100%, or between about 98% and 102%. The cross-sectional area of the cross-channel may be less than or equal to about 10,000 μm$^2$, less than or equal to about 7,500 μm$^2$, less than or equal to about 5,000 μm$^2$, less than or equal to about 2,500 μm$^2$, less than or equal to about 1,000 μm$^2$, less than or equal to about 750 μm$^2$, less than or equal to about 500 μm$^2$, less than or equal to about 400 μm$^2$, less than or equal to about 300 μm$^2$, less than or equal to about 200 μm$^2$, less than or equal to about 100 μm$^2$, or less. The cross-sectional area of the cross-channel may be the same as the cross-sectional area of the microchannel. Alternatively, the cross-sectional area of the cross-channel may be less than the area of the cross-sectional area of the microchannel. The cross-sectional area of cross-channel may be less than or equal to about 98%, less than or equal to about 95%, less than or equal to about 90%, less than or equal to about 85%, less than or equal to about 80%, less than or equal to about 75%, less than or equal to about 70%, less than or equal to about 60%, less than or equal to about 50%, less than or equal to about 40%, less than or equal to about 30%, less than or equal to about 20%, less than or equal to about 20%, or less of the cross-sectional area of the microchannel.

Method for Fabricating a Microfluidic Device

A microfluidic device useful in the methods and systems of the present disclosure may be fabricated through any useful method. For example, fabrication of the device may involve injection molding a thermoplastic to create a microfluidic structure. The microfluidic structure may comprise a microchannel, a plurality of microchambers, and a plurality of siphon apertures. The plurality of microchambers may be connected to the microchannel by the plurality of siphon apertures. The microchannel may comprise an inlet and an outlet. A thermoplastic thin film may be applied to cap the microfluidic structure. The thermoplastic thin film may be at least partially gas permeable when a pressure differential is applied across the thermoplastic thin film.

The thermoplastic thin film may be formed by injection molding. The thermoplastic thin film may be applied to the microfluidic structure by thermal bonding. Alternatively, or in addition, the thin film may be applied by chemical bonding. The thermoplastic thin film may be formed as part of and during the injection molding process to form the microfluidic device.

The body of the microfluidic device and the thin film may comprise the same materials. Alternatively, the body of the microfluidic device and the thin film may comprise different materials. The body of the microfluidic device and the thin film may comprise a thermoplastic. Examples of thermoplastics include, but are not limited to, cyclo-olefin polymers, acrylic, acrylonitrile butadiene styrene, nylon, polylactic acid, polybenzimidazole, polycarbonate, polyether sulfone, poly ether ether ketone, polyetherimide, polyethylene, polyphenylene oxide, polyphenylene sulfide, polypropylene, polystyrene, polyvinyl chloride, polytetrafluoroethylene, polyester, polyurethane or any derivative thereof. The microfluidic device may comprise homopolymers, copolymers, or a combination thereof. The microfluidic device may be formed of inelastic materials. Alternatively or in addition, the microfluidic device may be formed of elastic materials.

Both the thermoplastic and the thin film may be composed of a cyclo-olefin polymer. One suitable thermoplastic is Zeonor 1430R (Zeon Chemical, Japan) while one suitable thin film is Zeonox 1060R (Zeon Chemical, Japan). The thin film may comprise a material that is gas-impermeable at low pressure and at least partially gas permeable under pressure.

The inlet and the outlet of a microfluidic device of the present disclosure may be formed by mechanical drilling. Alternatively, the inlet and outlet are formed by melting, dissolving, or etching the thermoplastic.

Figure 4:
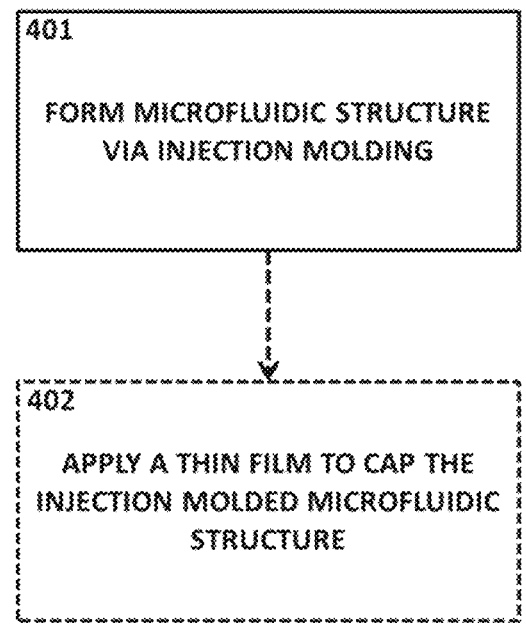
FIG. 4 schematically illustrates a method of manufacture of a microfluidic device.

FIG. 4 illustrates a method of manufacture of devices useful for sample processing and/or analysis. In FIG. 4, an injection molding process 401 is used to form a microfluidic structure. The microfluidic structure includes an array of microchambers, which are connected to at least one microchannel via siphon apertures, as shown in FIGS. 1A and 1B. The microfluidic structure is capped by a thin film. In the capping process, openings in at least one side of the microstructure are covered over in order to close and seal the microstructures. The capping may be performed by a process 402 of applying a thin film to the injection molded microfluidic structure. Alternatively, the capping may be performed by forming the thin film as part of the injection molding process 401.

As another example, while described in the context of a microstructure which is formed via injection molding, microfluidic devices formed by other microfabrication techniques may also benefit from the use of such a thin thermoplastic film to allow outgassing as described above. Such techniques include micromachining, microlithography, and hot embossing, as well as other microfabrication techniques.

The devices of the present disclosure may be consumable devices (e.g., designed for a single use, such as analysis and/or processing of a single sample) or reusable devices (e.g., designed for multiple uses, such as analysis and/or processing of multiple samples). The choices of materials for inclusion in the device may reflect whether the device will be used one or more times. For example, a consumable device may comprise materials that are less expensive than a reusable device. Similarly, manufacturing processes may be tailored to the use of the device. For example, a fabrication process for a consumable device may involve the production of less waste and/or involve fewer or cheaper steps. A reusable device may be cleanable and/or sterilizable to facilitate analyses and/or processing of multiple samples using the same device. For example, a reusable device may comprise materials capable of withstanding high temperatures appropriate for sterilization. A consumable device may or may not comprise such materials.

Method of Analyzing a Sample

In an aspect, the present disclosure provides methods for using a microfluidic device to analyze a sample, such as nucleic acid molecules. The nucleic acid molecules may be in or from a sample containing or suspected of containing a pathogen, such as a bacterium or bacteria. The method may comprise providing a microfluidic device as described herein. The device may comprise a microchannel. The microchannel may comprise an inlet and an outlet. The microfluidic device may further comprise a plurality of microchambers connected to the microchannel by a plurality of siphon apertures. The microfluidic device may be sealed by a thin film (e.g., a thermoplastic thin film) disposed adjacent to a surface of the microfluidic device such that the thin film caps the microchannel, the plurality of microchambers, and the plurality of siphon apertures. A reagent and/or sample may be applied to the inlet or the outlet. The microfluidic device may be filled by providing a first pressure differential between the reagent and/or sample and the microfluidic device, causing the reagent and/or sample to flow into the microfluidic device. The reagent and/or sample may be partitioned into the microchambers by applying a second pressure differential between the microchannel and the plurality of microchambers to move the reagent and/or sample into the plurality of microchambers and to force gas within the plurality of microchambers to pass through the thin film. The second pressure differential may be greater than the first pressure differential. A third pressure differential between the inlet and the outlet may be applied to introduce a fluid into the microchannel without introducing the fluid into the microchambers. The third pressure differential may be less than the second pressure differential. A reagent may be added before, after, or at the same time as a sample. A reagent may also be provided in one or more partitions of the device by another method. For example, a reagent may be deposited within one or more partitions prior to covering the one or more partitions with the thin film.

The inlet and the outlet of the device may be in fluid communication with a pneumatic pump or a vacuum system. The pneumatic pump or vacuum system may be a component of or separate from a system of the present disclosure. Filling and partitioning of a sample and/or reagent may be performed by applying pressure differentials across various features of the microfluidic device. Filling and partitioning of the sample and/or reagent may be performed without the use of valves between the microchambers and the microchannel to isolate sample and/or reagent. For example, filling of the microchannel may be performed by applying a pressure differential between the sample and/or reagent to be loaded and the microchannel. This pressure differential may be achieved by pressurizing the sample and/or reagent or by applying vacuum to the microchannel. Filling the microchambers may be performed by applying a pressure differential between the microchannel and the microchambers. This may be achieved by pressurizing the microchannel or by applying a vacuum to the microchambers. Partitioning the sample and/or reagent may be performed by applying a pressure differential between a fluid and the microchannel. This pressure differential may be achieved by pressurizing the fluid or by applying a vacuum to the microchannel.

The thin film may have different permeability characteristics under different applied pressure differentials. For example, the thin film may be gas impermeable at the first and third pressure differentials (e.g., low pressure), which may be smaller magnitude pressure differentials. The thin film may be at least partially gas permeable at the second pressure differential (e.g., high pressure), which may be a higher magnitude pressure differential. The first and third pressure differentials may be the same or they may be different. The first pressure differential may be the difference in pressure between the reagent in the inlet or outlet and the microfluidic device. During filling of the microfluidic device, the pressure of the reagent may be higher than the pressure of the microfluidic device. During filling of the microfluidic device, the pressure difference between the reagent and the microfluidic device (e.g., low pressure) may be less than or equal to about 8 pounds per square inch (psi), less than or equal to about 6 psi, less than or equal to about 4 psi, less than or equal to about 2 psi, less than or equal to about 1 psi, or less. In some examples, during filling of the microfluidic device, the pressure differential between the reagent and the microfluidic device may be from about 1 psi to about 8 psi. In some examples, during filling of the microfluidic device, the pressure differential between the reagent and the microfluidic device may be from about 1 psi to about 6 psi. In some examples, during filling of the microfluidic device, the pressure differential between the reagent and the microfluidic device may be from about 1 psi to about 4 psi. The microfluidic device may be filled by applying a pressure differential between the reagent and the microfluidic device for less than or equal to about 20 minutes, less than or equal to about 15 minutes, less than or equal to about 10 minutes, less than or equal to about 5 minutes, less than or equal to about 3 minutes, less than or equal to about 2 minutes, less than or equal about 1 minute, or less.

A filled microfluidic device may have sample or one or more reagents in the microchannel, siphon apertures, microchambers, or any combination thereof. Backfilling of the sample or the one or more reagents into the microchambers may occur upon filling of the microfluidic device or may occur during application of a second pressure differential. The second pressure differential (e.g., high pressure) may correspond to the difference in pressure between the microchannel and the plurality of microchambers. During application of the second pressure differential a first fluid in the higher pressure domain may push a second fluid in the lower pressure domain through the thin film and out of the microfluidic device. The first and second fluids may comprise a liquid or a gas. The liquid may comprise an aqueous mixture or an oil mixture. The second pressure differential may be achieved by pressurizing the microchannel. Alternatively, or in addition, the second pressure differentially may be achieved by applying a vacuum to the microchambers. During application of the second pressure differential, sample and/or reagent in the microchannel may flow into the microchambers. Additionally, during the application of the second pressure differential gas trapped within the siphon apertures, microchambers, and microchannel may outgas through the thin film. During backfilling and outgassing of the microchambers, the pressure differential between the microchambers and the microchannel may be greater than or equal to about 6 psi, greater than or equal to about 8 psi, greater than or equal to about 10 psi, greater than or equal to about 12 psi, greater than or equal to about 14 psi, greater than or equal to about 16 psi, greater than or equal to about 18 psi, greater than or equal to about 20 psi, or greater. In some examples, during backfilling of the microchambers, the pressure differential between the microchambers and the microchannel is from about 8 psi to about 20 psi. In some examples, during backfilling of the microchambers, the pressure differential between the microchambers and the microchannel is from about 8 psi to about 18 psi. In some examples, during backfilling of the microchambers, the pressure differential between the microchambers and the microchannel is from about 8 psi to about 16 psi. In some examples, during backfilling of the microchambers, the pressure differential between the microchambers and the microchannel is from about 8 psi to about 14 psi. In some examples, during backfilling of the microchambers, the pressure differential between the microchambers and the microchannel is from about 8 psi to about 12 psi. In some examples, during backfilling of the microchambers, the pressure differential between the microchambers and the microchannel is from about 8 psi to about 10 psi. The microchambers may be backfilled and outgassed by applying a pressure differential for more than about 5 minutes, more than about 10 minutes, more than about 15 minutes, more than about 20 minutes, more than about 25 minutes, more than about 30 minutes, or more.

The sample and/or reagent may be partitioned by removing the excess sample and/or reagent from the microchannel. Removing excess sample and/or reagent from the microchannel may prevent reagents and/or sample in one microchamber from diffusing through the siphon aperture into the microchannel and into other microchambers. Excess sample and/or reagent within the microchannel may be removed by introducing a fluid to the inlet or the outlet of the microchannel. The pressure of the fluid may be greater than the pressure of the microchannel, thereby creating a pressure differential between the fluid and the microchannel. The fluid may be oxygen, nitrogen, carbon dioxide, air, a noble gas, or any combination thereof. During partitioning of the sample, the pressure differential between the fluid and the microchannel may be less than or equal to about 8 psi, less than or equal to about 6 psi, less than or equal to about 4 psi, less than or equal to about 2 psi, less than or equal to about 1 psi, or less. In some examples, during partitioning of the sample and/or reagent, the pressure differential between the fluid and the microchannel may be from about 1 psi to about 8 psi. In some examples, during partitioning of the sample and/or reagent, the pressure differential between the fluid and the microchannel may be from about 1 psi to about 6 psi. In some examples, during partitioning of the sample and/or reagent, the pressure differential between the fluid and the microchannel may be from about 1 psi to about 4 psi. The sample and/or reagent may be partitioned by applying a pressure differential between the fluid and the microchannel for less than or equal to about 20 minutes, less than or equal to about 15 minutes, less than or equal to about 10 minutes, less than or equal to about 5 minutes, less than or equal to about 3 minutes, less than or equal to about 2 minutes, less than or equal to about 1 minute, or less.

Figure 3A:
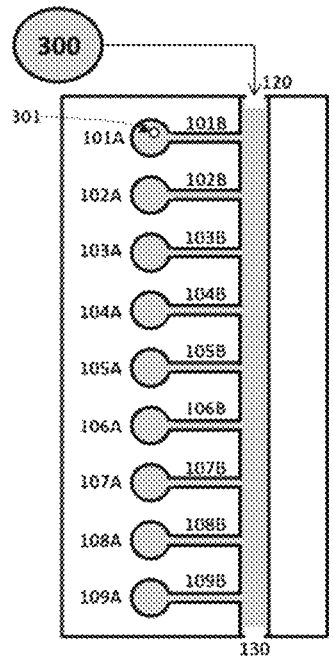
FIGS. 3A-3D show methods for use of an example microfluidic device.

FIGS. 3A-3D illustrate a method for use of the microfluidic device shown in FIG. 1A. In FIG. 3A, a low pressure is applied to reagent at the inlet 120 via a pneumatic pump 300 to force reagent into the microchannel 110 and thereby fill the microchambers via the siphon apertures. The pressure forces reagent to flow through the microchannel, and thereby to flow into the microchambers via the siphon apertures. At this time, gas bubbles such as bubble 301 may remain within the microchambers, siphon apertures, or microchannel. Filling via the application of low pressure may continue until the microchambers, siphon apertures, and microchannel are substantially filled with reagent. The reagent may be a reagent to be used in a polymerase chain reaction. The reagent may be diluted such that no more than one PCR template is present in the reagent per microchamber of the microfluidic device. For example, each partition of at least a subset of the plurality of partitions of a device may include at most one nucleic acid molecule. In some examples, each partition of a subset of the plurality of partitions of a device may include only one nucleic acid molecule.

Figure 3B:
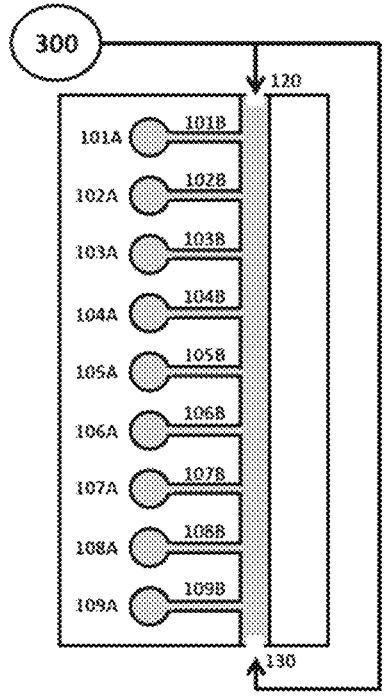

In FIG. 3B, the pneumatic pump 300 is connected to both inlets 120 and outlets 130 and a high pressure is applied. The high pressure is transmitted via the reagent and applied to gas bubbles such as bubble 301. Under the influence of this high pressure, thin film 150 becomes gas permeable, and the bubble 301 can outgas through the thin film 150. By applying this high pressure, the microchambers, siphon apertures, and microchannel can be rendered substantially free of gas bubbles, thereby avoiding fouling.

Figure 3C:
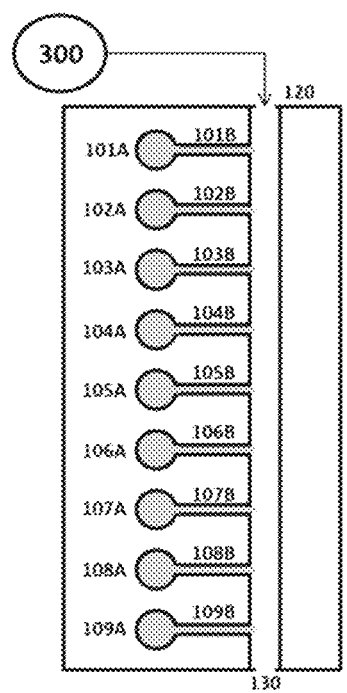

In FIG. 3C, fluid is reintroduced by applying low pressure to a gas at the inlet 120 via pneumatic pump 300. The air pressure may not be sufficient to allow the gas to outgas through the thin film or high enough to force gas bubbles into the siphon apertures and microchambers. Instead, the gas may clear the microchannel of reagent, leaving the reagent isolated in each microchamber and siphon aperture. The gas may be air. Alternatively, the gas may be an inert gas such as nitrogen, carbon dioxide, or a noble gas. Such a gas may be used to avoid reaction between the reagent and the component gases of air.

Figure 3D:
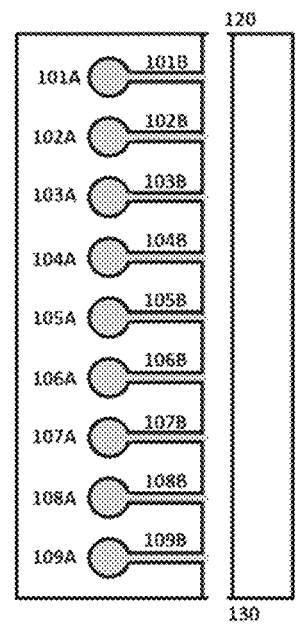

FIG. 3D illustrates the state of the system after the low pressure has been applied in FIG. 3C. After application of the low pressure gas the microchambers and siphon apertures may remain filled with reagent, while the microchannel may be cleared of reagent. The reagent may remain stationary within the microchambers due to the capillary force and high surface tension created by the siphon aperture. The capillary force and high surface tension may prevent the reagent from flowing into the microchannel and minimize reagent evaporation. A similar process to that described with regard to FIGS. 3A-3D may be used to partition sample within the device.

Partitioning of the sample may be verified by the presence of an indicator within the reagent. An indicator may include a molecule comprising a detectable moiety. The detectable moiety may include radioactive species, fluorescent labels, chemiluminescent labels, enzymatic labels, colorimetric labels, or any combination thereof. Non-limiting examples of radioactive species include $^3$H, $^{14}$C, $^{22}$Na, $^{32}$P, $^{33}$P, $^{35}$S, $^{42}$K, $^{45}$Ca, $^{59}$Fe, $^{123}$I, $^{124}$I, $^{125}$I, $^{131}$I, or $^{203}$Hg. Non-limiting examples of fluorescent labels include fluorescent proteins, optically active dyes (e.g., a fluorescent dye), organometallic fluorophores, or any combination thereof. Non-limiting examples of chemiluminescent labels include enzymes of the luciferase class such as Cypridina, Gaussia, Renilla, and Firefly luciferases. Non-limiting examples of enzymatic labels include horseradish peroxidase (HRP), alkaline phosphatase (AP), beta galactosidase, glucose oxidase, or other well-known labels.

An indicator molecule may be a fluorescent molecule. Fluorescent molecules may include fluorescent proteins, fluorescent dyes, and organometallic fluorophores. The indicator molecule may be a protein fluorophore. Protein fluorophores may include green fluorescent proteins (GFPs, fluorescent proteins that fluoresce in the green region of the spectrum, generally emitting light having a wavelength from 500-550 nanometers), cyan-fluorescent proteins (CFPs, fluorescent proteins that fluoresce in the cyan region of the spectrum, generally emitting light having a wavelength from 450-500 nanometers), red fluorescent proteins (RFPs, fluorescent proteins that fluoresce in the red region of the spectrum, generally emitting light having a wavelength from 600-650 nanometers). Non-limiting examples of protein fluorophores include mutants and spectral variants of AcGFP, AcGFP1, AmCyan, AmCyan1, AQ143, AsRed2, Azami Green, Azurite, BFP, Cerulean, CFP, CGFP, Citrine, copGFP, CyPet, dKeima-Tandem, DsRed, dsRed-Express, DsRed-Monomer, DsRed2, dTomato, dTomato-Tandem, EBFP, EBFP2, ECFP, EGFP, Emerald, EosFP, EYFP, GFP, HcRed-Tandem, HcRed1, JRed, Katuska, Kusabira Orange, Kusabira Orange2, mApple, mBanana, mCerulean, mCFP, mCherry, mCitrine, mECFP, mEmerald, mGrape1, mGrape2, mHoneydew, Midori-Ishi Cyan, mKeima, mKO, mOrange, mOrange2, mPlum, mRaspberry, mRFP1, mRuby, mStrawberry, mTagBFP, mTangerine, mTeal, mTomato, mTurquoise, mWasabi, PhiYFP, ReAsH, Sapphire, Superfolder GFP, T-Sapphire, TagCFP, TagGFP, TagRFP, TagRFP-T, TagYFP, tdTomato, Topaz, TurboGFP, Venus, YFP, YPet, ZsGreen, and ZsYellow1.

The indicator molecule may be a fluorescent dye. Non-limiting examples of fluorescent dyes include SYBR green; SYBR blue; DAPI; propidium iodine; Hoeste; SYBR gold; ethidium bromide; acridines; proflavine; acridine orange; acriflavine; fluorcoumanin; ellipticine; daunomycin; chloroquine; distamycin D; chromomycin; homidium; mithramycin; ruthenium polypyridyls; anthramycin; phenanthridines and acridines; propidium iodide; hexidium iodide; dihydroethidium; ethidium monoazide; ACMA; Hoechst 33258; Hoechst 33342; Hoechst 34580; DAPI; acridine orange; 7-AAD; actinomycin D; LDS751; hydroxystilbamidine; SYTOX Blue; SYTOX Green; SYTOX Orange; POPO-1; POPO-3; YOYO-1; YOYO-3; TOTO-1; TOTO-3; JOJO-1; LOLO-1; BOBO-1; BOBO-3; PO-PRO-1; PO-PRO-3; BO-PRO-1; BO-PRO-3; TO-PRO-1; TO-PRO-3; TO-PRO-5; JO-PRO-1; LO-PRO-1; YO-PRO-1; YO-PRO-3; PicoGreen; OliGreen; RiboGreen; SYBR Gold; SYBR Green I; SYBR Green II; SYBR DX; SYTO-40, SYTO-41, SYTO-42, SYTO-43, SYTO-44, and SYTO-45 (blue); SYTO-13, SYTO-16, SYTO-24, SYTO-21, SYTO-23, SYTO-12, SYTO-11, SYTO-20, SYTO-22, SYTO-15, SYTO-14, and SYTO-25 (green); SYTO-81, SYTO-80, SYTO-82, SYTO-83, SYTO-84, and SYTO-85 (orange); SYTO-64, SYTO-17, SYTO-59, SYTO-61, SYTO-62, SYTO-60, and SYTO-63 (red); fluorescein; fluorescein isothiocyanate (FITC); tetramethyl rhodamine isothiocyanate (TRITC); rhodamine; tetramethyl rhodamine; R-phycoerythrin; Cy-2; Cy-3; Cy-3.5; Cy-5; Cy5.5; Cy-7; Texas Red; Phar-Red; allophycocyanin (APC); Sybr Green I; Sybr Green II; Sybr Gold; CellTracker Green; 7-AAD; ethidium homodimer I; ethidium homodimer II; ethidium homodimer III; umbelliferone; eosin; green fluorescent protein; erythrosin; coumarin; methyl coumarin; pyrene; malachite green; stilbene; lucifer yellow; cascade blue; dichlorotriazinylamine fluorescein; dansyl chloride; fluorescent lanthanide complexes such as those including europium and terbium; carboxy tetrachloro fluorescein; 5 and/or 6-carboxy fluorescein (FAM); 5- (or 6-) iodoacetamidofluorescein; 5-{[2(and 3)-5-(Acetylmercapto)-succinyl]amino} fluorescein (SAMSA-fluorescein); lissamine rhodamine B sulfonyl chloride; 5 and/or 6 carboxy rhodamine (ROX); 7-amino-methyl-coumarin; 7-Amino-4-methylcoumarin-3-acetic acid (AMCA); BODIPY fluorophores; 8-methoxypyrene-1;3;6-trisulfonic acid trisodium salt; 3;6-Disulfonate-4-amino-naphthalimide; phycobiliproteins; AlexaFluor 350, 405, 430, 488, 532, 546, 555, 568, 594, 610, 633, 635, 647, 660, 680, 700, 750, and 790 dyes; DyLight 350, 405, 488, 550, 594, 633, 650, 680, 755, and 800 dyes; and other fluorophores.

The indicator molecule may be an organometallic fluorophore. Non-limiting examples of organometallic fluorophores include lanthanide ion chelates, non-limiting examples of which include tris(dibenzoylmethane) mono(1,10-phenanthroline)europium(lll), tris(dibenzoylmethane) mono(5-amino-1,10-phenanthroline)europium (lll), and Lumi4-Tb cryptate.

Signals may be collected (e.g., images taken) from the microfluidic device or a subset of the plurality of partitions (e.g., microchambers) thereof. Collecting signals may comprise taking images of the device or a subset of the plurality of partitions thereof. Signals (e.g., images) may be collected from single microchambers, an array of microchambers, or of multiple arrays of microchambers concurrently. Signals may be collected through the body of the microfluidic device, through the thin film of the microfluidic device, or both. The body of the microfluidic device may be substantially optically transparent. Alternatively, the body of the microfluidic device may be substantially optically opaque. Similarly, the thin film may be substantially optically transparent. Alternatively, the body of the microfluidic device may be substantially optically opaque.

Signals may be collected from the microfluidic device or a subset of the plurality of partitions thereof at any useful time and with any useful frequency. For example, signals (e.g., images) may be collected prior to filling of the microfluidic device with reagent or sample. Signals may also be collected during filling the microfluidic device with reagent or sample. Alternatively or in addition, signals may be collected after filling of the microfluidic device with reagent or sample. For example, signals may be collected to verify partitioning of the reagent or sample. Signals may also be collected during a reaction (e.g., a nucleic acid amplification reaction) to monitor products (e.g., amplification products) of the reaction. Similarly, signals may be collected during controlled heating of the device or a subset of the plurality of partitions thereof (e.g., during a high resolution melting analysis). Signals may be collected at specified intervals, such as at specified time points. Alternatively, or in addition, a video may be taken of the microfluidic device or a subset of the plurality of partitions thereof. The specified intervals may include collecting a signal (e.g., taking an image) at least every 300 seconds, at least every 240 seconds, at least every 180 seconds, at least every 120 seconds, at least every 90 seconds, at least every 60 seconds, at least every 30 seconds, at least every 15 seconds, at least every 10 seconds, at least every 5 seconds, at least every 4 seconds, at least every 3 seconds, at least every 2 seconds, at least every 1 second, or more frequently during a reaction. Signals may also be collected in response to instructions from a processor, as described herein.

The methods described herein involving the use of a microfluidic device may comprise amplification of a plurality of nucleic acid molecules from a sample. The microfluidic device may be filled with one or more amplification reagents such as nucleic acid molecules, components necessary for an amplification reaction (e.g., primers, polymerases, and deoxyribonucleotides), an indicator molecule, and an amplification probe. Amplification reactions may involve thermal cycling the plurality of microchambers or a subset thereof, as described herein. Detection of nucleic acid amplification may be performed by collecting signals from (e.g., imaging) the plurality of microchambers of the microfluidic device or a subset thereof. Nucleic acid molecules may be quantified by counting the microchambers in which the nucleic acid molecules are successfully amplified and applying Poisson statistics. Nucleic acid molecules may also be quantified by processing signals collected at different time points throughout an amplification reaction. For example, one or more signals may be collected during each thermal cycle (e.g., each amplification cycle) of a nucleic acid amplification reaction and the signals can be used to determine an amplification rate as in, e.g., real-time or quantitative polymerase chain reaction (real-time PCR or qPCR). Nucleic acid amplification and quantification may be performed in a single integrated unit, e.g., within a given partition or a subset of the plurality of partitions of the device.

A variety of nucleic acid amplification reactions may be used to amplify the nucleic acid molecule in a sample to generate an amplified product. Amplification of a nucleic acid target may be linear, exponential, or a combination thereof. Non-limiting examples of nucleic acid amplification methods include primer extension, polymerase chain reaction, reverse transcription, isothermal amplification, ligase chain reaction, helicase-dependent amplification, asymmetric amplification, rolling circle amplification, and multiple displacement amplification The amplification product of an amplification reaction may be DNA or RNA. For samples including DNA molecules, any DNA amplification method may be employed. DNA amplification methods include, but are not limited to, PCR, real-time PCR, assembly PCR, asymmetric PCR, digital PCR, dial-out PCR, helicase-dependent PCR, nested PCR, hot start PCR, inverse PCR, methylation-specific PCR, miniprimer PCR, multiplex PCR, overlap-extension PCR, thermal asymmetric interlaced PCR, touchdown PCR, and ligase chain reaction. DNA amplification may be linear, exponential, or any combination thereof. DNA amplification may also be achieved with digital PCR (dPCR), real-time quantitative PCR (qPCR), or quantitative digital PCR (qdPCR), as described herein.

Reagents necessary for nucleic acid amplification may include polymerizing enzymes, reverse primers, forward primers, and amplification probes. Examples of polymerizing enzymes include, without limitation, nucleic acid polymerase, transcriptase, or ligase (i.e., enzymes which catalyze the formation of a bond). The polymerizing enzyme can be naturally occurring or synthesized. Examples of polymerases include a DNA polymerase, and RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof. For a Hot Start polymerase, a denaturation step at a temperature from about 92° C. to 95° C. for a time period from about 2 minutes to 10 minutes may be required.

A nucleic acid amplification reaction may involve an amplification probe. An amplification probe may be a sequence-specific oligonucleotide probe. The amplification probe may be optically active when hybridized with an amplification product. The amplification probe may only be detectable as nucleic acid amplification progresses. The intensity of a signal collected from a plurality of partitions including nucleic acid molecules (e.g., optical signal) may be proportional to the amount of amplified product included in the partitions. For example, the signal collected from a particular partition may be proportional to the amount of amplified product in that particular partition. A probe may be linked to any of the optically-active detectable moieties (e.g., dyes) described herein and may also include a quencher capable of blocking the optical activity of an associated dye. Non-limiting examples of probes that may be useful as detectable moieties include TaqMan probes, TaqMan Tamara probes, TaqMan MGB probes, Lion probes, locked nucleic acid probes, or molecular beacons. Non-limiting examples of quenchers that may be useful in blocking the optical activity of the probe include Black Hole Quenchers (BHQ), Iowa Black FQ and RQ quenchers, or Internal ZEN Quenchers. Alternatively or in addition, the probe or quencher may be any known probe that is useful in the context of the methods of the present disclosure.

The amplification probe may be a dual labeled fluorescent probe. The dual labeled probe may include a fluorescent reporter and a fluorescent quencher linked with a nucleic acid. The fluorescent reporter and fluorescent quencher may be positioned in close proximity to each other. The close proximity of the fluorescent reporter and fluorescent quencher may block the optical activity of the fluorescent reporter. The dual labeled probe may bind to the nucleic acid molecule to be amplified. During amplification, the fluorescent reporter and fluorescent quencher may be cleaved by the exonuclease activity of the polymerase. Cleaving the fluorescent reporter and quencher from the amplification probe may cause the fluorescent reporter to regain its optical activity and enable detection. The dual labeled fluorescent probe may include a 5' fluorescent reporter with an excitation wavelength maximum of about 450 nanometers (nm), 500 nm, 525 nm, 550 nm, 575 nm, 600 nm, 625 nm, 650 nm, 675 nm, 700 nm, or higher and an emission wavelength maximum of about 500 nm, 525 nm, 550 nm, 575 nm, 600 nm, 625 nm, 650 nm, 675 nm, 700 nm, or higher. The dual labeled fluorescent probe may also include a 3' fluorescent quencher. The fluorescent quencher may quench fluorescent emission wavelengths between about 380 nm and 550 nm, 390 nm and 625 nm, 470 nm and 560 nm, 480 nm and 580 nm, 550 nm and 650 nm, 550 nm and 750 nm, or 620 nm and 730 nm.

Nucleic acid amplification reactions carried out within microchambers of the device may comprise thermal cycling the microchambers of the microfluidic device, or a subset thereof. Thermal cycling may include controlling the temperature of the microfluidic device by applying heating or cooling to the microfluidic device. Heating or cooling methods may include resistive heating or cooling, radiative heating or cooling, conductive heating or cooling, convective heating or cooling, or any combination thereof. Thermal cycling may include cycles of incubating the microchambers at a temperature sufficiently high to denature nucleic acid molecules for a duration followed by incubation of the microchambers at an extension temperature for an extension duration. Thermal cycling may also include cycles of incubating the microchambers at a temperature sufficient for annealing a primer to a nucleic acid molecule at an annealing temperature for an annealing duration. Denaturation temperatures may vary depending upon, for example, the particular nucleic acid sample, the reagents used, and the desired reaction conditions. A denaturation temperature may be from about 80° C. to about 110° C. A denaturation temperature may be from about 85° C. to about 105° C. A denaturation temperature may be from about 90° C. to about 100° C. A denaturation temperature may be from about 90° C. to about 98° C. A denaturation temperature may be from about 92° C. to about 95° C. A denaturation temperature may be at least about 80° C., at least about 81° C., at least about 82° C., at least about 83° C., at least about 84° C., at least about 85° C., at least about 86° C., at least about 87° C., at least about 88° C., at least about 89° C., at least about 90° C., at least about 91° C., at least about 92° C., at least about 93° C., at least about 94° C., at least about 95° C., at least about 96° C., at least about 97° C., at least about 98° C., at least about 99° C., at least about 100° C., or higher.

The duration for denaturation may vary depending upon, for example, the particular nucleic acid sample, the reagents used, and the desired reaction conditions. The duration for denaturation may be less than or equal to about 300 seconds, 240 seconds, 180 seconds, 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second. Alternatively, the duration for denaturation may be no more than about 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second.

Extension temperatures may vary depending upon, for example, the particular nucleic acid sample, the reagents used, and the desired reaction conditions. An extension temperature may be from about 30° C. to about 80° C. An extension temperature may be from about 35° C. to about 75° C. An extension temperature may be from about 45° C. to about 65° C. An extension temperature may be from about 55° C. to about 65° C. An extension temperature may be from about 40° C. to about 60° C. An extension temperature may be at least about 35° C., at least about 36° C., at least about 37° C., at least about 38° C., at least about 39° C., at least about 40° C., at least about 41° C., at least about 42° C., at least about 43° C., at least about 44° C., at least about 45° C., at least about 46° C., at least about 47° C., at least about 48° C., at least about 49° C., at least about 50° C., at least about 51° C., at least about 52° C., at least about 53° C., at least about 54° C., at least about 55° C., at least about 56° C., at least about 57° C., at least about 58° C., at least about 59° C., at least about 60° C., at least about 61° C., at least about 62° C., at least about 63° C., at least about 64° C., at least about 65° C., at least about 66° C., at least about 67° C., at least about 68° C., at least about 69° C., at least about 70° C., at least about 71° C., at least about 72° C., at least about 73° C., at least about 74° C., at least about 75° C., at least about 76° C., at least about 77° C., at least about 78° C., at least about 79° C., or at least about 80° C.

Extension time may vary depending upon, for example, the particular nucleic acid sample, the reagents used, and the desired reaction conditions. The duration for extension may be less than or equal to about 300 seconds, 240 seconds, 180 seconds, 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second. Alternatively, the duration for extension may be no more than about 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second.

Annealing temperatures may vary depending upon, for example, the particular nucleic acid sample, the reagents used, and the desired reaction conditions. An annealing temperature may be from about 30° C. to about 80° C. An annealing temperature may be from about 35° C. to about 75° C. An annealing temperature may be from about 45° C. to about 65° C. An annealing temperature may be from about 55° C. to about 65° C. An annealing temperature may be from about 40° C. to about 60° C. An annealing temperature may be at least about 35° C., at least about 36° C., at least about 37° C., at least about 38° C., at least about 39° C., at least about 40° C., at least about 41° C., at least about 42° C., at least about 43° C., at least about 44° C., at least about 45° C., at least about 46° C., at least about 47° C., at least about 48° C., at least about 49° C., at least about 50° C., at least about 51° C., at least about 52° C., at least about 53° C., at least about 54° C., at least about 55° C., at least about 56° C., at least about 57° C., at least about 58° C., at least about 59° C., at least about 60° C., at least about 61° C., at least about 62° C., at least about 63° C., at least about 64° C., at least about 65° C., at least about 66° C., at least about 67° C., at least about 68° C., at least about 69° C., at least about 70° C., at least about 71° C., at least about 72° C., at least about 73° C., at least about 74° C., at least about 75° C., at least about 76° C., at least about 77° C., at least about 78° C., at least about 79° C., or at least about 80° C.

Annealing time may vary depending upon, for example, the particular nucleic acid sample, the reagents used, and the desired reaction conditions. The duration for annealing may be less than or equal to about 300 seconds, 240 seconds, 180 seconds, 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second. Alternatively, the duration for annealing may be no more than about 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second.

Nucleic acid amplification may include multiple cycles of thermal cycling (e.g., multiple amplification cycles). Any suitable number of cycles may be performed. The number of cycles performed may be more than about 5, more than about 10, more than about 15, more than about 20, more than about 30, more than about 40, more than about 50, more than about 60, more than about 70, more than about 80, more than about 90, more than about 100 cycles, or more. The number of cycles performed may depend upon the number of cycles necessary to obtain detectable amplification products. For example, the number of cycles necessary to detect nucleic acid amplification during PCR (e.g., dPCR, qPCR, or qdPCR) may be less than or equal to about 100, less than or equal to about 90, less than or equal to about 80, less than or equal to about 70, less than or equal to about 60, less than or equal to about 50, less than or equal to about 40, less than or equal to about 30, less than or equal to about 20, less than or equal to about 15, less than or equal to about 10, less than or equal to about 5 cycles, or less.

The time to reach a detectable amount of amplification product may vary depending upon, for example, the particular nucleic acid sample, the reagents used, the amplification reaction used, the number of amplification cycles used, and the desired reaction conditions. The time to reach a detectable amount of amplification product may be about 120 minutes or less, 90 minutes or less, 60 minutes or less, 50 minutes or less, 40 minutes or less, 30 minutes or less, 20 minutes or less, 10 minutes or less, or 5 minutes or less.

The ramping rate (i.e., the rate at which the microchamber transitions from one temperature to another) is important for amplification. For example, the temperature and time for which an amplification reaction yields a detectable amount of amplified product may vary depending upon the ramping rate. The ramping rate may impact the time(s), temperature(s), or both the time(s) and temperature(s) used during amplification. The ramping rate may be constant between cycles or may vary between cycles. The ramping rate may be adjusted based on the sample being processed. For example, optimum ramping rate(s) may be selected to provide a robust and efficient amplification method.

Figure 5:
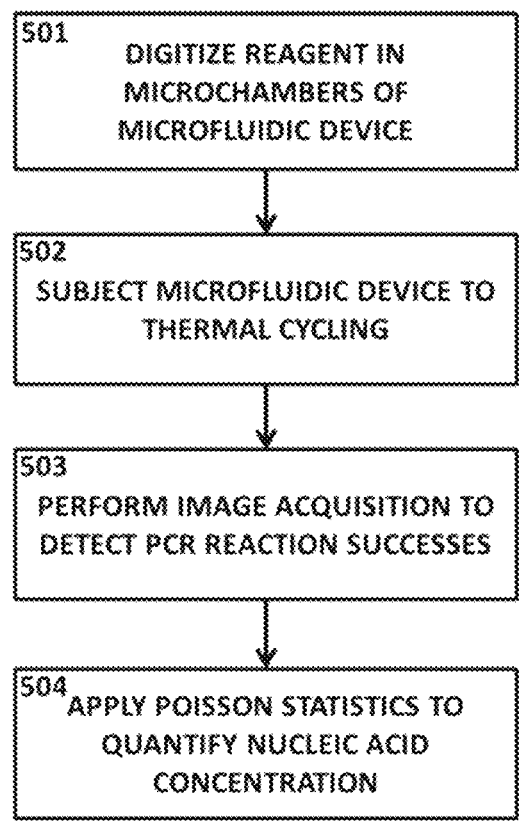
FIG. 5 schematically illustrates an exemplary digital PCR process to be employed with the a microfluidic device.

FIG. 5 illustrates a digital PCR process to be employed with the above-described microfluidic device. In step 501, reagent is partitioned as shown in FIGS. 3A-3D. In step 502, the reagent is subjected to thermal cycling to run the PCR reaction on the reagent in the microchambers. This step may be performed, for example, using a flat block thermal cycler. In step 503, image acquisition is performed to determine which microchambers have successfully run the PCR reaction. Image acquisition may, for example, be performed using a three color probe detection unit. In step 504, Poisson statistics are applied to the count of microchambers determined in step 503 to convert the raw number of positive chambers into a nucleic acid concentration.

A method for analyzing a plurality of nucleic acid molecules may comprise providing a device comprising a plurality of partitions as described herein. At least a subset of the plurality of partitions may include a plurality of nucleic acid molecules (e.g., deoxyribonucleic acid or ribonucleic acid molecules). Each partition of the subset of the plurality of partitions may be configured to permit gas flow from the partitions to an environment external to the partitions through at least one barrier separating the partitions from the external environment. The subset of the plurality of partitions may then be subjected to conditions sufficient to conduct nucleic acid amplification reactions using the plurality of nucleic acid molecules to generate amplification products from at least a subset of the plurality of nucleic acid molecules. While the subset of plurality of partitions is subjected to these conditions, signals may be collected from the subset of the plurality of partitions over a plurality of time points. Signals collected from the plurality of partitions may then be processed to determine a number of nucleic acid molecules in the subset of the plurality of partitions. Signal processing may take place while amplification reactions are in progress or after amplification reactions have completed.

Subjecting the subset of the plurality of partitions to conditions sufficient to conduct nucleic acid amplification reactions may comprise thermal cycling, as described herein. Thermal cycling may comprise a denaturation phase, an extension phase, and an annealing phase and may involve any useful combination of temperature and durations. Any useful number of thermal cycles may be performed. For example, if signal is being processed while amplification reactions are ongoing, a processor controlling the thermal cycling process may reach a threshold after which thermal cycling is programmed to cease. Alternatively, a user may interact with a system carrying out the amplification and signal collection processes and select to end thermal cycling after a given number of cycles. Thermal cycling may be performed using a flat block thermal cycler or any other useful temperature-control device.

Collecting signals from the subset of plurality of partitions may involve collecting more than one signal per partition per thermal cycle. For example, signal may be collected during each annealing phase, during each extension phase, during each denaturation phase, or any combination thereof. Alternatively, a system carrying out the method may be programmed to collect signal at a plurality of pre-determined time points. These time points may be evenly spaced (e.g., every 5 seconds) or according to a predetermined pattern (e.g., every 5 seconds for the first 100 seconds followed by every 20 seconds, or any other useful pattern). As described herein, collecting signals may comprise imaging. A detector may be configured to image all of the subset of the plurality of partitions of the device simultaneously. A detector for imaging may detect fluorescence emission at two or more wavelengths. Such a detector may be capable of measuring nucleic acid amplification products corresponding to different starting nucleic acid molecules (e.g., templates). For example, a sample including two different nucleic acid molecules may be exposed to two different primers, each of which includes a different detectable label (e.g., a dye or fluorescent probe) and is specific to a different nucleic acid molecule. The different detectable labels may emit fluorescence signal at different wavelengths, each of which may be detectable by the same detector. Determining a number of nucleic acid molecules in the subset of the plurality of partitions may involve determining an optical intensity for each partition that is proportional to the amount of amplification products in each partition.

Nucleic acid amplification reactions may involve one or more reagents, as described herein. For example, reagents such as primers, deoxyribonucleotides, buffers, co-factors, intercalating dyes, and polymerases may be used. These reagents may be loaded into the device before, after, or at the same time the sample is loaded into the device. The plurality of nucleic acid molecules may be loaded into the plurality of partitions of the device using controlled fluid flow (e.g., as described with regard to FIGS. 3A-3D). Gas in the subset of the plurality of partitions may be subjected to flow from the partitions to the external environment. For example, loading the device or a subset of the plurality of partitions thereof with sample including nucleic acid molecules may cause outgassing from the partitions through the barrier, as described herein.

The device used in a method of analyzing nucleic acid molecule may have any features described herein. The barrier of the device may comprise a polymeric material, such as a thermoplastic material, and may be a thin film. The barrier may be substantially optically transparent. The barrier may have a thickness from about 50 μm to about 200 μm (e.g., about 50 μm, 100 μm, 150 μm, or 200 μm). The device may comprise at least one microchannel comprising at least one inlet and at least one outlet and a plurality of siphon apertures. The subset of the plurality of partitions may be in fluid communication with the microchannel by the plurality of siphon apertures. The plurality of partitions may include from about 1,000 to about 20,000 partitions (e.g., at least about 1,000, 1,500, 2,000, 2,500, 3,000, 3,500, 4,000, 4,500, 5,000, 10,000, 15,000, or 20,000 partitions).

Figures 11A, 11B, 11C:
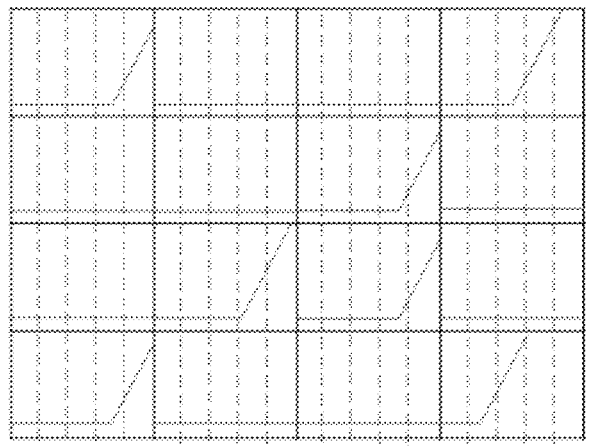
FIGS. 11A-11C show representations of a quantitative digital polymerase chain reaction (qdPCR) process.

FIG. 11 illustrates a quantitative digital PCR process to be employed with the above-described microfluidic device. FIG. 11A shows a representation of a subset of partitions of an exemplary microfluidic device. In certain partitions, no nucleic acid templates are present; in other partitions, one or more templates are present. FIG. 11B illustrates the amplification dynamics of the samples in each partition of the exemplary device. As illustrated in FIG. 11B, partitions with different numbers of nucleic acid templates present exhibit different amplification dynamics. Partitions with no templates do not amplify. Otherwise, partitions amplify faster if they have more templates present compared to other partitions. Each dashed vertical line represents a single amplification cycle for a total of five amplification cycles. While five cycles are illustrated, any number of cycles may be performed, depending on the specific features of the method and/or configuration of the system. For example, the number of nucleic acid molecules that may potentially be present in any given partition, the reagents used, and other reaction conditions may affect the required number of cycles, as more cycles may be required to provide an absolute quantification when a wider range of number of templates is potentially present in any given partition. FIG. 11C illustrates the results of a qdPCR process applied to the amplification dynamics shown in FIG. 11B. Specifically, FIG. 11C illustrates the number of nucleic acid templates calculated to exist in each partition based on the amplification dynamics measured during the five PCR amplification cycles shown in FIG. 11B.

Figure 16:
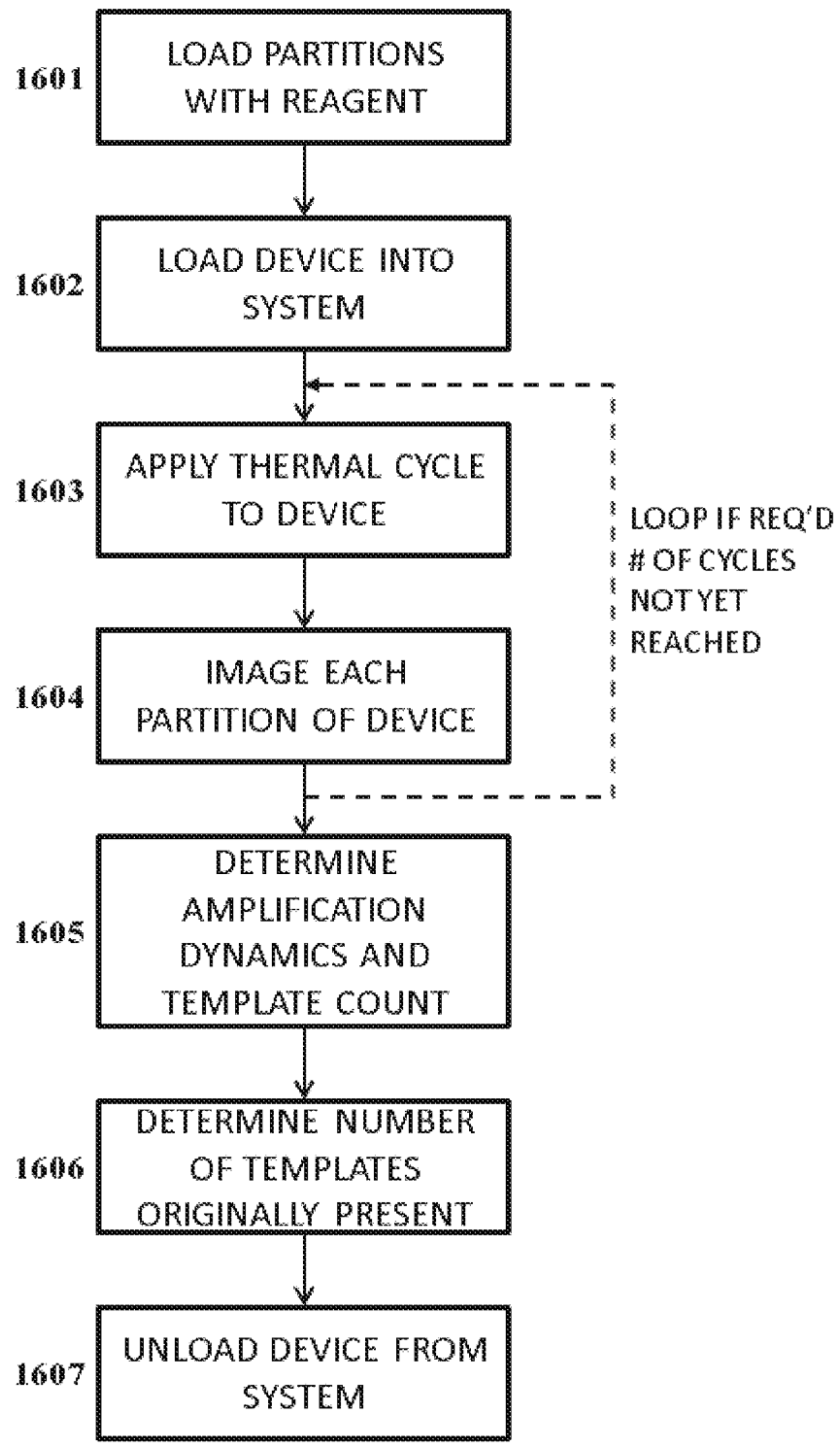
FIG. 16 illustrates a method of performing qdPCR for sample processing and/or analysis.

FIG. 16 illustrates a method of performing qdPCR using a device described herein. In step 1601, the plurality of partitions of the device, or a subset thereof, are loaded with one or more reagents. Loading of reagents and/or sample may be performed, e.g., as described herein. In some cases, reagents may be placed in the partitions or another portion of the device (e.g., using an automated mechanical process) prior to placement of a thin film over the partitions (e.g., sealing of the device). For example, a reagent packet, blister pack, gel, or other such component may be deposited in a partition prior to sealing the device. Sample including a plurality of nucleic acid molecules may also be added, as described herein.

In step 1602, the device may be loaded into a system for performing qdPCR. For example, the device may be physically placed onto a thermal unit such as a heating block and clamped in place with a pneumatic clamping device or placed in a slot, groove, or depression in a housing of an analytical system. Registration marks and/or mechanical keys may facilitate placement of the device. The device may be loaded into a mechanical loading unit that queues devices for placement and analysis in a serialized order. In some cases, step 1602 is performed before step 1601 and reagent is loaded into the device after the device has been placed within an analytical system. Such a system may comprise a fluid flow unit and/or other mechanical and fluid components including reservoirs, pumps, valves, and meters, as described herein, for loading a device with reagent.

In step 1603, nucleic acid amplification reactions are performed using the plurality of nucleic acids loaded into a subset of the plurality of partitions of the device, or a subset thereof. Amplification reactions may involve one or more thermal cycles, as described herein. For example, a PCR amplification reaction may involve a denaturation phase, an annealing phase, and an extension phase An amplification cycle may last between about 60 and 180 seconds (e.g., about 150 seconds, with 30 seconds at a denaturing temperature and 120 seconds at an annealing/extension temperature). Additional steps and/or different durations may also be employed.

In step 1604, signals are collected from each partition in the subset of the plurality of partitions of the device. For example, images may be taken of the partitions and optical signal measured. Imaging may be performed by, for example, moving an optical unit to scan the thermal unit, by moving the thermal unit to scan the optical unit, or by moving both optical and thermal unit to allow imaging of the device or a subset of the plurality of partitions thereof. Signal of the entire device may be collected at once (e.g., using one or more detectors, such as one or more cameras, or using a single detector configured to collect signal from the entire device at once) or signal may be collected from only a portion of the device at one time (e.g., corresponding to a subset of the plurality of partitions of the device). In the former case, scanning of a thermal unit and/or a detector may not be required. Signals may be collected one or more times during amplification to, for example, provide an estimate of amplification dynamics during each cycle. In some cases, signal may only be collected once after each amplification cycle in order to determine the amount of amplification that has taken place after completion of the amplification cycle. Collecting signals may comprise imaging a subset of the plurality of partitions of the device. Imaging may be performed using a fluorescent dye that intercalates with double-stranded nucleic acids, or by employing quenched DNA probes that fluoresce only after reacting with a complementary sequence. In either case, imaging may be performed by illuminating the partitions with an excitation light source suitable for the fluorescent probes and determining which partitions fluoresce and the strength of fluorescence. In some cases, steps 1603 and 1604 may be performed in parallel, with signals being collected (e.g., imaging) during nucleic acid amplification reactions (e.g., thermal cycling).

In step 1605, the amplification dynamics in each partition of the subset of the plurality of partitions of the device are determined based on the signals collected in steps 1604. By determining an amplification rate, the original number of nucleic acid molecules included in each partition of the subset of the plurality of partitions can be estimated. For example, in FIG. 11B, amplification dynamics for an array of partitions are shown corresponding to five amplification cycles. The number of nucleic acid molecules corresponding to each partition in the array are shown in FIG. 11C and may be determined by, for example, measuring an amount of fluorescence over a background level and relating it to a number of nucleic acid molecules (e.g., templates). In such an example, a partition that originally included more nucleic acid molecules will amplify more rapidly and thus produce detectable fluorescence earlier. The earlier the time (e.g., amplification cycle) at which fluorescence becomes detectable, the more templates were originally present in the partition. Accordingly, the number of nucleic acid molecules present may be determined by the number of cycles completed or remaining when the fluorescence first becomes detectable. Other methods of determining the amplification dynamics may also be applied. In each, the ultimate determination is a number of templates originally present in each partition based on the amount of signal collected, the timing at which the signal is detected, and/or the rate of increase of signal production.

In step 1606, a total number of nucleic acid molecules present in a subset of the plurality of partitions of the device is determined by summing the number of nucleic acid molecules originally present in each partition of the subset of the plurality of partitions.

In step 1607, the device is unloaded from the system for performing qdPCR. Unloading (e.g., removing) the device may comprise a mirror of the loading procedure of step 1601 or a different procedure. For example, a manually loaded device may be automatically unloaded by a mechanical loading unit, or may be unloaded in other ways (e.g., by a vacuum pick and place system). The process may then be repeated with another device.

Methods for Thermodynamic Analysis of a Nucleic Acid Sample

The present disclosure provides methods for thermodynamic analysis of a sample. For example, a device described herein may be used for a high resolution melting (HRM) analysis. A method for analyzing a plurality of nucleic acid molecules may comprise providing a device comprising a plurality of partitions as described herein. At least a subset of the plurality of partitions may include a plurality of nucleic acid molecules (e.g., deoxyribonucleic acid or ribonucleic acid molecules). Each partition of the subset of the plurality of partitions may be configured to permit gas flow from the partitions to an environment external to the partitions through at least one barrier separating the partitions from the external environment. The subset of the plurality of partitions may then be subjected to controlled heating. While the subset of the plurality of partitions is subjected to these conditions, signals may be collected from the subset of the plurality of partitions, e.g., over a plurality of time points. Signals collected from the plurality of partitions may then be processed to yield data indicative of a melting point of at least a subset of the plurality of nucleic acid molecules in the subset of the plurality of partitions. Signal processing may take place while controlled heating is in progress or after the controlled heating has completed.

The method may further comprise performing nucleic acid amplification reactions (e.g., as described herein) on a nucleic acid sample under conditions sufficient to yield the plurality of nucleic acid molecules as amplification products of the nucleic acid sample. Amplification reactions may be performed in the subset of the plurality of partitions. For example, the sample including nucleic acid molecules may be loaded into the subset of the plurality of partitions prior to performing the nucleic acid amplification reactions. Performing an amplification reaction may comprise heating the subset of the plurality of partitions using the same thermal unit (e.g., heater) used to perform controlled heating of the subset of the plurality of partitions. Amplification reactions may involve one or more reagents such as one or more primers, deoxyribonucleotides, buffers, co-factors, intercalating dyes, and polymerases, or any combination thereof. A reagent may include a detectable label such as a fluorophore or a fluorescent label. In some instances, it may be useful to contact at least a subset of the nucleic acid molecules of the nucleic acid sample with an intercalating dye prior to performing amplification reactions.

Controlled heating of a subset of the plurality of partitions of a device may be performed at any useful rate and over any useful temperature range. For example, controlled heating may be performed from a lower temperature of at least about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C., or more. Controlled heating may be performed to an upper temperature of at least about 35° C., about 40° C., about 45° C., about 50° C., about 55° C., about 60° C., about 65° C., about 70° C., about 75° C., about 80° C., about 85° C., about 90° C., about 91° C., about 92° C., about 93° C., about 94° C., about 95° C., about 96° C., about 97° C., about 98° C., about 99° C., or about 100° C., or more. Temperature may be increased by any useful increment. For example, temperature may be increased by at least about 0.01° C., about 0.05° C., about 0.1° C., about 0.2° C., about 0.3° C., about 0.4° C., about 0.5° C., about 1° C., about 2° C., about 3° C., about 4° C., about 5° C., or about 10° C., or more. Controlled heating may also occur over unevenly spaced temperature increments. For example, temperature may be increased by about 0.1° C. over a range where significant melting of a nucleic acid molecule is expected (e.g., fine grain measurement) and by about 1° C. over a range where no significant melting of a nucleic acid molecule is expected (e.g., coarse grain measurement). Controlled heating may be performed at any useful rate such as at least about 0.0001° C./second, about 0.0002° C./second, about 0.0003° C./second, about 0.0004° C./second, about 0.0005° C./second, about 0.0006° C./second, about 0.0007° C./second, about 0.0008° C./second, about 0.0009° C./second, about 0.001° C./second, about 0.002° C./second, about 0.003° C./second, about 0.004° C./second, about 0.005° C./second, about 0.006° C./second, about 0.007° C./second, about 0.008° C./second, about 0.009° C./second, about 0.01° C./second, about 0.02° C./second, about 0.03° C./second, about 0.04° C./second, about 0.05° C./second, about 0.06° C./second, about 0.07° C./second, about 0.08° C./second, about 0.09° C./second, about 0.1° C./second, about 0.2° C./second, about 0.3° C./second, about 0.4° C./second, about 0.5° C./second, about 0.6° C./second, about 0.7° C./second, about 0.8° C./second, about 0.9° C./second, about 1° C./second, about 2° C./second, about 3° C./second, about 4° C./second, and about 5° C./second, or more. A thermal unit (e.g., a heater) carrying out the controlled heating process may maintain a given temperature for any useful duration. For example, a given temperature may be maintained for at least about 1 second, about 2 seconds, about 3 seconds, about 4 seconds, about 5 seconds, about 6 seconds, about 7 seconds, about 8 seconds, about 9 seconds, about 10 seconds, about 15 seconds, about 20 seconds, about 25 seconds, about 30 seconds, about 45 seconds, about 60 seconds, about 70 seconds, about 80 seconds, about 90 seconds, about 100 seconds, about 110 seconds, about 120 seconds, about 130 seconds, about 140 seconds, about 150 seconds, about 160 seconds, about 170 seconds, about 180 seconds, about 190 seconds, about 200 seconds, about 210 seconds, about 220 seconds, about 230 seconds, about 240 seconds, about 250 seconds or about 300 seconds, or more.

Signals may be collected from the subset of the plurality of partitions at any desired time points. For example, signal may be collected at least about every 1 second, about every 2 seconds, about every 3 seconds, about every 4 seconds, about every 5 seconds, about every 6 seconds, about every 7 seconds, about every 8 seconds, about every 9 seconds, about every 10 seconds, about every 20 seconds, about every 30 seconds, about every 45 seconds, about every 60 seconds, about every 70 seconds, about every 80 seconds, about every 90 seconds, about every 100 seconds, about every 110 seconds, about every 120 seconds, about every 130 seconds, about every 140 seconds, about every 150 seconds, about every 160 seconds, about every 170 seconds, about every 180 seconds, about every 190 seconds, about every 200 seconds, about every 210 seconds, about every 220 seconds, about every 230 seconds, about every 240 seconds, about every 250 seconds, or about every 300 seconds, or more. Signal may be collected once or more than once per temperature interval. For example, a signal may be collected at the end of a temperature interval prior to elevating the temperature to a next temperature interval. Collecting signal may comprise imaging, as described herein. Processing collected signals may comprise using the signals to generate signal versus temperature data for the subset of the plurality of nucleic acid molecules in the subset of the plurality of partitions.

The plurality of nucleic acid molecules analyzed in the method may derive from a sample containing or suspected of containing a pathogen. The pathogen may be at least one bacterium. The bacterium may be selected from the group consisting of, but not limited to, *Bacillus anthracis, Bacillus cereus, Bacillus halodurans, Bacillus mycoides, Bacillus polymexa, Bacillus subtilis, Bacillus thuringensis, Staphylococcus capitis, Staphylococcus caprae, Staphylococcus haemolyticus, Staphylococcus hominis, Staphylococcus lentus, Staphylococcus lugdunensis, Staphylococcus saprophyticus, Staphylococcus xylosus, Propionibacterium acnes, Enterococcus faecalis*, Actinobacteria, Alphaproteobacteria, Bacteroidetes, Betaproteobacteria, Chlamydiaes, Epsilonproteobacteria, Firmicutes, Gammaproteobacteria, Spirochaetales, and Tenericutes. The method may involve an additional processing step to isolate or extract nucleic acid molecules from bacterium. Performing nucleic acid amplification reactions on the nucleic acid sample may comprise amplifying at least a portion of an internal transcribed spacer region of a subset of the nucleic acid molecules of the nucleic acid sample. Alternatively or in addition, amplification of a ribosomal RNA (e.g., 16S) may occur.

A sample for use in the methods described herein may be a biological sample. A biological sample may comprise a bodily fluid selected from the group consisting of blood, urine, semen, mucus, saliva, and any combination thereof. Alternatively, the sample may be an environmental sample, as described herein.

The method may further comprise loading the plurality of nucleic acid molecules into the plurality of partitions of the device, where during loading, gas in the subset of the plurality of partitions including the plurality of nucleic acid molecules is subjected to flow from the subset of the plurality of partitions to the external environment.

The device used in a method of analyzing nucleic acid molecule may have any features described herein. The barrier of the device may comprise a polymeric material, such as a thermoplastic material, and may be a thin film. The barrier may be substantially optically transparent. The barrier may have a thickness from about 50 µm to about 200 µm (e.g., about 50 µm, 100 µm, 150 µm, or 200 µm). The device may comprise at least one microchannel comprising at least one inlet and at least one outlet and a plurality of siphon apertures. The subset of the plurality of partitions may be in fluid communication with the microchannel by the plurality of siphon apertures. The plurality of partitions may include from about 1,000 to about 20,000 partitions (e.g., about 1,000, 1,500, 2,000, 2,500, 3,000, 3,500, 4,000, 4,500, 5,000, 10,000, 15,000, or 20,000 partitions).

Figure 22A:
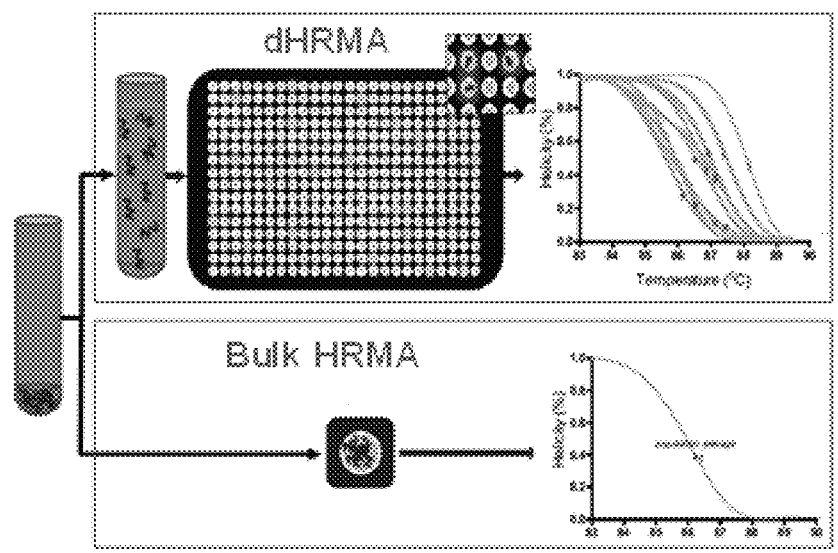
FIGS. 22A-22B schematically illustrate a high resolution melt (HRM) analysis.
Figure 22B:
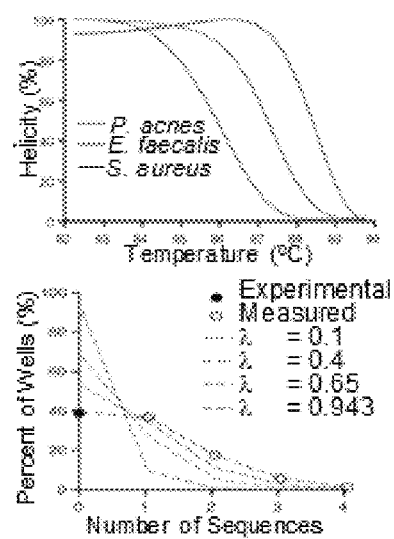

FIGS. 22A-22B schematically illustrate a high resolution melt (HRM) analysis. FIG. 22A illustrates the differences between digital and bulk HRM analyses. As shown in the top panel, in digital HRM analysis, each partition includes at most 1 target DNA molecule and melt curves of different bacteria are resolved. The bottom panel shows bulk HRM analysis, in which a single, non-differentiable melt curve is measured from a heterogeneous sample. FIG. 22B shows HRM curves for a mixed sample including multiple different bacterial species. Distinct helicity curves from *S. aureus, E. faecalis*, and *P. acnes* are shown in the top panel, while the bottom panel shows their use to determine occupation of partitions using Poisson statistics.

Figures 23A, 23B, 23C, 23D, 23E:
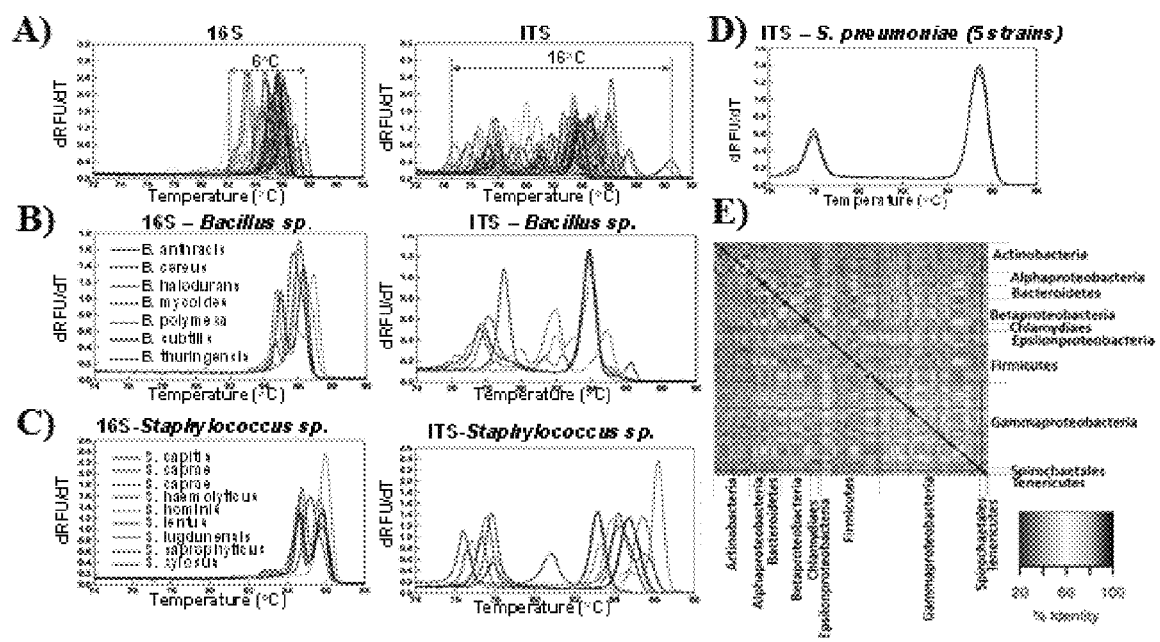
FIGS. 23A-23E show HRM data for various bacterial species.

FIGS. 23A-23E show HRM data for various bacterial species. FIG. 23A shows 16S and internal transcribed spacer (ITS) composite derivative HRM curves for 89 different bacteria. Notably, melt curves corresponding to ITS regions of bacterial nucleic acid molecules show a broader temperature range and greater curve diversity than melt curves corresponding to 16S ribosomal RNA. FIG. 23B shows HRM curves for 7 different species of the *Bacilus* genus, while FIG. 23C shows HRM curves for 9 different species of the *Staphylococcus* genus and FIG. 23D shows ITS HRM curves for 5 different species of *S. pneumonia*. FIG. 23E shows a heat map of ITS sequence homology for 153 different bacterial species organized by phylum.

Figure 24A:
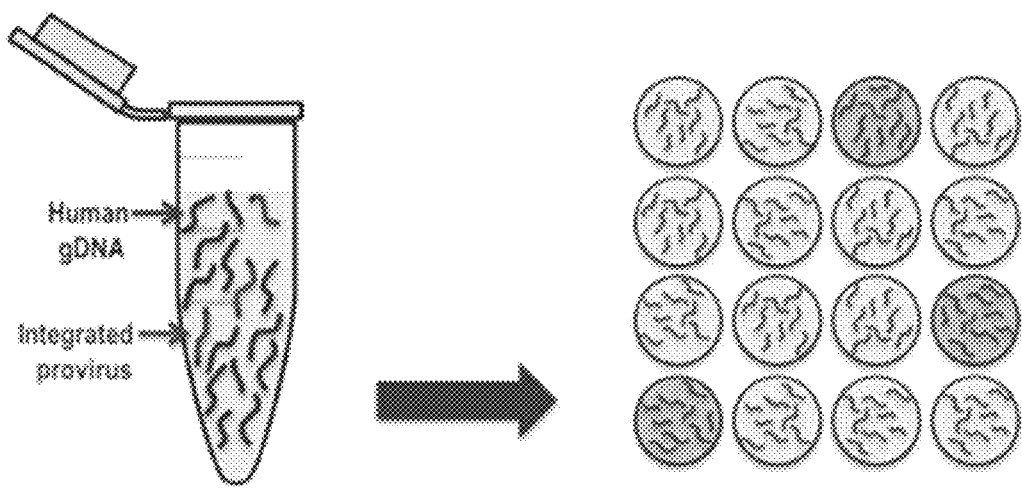
FIGS. 24A-24B schematically illustrate an HRM analysis.
Figure 24B:
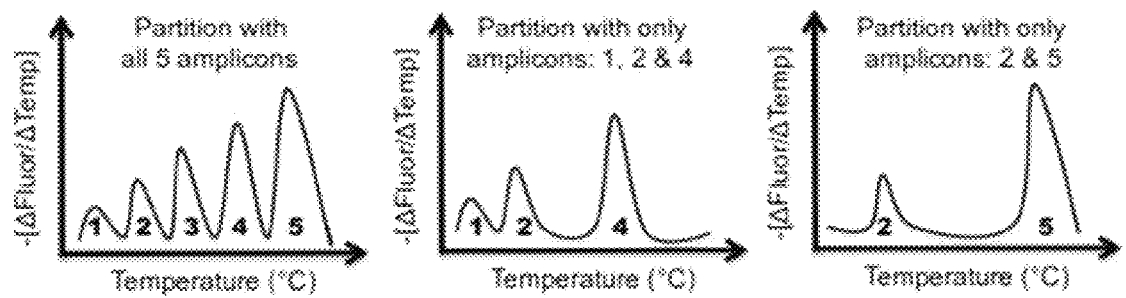

FIGS. 24A-24B schematically illustrate an HRM analysis. FIG. 24A illustrates partitioning of DNA from a sample amplified with a bulk PCR reaction including a plurality of human gDNA and HIV proviral DNA molecules. The sample is partitioned such that there is an average of about 3 billion base pairs of gDNA per partition and HIV proviral DNA is undisturbed. FIG. 24B shows a hypothetical HRM analysis for partitions where PCR has occurred. Each panel shows temperature dependent fluorescent signal corresponding to different theoretical partition populations. The leftmost panel illustrates hypothetical signal for a partition including all 5 amplicons; the central panel illustrates hypothetical signal for a partition including only amplicons 1, 2, and 4; and the right-most panel illustrates hypothetical signal for a partition including only amplicons 2 and 5.

System for Analyzing a Sample

In an aspect, the present disclosure provides a system for using a microfluidic device (e.g., as described herein) to analyze a plurality of nucleic acid molecules. The system may comprise a support unit configured to accept a device comprising a plurality of partitions. Each partition of a subset of the plurality of partitions of the device is configured to permit gas flow from the partitions to an environment external to the partitions through at least one barrier separating the subset of the plurality of partitions from the external environment. The system may also comprise a detector configured to collect signals from the subset of the plurality of partitions of the device over a plurality of time points. The system may also include one or more computer processors operatively coupled to the detector. The one or more computer processors may be individually or collectively programmed to subject the subset of the plurality of partitions to conditions sufficient to conduct nucleic acid amplification reactions, as described herein, using a plurality of nucleic acid molecules to generate amplification products from at least a subset of the plurality of nucleic acid molecules. The one or more computer processors may also be programmed to, while amplification reactions are in progress receive the signals collected from the subset of the plurality of partitions by the detector over the plurality of time points. The signals may be collected and stored at the detector and sent to the processor(s) at a given time or may be provided to the processor(s) as signals are collected. The one or more computer processors may be programmed to direct the collection of signal from the subset of the plurality of partitions. They may also be programmed to process collected signals to determine a number of nucleic acid molecules in the subset of the plurality of partitions. The system may further comprise a fluid flow unit (e.g., a pneumatic unit) that is configured to direct the plurality of nucleic acid molecules to the plurality of partitions. The one or more computer processors may be individually or collectively programmed to direct the fluid flow unit to load the plurality of nucleic acid molecules into the plurality of partitions.

The present disclosure also provides a system for using a microfluidic device (e.g., as described herein) to analyze a sample containing or suspected of containing a plurality of nucleic acid molecules. Such analysis may involve a thermodynamic assessment of dissociation characteristics of a nucleic acid molecule, such as DNA in the sample. The thermodynamic assessment may include a determination of a melting point of the DNA and binding strength of individual strands of the DNA molecule.

The system may comprise a support unit and a detector, as described above. The system may further comprise a thermal unit configured to subject the subset of the plurality of partitions to controlled heating. The system may also include one or more computer processors operatively coupled to the detector. The one or more computer processors may be individually or collectively programmed to direct the thermal unit to subject the subset of the plurality of partitions to controlled heating. The one or more computer processors may also be programmed to receive the signals collected from the subset of the plurality of partitions by the detector while the subset of the plurality of partitions are subjected to controlled heating. They may also be programmed to process collected signals to yield data indicative of a melting point of the subset of the plurality of partitions. The system may further comprise a fluid flow unit (e.g., a pneumatic unit) that is configured to direct the plurality of nucleic acid molecules to the plurality of partitions. The one or more computer processors may be individually or collectively programmed to direct the fluid flow unit to load the plurality of nucleic acid molecules into the plurality of partitions.

The system may comprise a support unit such as a transfer stage, platform, slot, or groove configured to hold one or more microfluidic devices. The microfluidic devices may comprise a microchannel with an inlet and an outlet, a plurality of microchambers connected to the microchannel by a plurality of siphon apertures, and a thin film (e.g., a thermoplastic thin film) capping or covering the microfluidic device. The apparatus may comprise a pneumatic unit in fluid communication with the microfluidic device. The pneumatic unit may load reagent into the microfluidic device and partition the reagent into the microchambers. The system may comprise a thermal unit in thermal communication with the plurality of microchambers. The thermal unit may control the temperature of the microchambers and thermal cycle the microchambers. The system may comprise detector for collecting signals from the microchambers of the device, or a subset thereof. The detector may be an optical unit capable of imaging the plurality of microchambers. The system may also comprise one or more computer processors coupled to the support unit, pneumatic unit, thermal unit, and detector (e.g., optical unit). The one or more computer processors may be programmed to (i) direct the pneumatic unit to load reagent into the microfluidic device and partition the reagent into the plurality of microchambers, (ii) direct the thermal unit to thermal cycle the plurality of microchambers, and (iii) direct the detector (e.g., optical unit) to collect signals from (e.g., image) the plurality of microchambers.

The support unit may be configured input the microfluidic device, hold the microfluidic device, and output the microfluidic device. The support unit may be stationary in one or more coordinates. Alternatively, or in addition, the support unit may be capable of moving in the X-direction, Y-direction, Z-direction, or any combination thereof. The support unit may be capable of holding a single microfluidic device. Alternatively, or in addition, the transfer stage may be capable of holding at least 2, at least 3, at least 4, at least 5, at least 6, at least 7, at least 8, at least 9, at least 10, or more microfluidic devices.

The pneumatic unit may be configured to be in fluid communication with the inlets and the outlets of the microfluidic device. The pneumatic unit may have multiple connection points capable of connecting to multiple inlets and multiple outlets. The pneumatic unit may be able to fill, backfill, and partition a single array of microchambers at a time or multiple arrays of microchambers in tandem. The pneumatic unit may further comprise a vacuum unit. The pneumatic unit may provide increased pressure to the microfluidic device or provide vacuum to the microfluidic device.

The thermal unit may be configured to be in thermal communication with the microchambers of the microfluidic devices. The thermal unit may be configured to control the temperature of a single array of microchambers or to control the temperature of multiple arrays of microchambers. The thermal control unit may perform the same thermal program across all arrays of microchambers or may perform different thermal programs with different arrays of microchambers. The thermal unit may be configured to carry out both thermal cycling and controlled heating. Alternatively, a system may include multiple thermal units, each of which is configured to carry out a separate thermal process such as thermal cycling and controlled heating.

The detector may be configured to collect signals from all or a subset of the plurality of partitions of the device. For example, the detector may collect optical, impedance, or any other useful signal type. The detector may be an optical unit. The optical unit may be configured to emit and detect multiple wavelengths of light. Emission wavelengths may correspond to the excitation wavelengths of the indicator and amplification probes used. The emitted light may include wavelengths with a maximum intensity around about 450 nm, 500 nm, 525 nm, 550 nm, 575 nm, 600 nm, 625 nm, 650 nm, 675 nm, 700 nm, or any combination thereof. Detected light may include wavelengths with a maximum intensity around about 500 nm, 525 nm, 550 nm, 575 nm, 600 nm, 625 nm, 650 nm, 675 nm, 700 nm, or any combination thereof. The optical unit may be configured to emit one, two, three, four, or more wavelengths of light. The optical unit may be configured to detect one, two, three, four, or more wavelengths of light. On emitted wavelength of light may correspond to the excitation wavelength of indicator molecule. Another emitted wavelength of light may correspond to the excitation wavelength of the amplification probe. One detected wavelength of light may correspond to the emission wavelength of an indicator molecule. Another detected wavelength of light may correspond to an amplification probe used to detect a reaction within the microchambers. The optical unit may be configured to image subsets of microchambers or sections of an array of microchambers. Alternatively, or in addition, the optical unit may image an entire array of microchambers in a single image.

Figure 6:
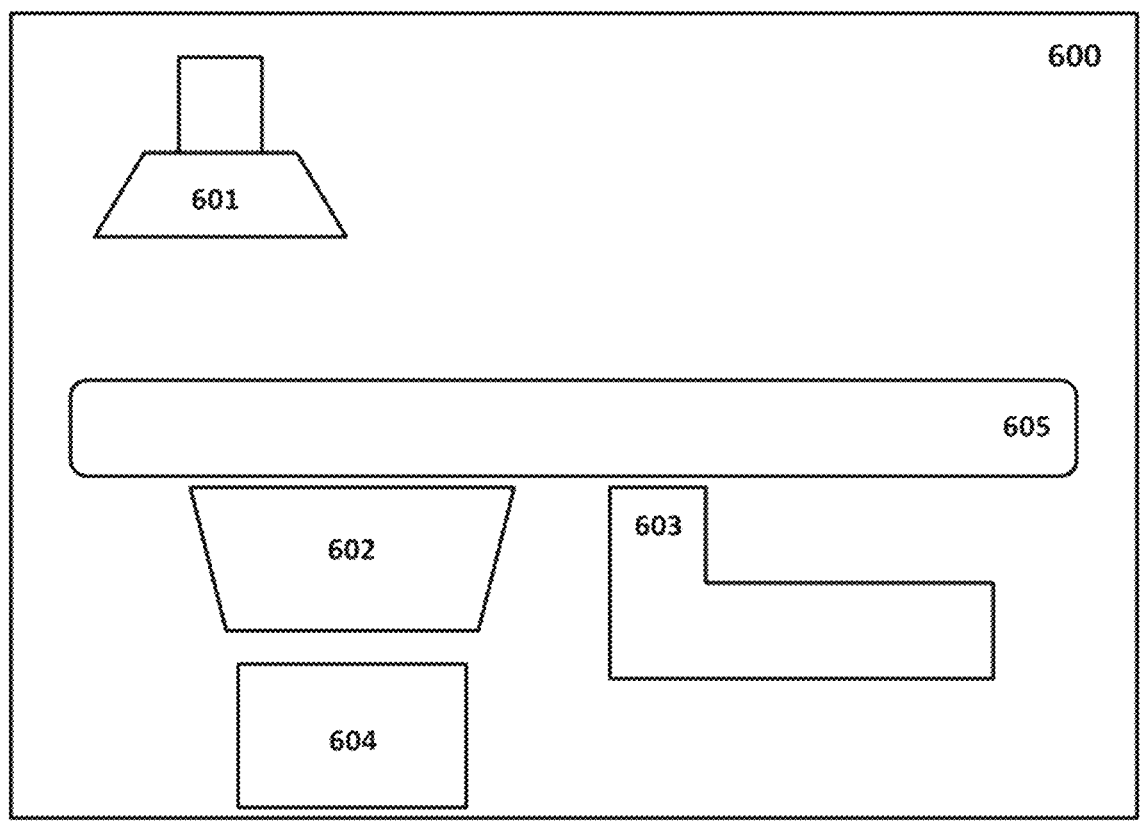
FIG. 6 schematically illustrates a machine for performing the a nucleic acid amplification and quantification method in a single machine.

FIG. 6 illustrates a machine 600 for performing the process of FIG. 5 in a single machine. The machine 600 includes a pneumatic unit 601, which contains pumps and manifolds and may be moved in a Z-direction, operable to perform the application of pressure as described in FIGS. 3A-3D. Machine 600 also includes a thermal unit 602, such as a flat block thermal cycler, to thermally cycle the microfluidic device and thereby cause the polymerase chain reaction to run. Machine 600 further includes an optical unit 603, such as an epi-fluorescent optical unit, which can optically determine which microchambers in the microfluidic device have successfully run the PCR reaction. The optical unit 603 may feed this information to a processor 604, which uses Poisson statistics to convert the raw count of successful microchambers into a nucleic acid concentration. A support unit 605 (e.g., a transfer stage) may be used to move a given microfluidic device between the various units and to handle multiple microfluidic devices simultaneously. The microfluidic device described above, combined with the incorporation of this functionality into a single machine, reduces the cost, workflow complexity, and space requirements for dPCR over other implementations of dPCR.

Figure 12A:
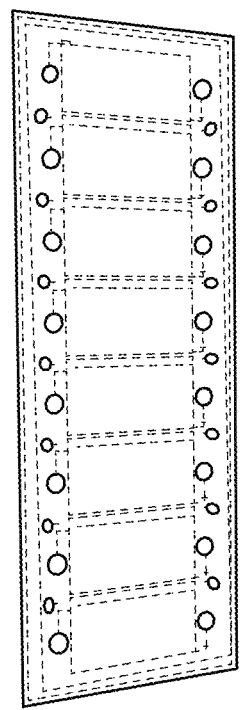
FIGS. 12A-12B show a device for sample processing and/or analysis.
Figure 12B:
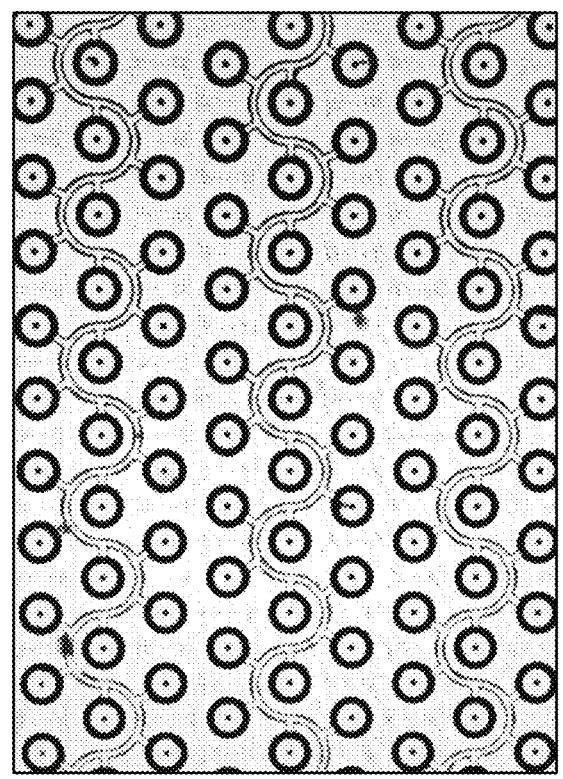

FIG. 12A illustrates a device according to one embodiment of the present disclosure. The device illustrates contains eight independent reaction arrays, each of which may be independently filled with reagent. Each reaction array contains 20,000 individual partitions. FIG. 12B illustrates an arrangement of a portion of the partitions within one reaction array of the device. This illustration shows a close-up view of the serpentine path of the loading conduit and the partitions to be loaded stemming off of the loading conduit. Each circular shape represents an individual partition which may be loaded with reagent containing zero, one, or more nucleic acid templates, and which will be individually amplified and analyzed as described herein.

Figure 13:
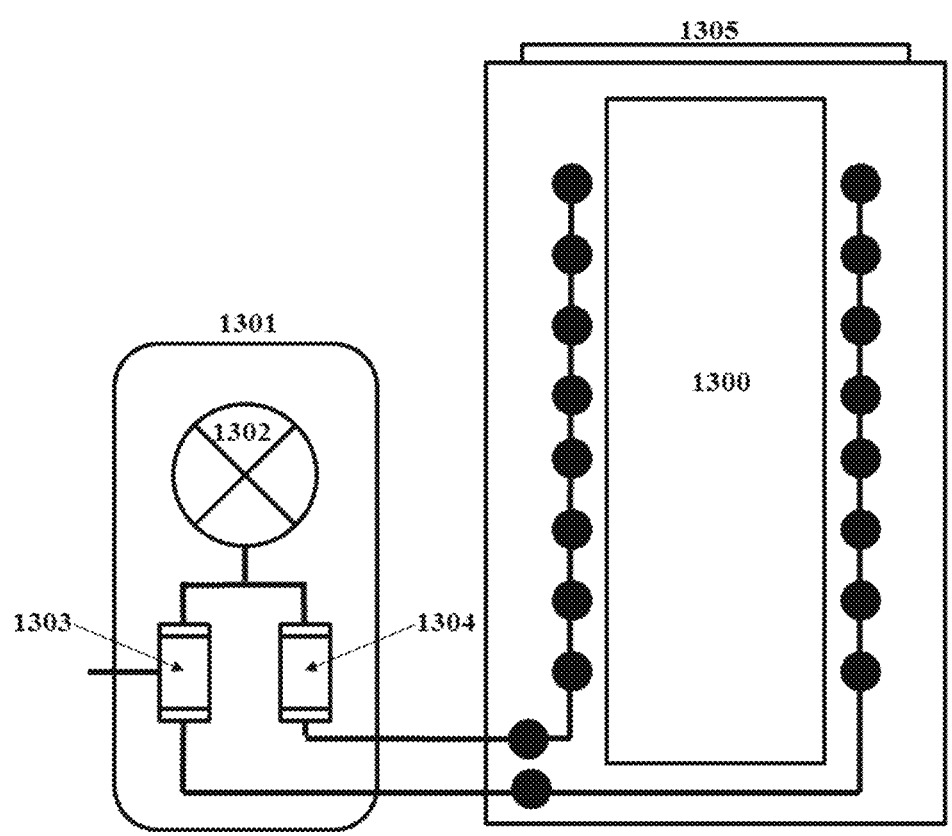
FIG. 13 illustrates a schematic representation of a device for sample processing and/or analysis, along with a pneumatic unit for use in providing device fluidic control.

FIG. 13 illustrates a schematic representation of a device along with a pneumatic unit for use in providing device fluidic control. Each port provides a fluid interface into one of the eight (in this embodiment) reaction arrays on the device 1300. As described herein, a sequence of low and high pressures applied at the inlet and outlet of each reaction array loads reagent into the partitions within the reaction array. Pneumatic unit 1301 controls the application of these pressures, and includes an electronic pressure regulator 1302 and at least two valves 1303 and 1304. More valves may be incorporated (e.g., to provide separate loading of each individual reaction array). The device may include mechanical keys to aid in orientation and registration (such as tab 1305 at the top of the device) within a system of the present disclosure, or may include visual features such as registration marks (not shown).

Figure 14A:
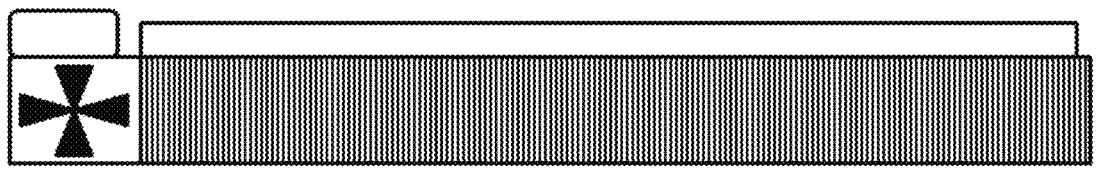
FIGS. 14A-14B schematically illustrate a flat-block thermal cycling unit.
Figure 14B:
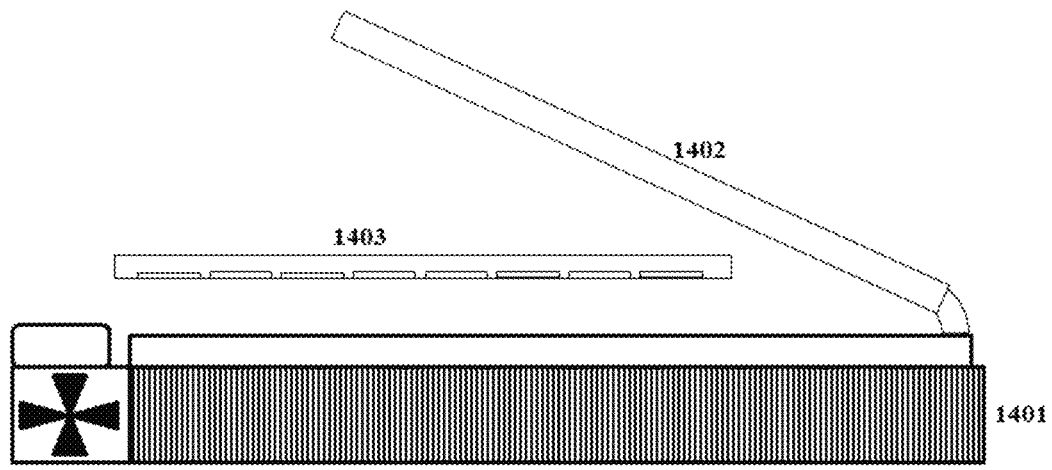

FIG. 14A illustrates a flat block thermal cycling unit for use in embodiments of the present disclosure. The flat block thermal cycling unit provides thermal control to enable PCR amplification cycles according to embodiments of the present disclosure. The flat block includes threaded holes (not shown) such that a pneumatic clamp may be mounted directly to the flat block. This allows the clamping of a device, e.g., as described herein, to the flat block for thermal cycling of the sample and reagent(s) contained within the device.

FIG. 4B illustrates the flat block thermal cycling unit 1401 of FIG. 4A with the addition of a pneumatic clamp 1402, with the clamp opened so that a device 1403 such as the device of FIG. 12A may be loaded into the thermal unit. In the illustration, device 1403 is being loaded into the combined thermal unit/clamp system for a PCR amplification cycle. After loading device 1403 into the thermal unit/clamp system, pneumatic pressure may be applied via a pneumatic drive to clamp down with pneumatic clamp 1402 and hold the device in place. The pneumatic drive may be integrated with the pneumatic unit described above with respect to FIG. 13 or may be a separate pneumatic system. In systems in which the pneumatic unit is integrated, an empty device may be placed into the cycling unit and the device may be loaded with reagent while remaining in place on the block. Reagent and/or sample loading may also be carried out with a separate pneumatic unit before the reagent/sample-loaded device is loaded into the system, e.g., for amplification.

Figure 15:
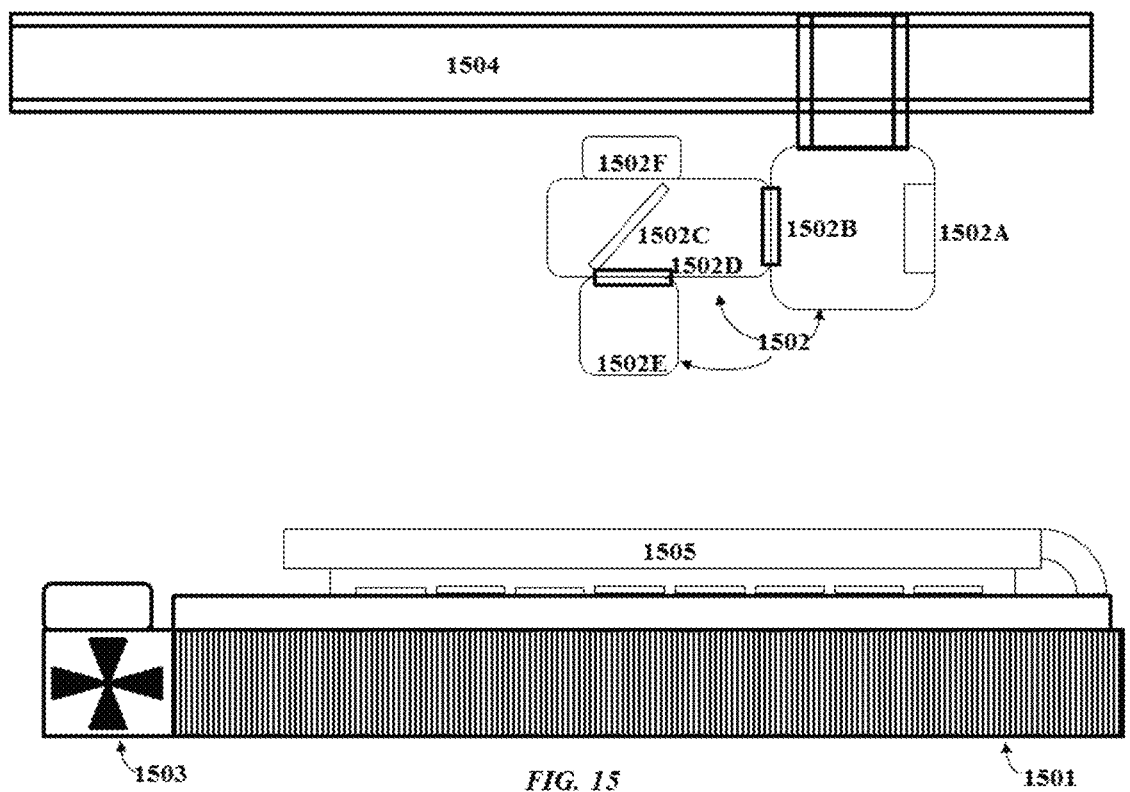
FIG. 15 illustrates a complete qdPCR system for sample processing and/or analysis, including thermal, optical, pneumatic, and mechanical units.

FIG. 15 illustrates a complete qdPCR system 1500 for use in embodiments of the present disclosure. System 1500 includes thermal unit 1501, optical unit 1502 (including components 1502A, 1502B, and 1502C), pneumatic unit 1503, and mechanical unit 1504. Each unit cooperates with the others to perform the qdPCR process according to embodiments of the present disclosure.

Thermal unit 1501 provides thermal cycling and/or controlled heating of the reagent- and/or sample-loaded device or a subset of the plurality of partitions thereof. Thermal unit 1501 provides the ability to subject the device to a thermal cycle and/or controlled heating. As described herein, a thermal cycle may include a denaturation phase, an annealing phase, and an extension phase. A single PCR amplification cycle may occur during a period of, for example, between about 60 to 120 seconds. Other profiles of temperature may also be employed in use with embodiments according to the present disclosure. For example, thermal unit 1501 may be configured to heat the device to a holding temperature which allows storage of the products of the PCR amplification reaction without further change. Thermal unit 1501 may also be configured to perform controlled heating for, e.g., a high resolution melt analysis, as described herein. Thermal unit 1501 may include components such as a temperature control unit, a temperature probe, circuitry, and any other useful components. Thermal unit 1501 may include a support unit for supporting the device and may incorporate a pneumatic clamp 1505 to hold the device to the thermal unit 1501.

Optical unit 1502 provides imaging of the device, or a subset of the plurality of partitions thereof during, before, and/or after an amplification or controlled heating process. Optical unit 1502 may be configured to image each partition, e.g., at least once per amplification cycle. Each partition may be imaged more frequently (e.g., twice per amplification cycle or ten times per amplification cycle), as described herein. Optical unit 1502 may also be configured to image each partition at a plurality of time points during a controlled heating process.

Optical unit 1502 may image the device sectionally (e.g., imaging a 5×5 grid of partitions in each image), as a whole, or on a per-array basis (e.g., imaging all 20,000 partitions in a given array in a single image.) Moving optical unit 1502 may not be required if optical unit 1502 is capable of imaging the entire device in a single shot. For sectional imaging, optical unit 1502 may be configured to orient itself to the device (e.g., using a mechanical key or registration marks) and then scan across the partitions of the device. Alternatively, optical unit 1502 may be fixed in place and thermal unit 1501 may be moved to allow optical unit 1502 to image each partition or group of partitions. Optical unit 1502 may be configured to orient itself using registration marks printed on the device. Optical unit 1502 may be oriented by position of thermal unit 1501, or by positioning of optical unit 1502, thermal unit 1501, and any related handling units. Optical unit 1502 includes light source 1502A, excitation filter 1502B, dichroic mirror 1502C, emission filter 1502D, focus lens 1502E, and image sensor 1502F, as described herein.

Pneumatic unit 1503 provides functionality for fluid handling and/or clamping of the device. The same pneumatic unit 1503 may provide both fluid-handling/reagent-loading capabilities to the device and pneumatic clamping functionality for the pneumatic clamp 1505 mounted on thermal unit 1501. Alternatively, pneumatic unit 1503 may only provide clamping functionality for pneumatic clamp 1505, and a separate pneumatic unit (not shown) provides reagent loading for the device.

Mechanical unit 1504 provides mechanical handling and movement of the various components. In the illustrated embodiment, mechanical unit 1504 provides the ability to scan optical unit 1502 across the partitions of the device. In this embodiment, mechanical unit 1504 moves optical unit 1502 to the next imaging position, allows it to image, and then repeats the process until all partitions have been imaged. This process may be repeated as many times as are necessary, depending on the number of amplification cycles and the number of images per cycle that are desired and/or the controlled heating process of interest. Mechanical unit 1504 may move thermal unit 1501 instead of the optical unit 1502. For example, mechanical unit 1504 may move thermal unit 1501 to an imaging position so that an image may be taken by optical unit 1502, and then thermal unit 1501 may be moved again to allow imaging of a new imaging position. This process may be repeated as needed. Mechanical unit 1504 may provide additional functionality such as mechanical handling of the device to load it into thermal unit 1501 prior to the performance of the qdPCR process or to automatically unload it from the thermal unit 1501 after the qdPCR process is completed.

A system of the present disclosure may include multiple instances of one or more of thermal unit 1501, optical unit 1502, pneumatic unit 1503, and mechanical unit 1504 may be incorporated into the same system in order to provide an automatic system which can process multiple devices at the same time, or which may allow performance of different steps on different devices in sequence. In addition, the system may incorporate a processor in order to implement analysis of amplification dynamics detected by optical unit 1502 or for other analytical functionality as described above with respect to the present disclosure.

Figure 17A:
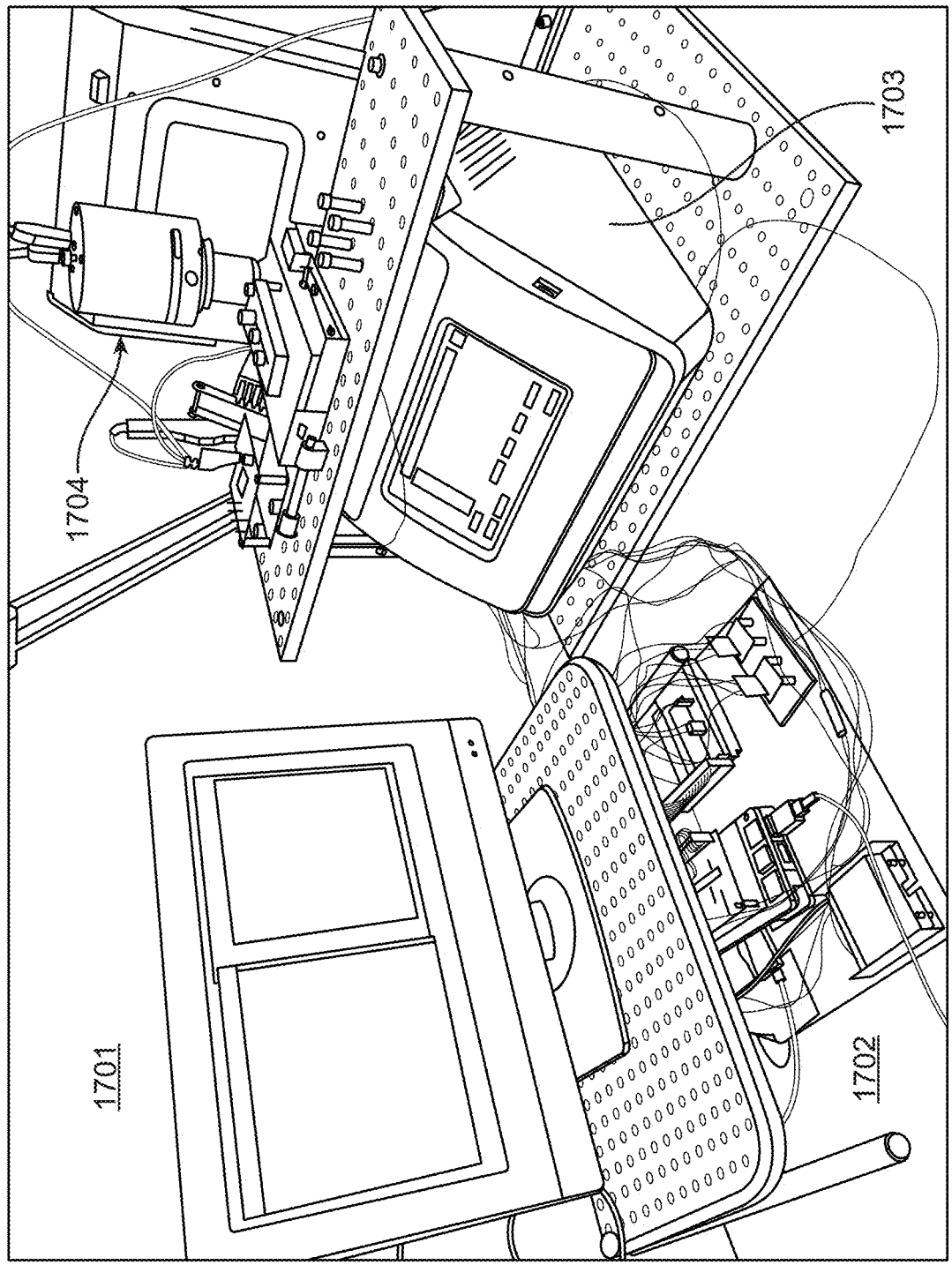
FIGS. 17A-17B show an example system for processing a nucleic acid molecule.
Figure 17B:
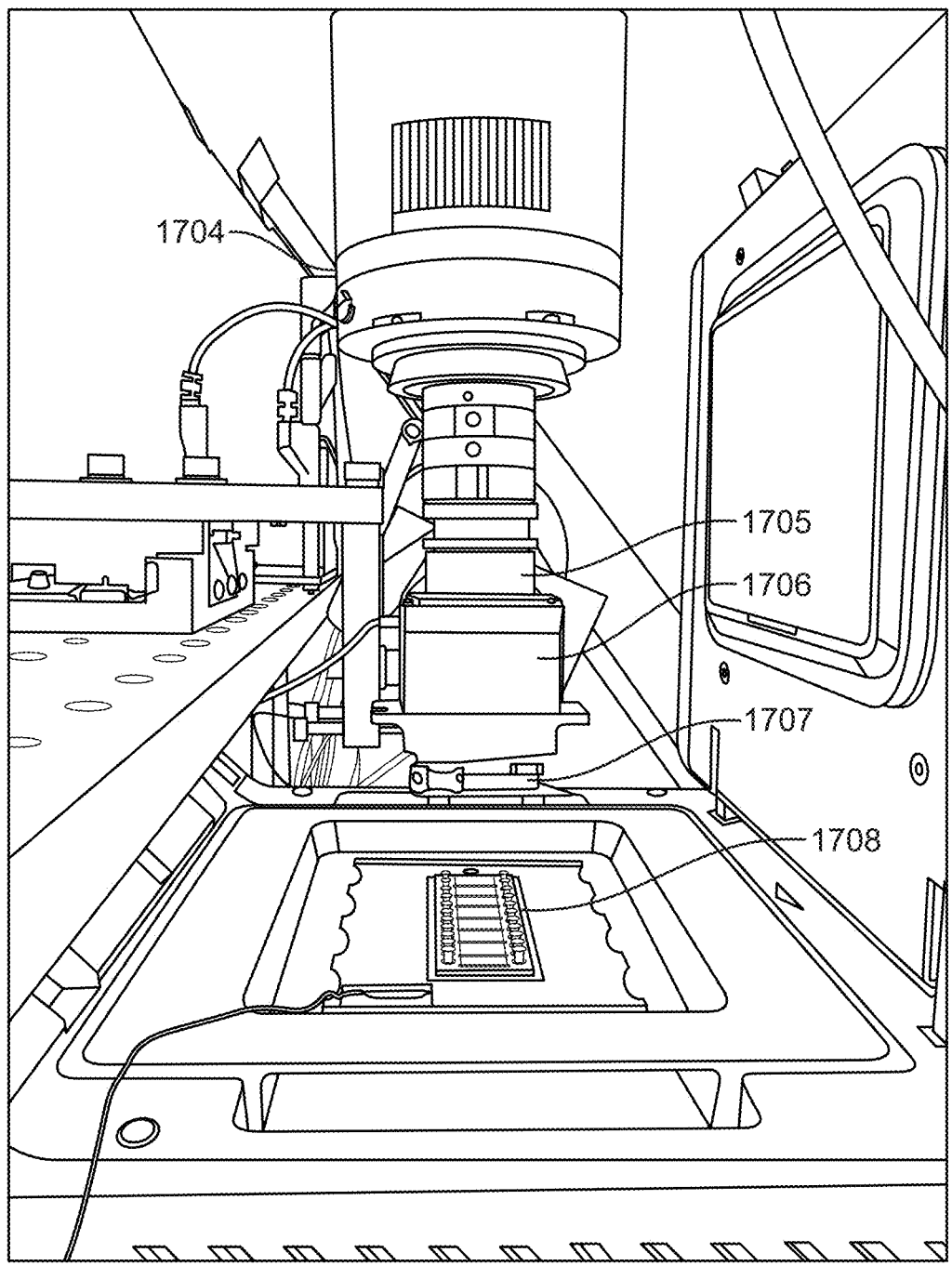

FIGS. 17A-17B show an example system for processing a nucleic acid molecule. FIG. 17A shows the entire example system for processing a nucleic acid molecule including user interface 1701 coupled to computer processor 1702, thermal unit 1703, and camera 1704. FIG. 17B shows a close-up image illustrating camera 1704, LED emitter/heat sink 1705, filter cube 1706, and shutter 1707 above device 1708.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings.

For example, while described in the context of a dPCR application, other microfluidic devices which may require a number of isolated microchambers filled with a liquid, that are isolated via a gas or other fluid, may benefit from the use of a thin thermoplastic film to allow outgassing to avoid gas fouling while also providing an advantage with respect to manufacturability and cost. Other than PCR, other nucleic acid amplification methods such as loop mediated isothermal amplification can be adapted to perform digital detection of specific nucleic acid sequences according to embodiments of the present disclosure. The microchambers can also be used to isolate single cells with the siphoning apertures designed to be close to the diameter of the cells to be isolated. When the siphoning apertures are much smaller than the size of blood cells, the methods described herein may be used to, for example, separate blood plasma from whole blood.

Computer Systems for Analyzing a Nucleic Acid Sample

Figure 7:
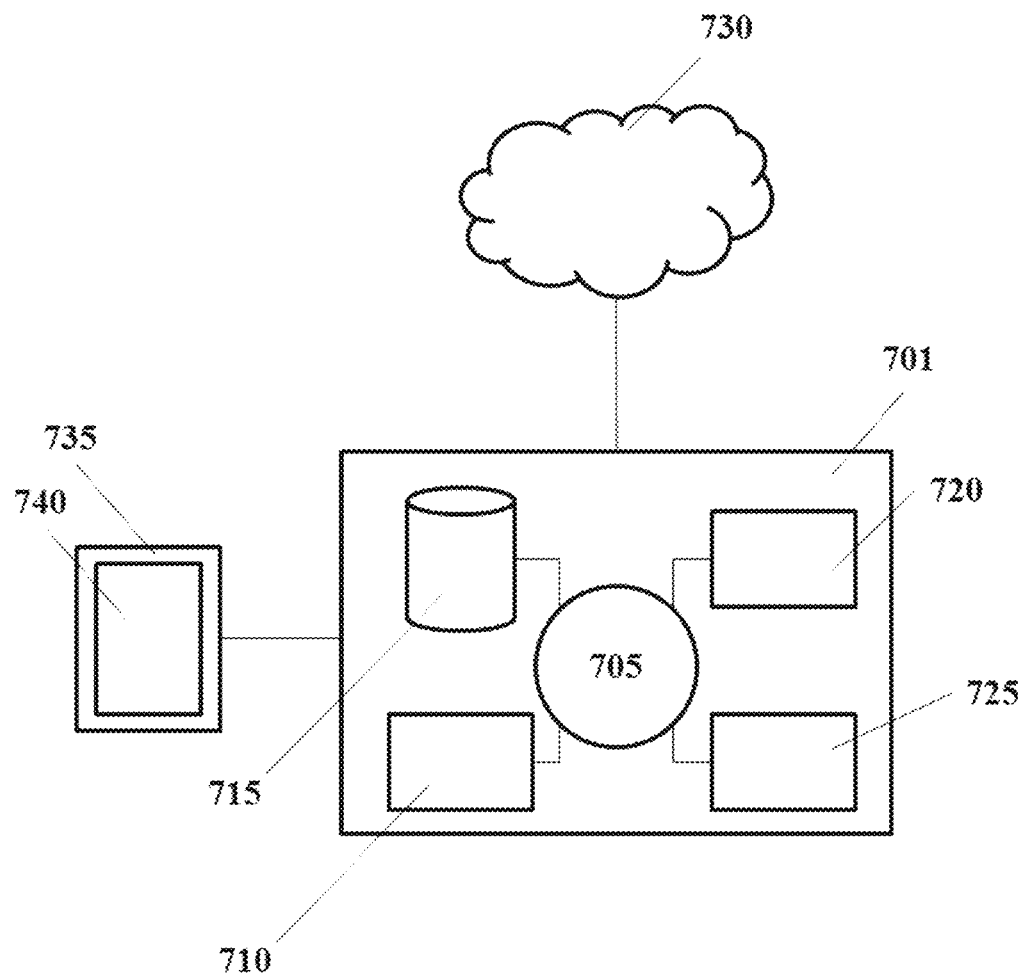
FIG. 7 schematically illustrates an example computer control system that is programmed or otherwise configured to implement methods provided herein.

The present disclosure provides computer control systems that are programmed to implement methods of the disclosure. FIG. 7 shows a computer system 701 that can be programmed or otherwise configured for nucleic acid sample processing and analysis, including sample partitioning, amplification, and detection. The computer system 701 can regulate various aspects of methods and systems of the present disclosure. The computer system 701 can be an electronic device of a user or a computer system that can be remotely located with respect to the electronic device. The electronic device can be a mobile electronic device.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 730 with the aid of the communication interface 720. The network 730 can be the Internet, an internet and/or extranet, or an intranet and/or extranet that can be in communication with the Internet. The network 730 in some cases can be a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user (e.g., service provider). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processor adapted to execute the code, or can be compiled during runtime. The code can be supplied in a programming language that can be selected to enable the code to execute in a pre-compiled or as-compiled fashion.

In an aspect, the present disclosure provides a non-transitory computer-readable medium comprising machine executable code that, upon execution by one or more computer processors, implements a method for forming a microfluidic device to amplify and quantify a nucleic acid sample. The method may comprise: injection molding thermoplastic to create a microfluidic structure comprising at least one microchannel, a plurality of microchambers, and a plurality of siphon apertures, wherein the plurality of microchambers are connected to the at least one microchannel by the plurality of siphon apertures; forming at least one inlet and at least one outlet, wherein the at least one inlet and the at least one outlet are in fluid communication with the at least on microchannel; and applying a thermoplastic thin film to cap the microfluidic structure, wherein the thermoplastic thin film is at least partially gas permeable to a pressure differential is applied across the thermoplastic thin film.

In another aspect, the present disclosure provides a non-transitory computer-readable medium comprising machine executable code that, upon execution by one or more computer processors, implements a method for analyzing and quantifying a nucleic acid sample. The method may comprise one or more of the following: providing the microfluidic device comprising a plurality of microchambers; filling the microfluidic device with sample and/or one or more reagents, as described herein (e.g., using a pneumatic or fluid flow unit and a series of pressure differentials); heating the plurality of microchambers of the device, or a subset thereof, either cyclically (e.g., thermal cycling for amplification reactions) and/or in a controlled ramp up (e.g., for high resolution melt or other thermodynamic analysis); collecting signals from the plurality of microchambers, or a subset thereof, while amplification reactions or controlled heating or ongoing or after these processes have completed; and processing signals collected from the plurality of microchambers to determine a number of nucleic acid molecules in the subset of the plurality of partitions and/or to yield data indicative of a melting point corresponding to the plurality of nucleic acid molecules, or a subset thereof, in the subset of the plurality of partitions. The one or more processors may also be programmed to implement a method of filling the microchambers of a device, or a subset thereof, with sample and/or reagent. The method may comprise: providing the microfluidic device comprising at least one microchannel, wherein the at least one microchannel comprises at least one inlet and at least one outlet, and wherein the microfluidic device further comprises a plurality of microchambers connected to the microchannel by a plurality of siphon apertures, and a thermoplastic thin film disposed adjacent to a surface of the microfluidic device such that the thermoplastic thin film caps the microchannel, the plurality of microchambers, and the plurality of siphon apertures; providing a reagent to the at least one inlet or the at least one outlet; filling the microfluidic device by providing a first pressure differential between the sample and/or reagent and the microfluidic device, wherein the first pressure differential causes the sample and/or reagent to flow into the microfluidic device; applying a second pressure differential between the microchannel and the plurality of microchambers to move the sample and/or reagent into the plurality of microchambers and to force gas within the plurality of microchambers to pass through the thermoplastic thin film capping or covering the plurality of microchambers, the plurality of siphon apertures, and the microchannel, wherein the second pressure differential is greater than the first pressure differential; and applying a third pressure differential between the at least one inlet and the at least one outlet to introduce a fluid into the microchannel without introducing the fluid into the microchambers, wherein the third pressure differential is less than the second pressure differential.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated units or modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, for example, depth profile of an epithelial tissue. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 705. The algorithm can, for example, regulate systems or implement methods provided herein.

While preferred embodiments of the present disclosure have been shown and described herein, it will be obvious to those skilled in the art that such embodiments are provided by way of example only. Numerous variations, changes, and substitutions will now occur to those skilled in the art without departing from the inventions described herein. It should be understood that various alternatives to the embodiments of the inventions described herein may be employed in practicing the invention. It is intended that the following claims define the scope of the invention and that methods and structures within the scope of these claims and their equivalents be covered thereby.

EXAMPLE 1

Demonstration of Reagent Partitioning

Figure 8A:
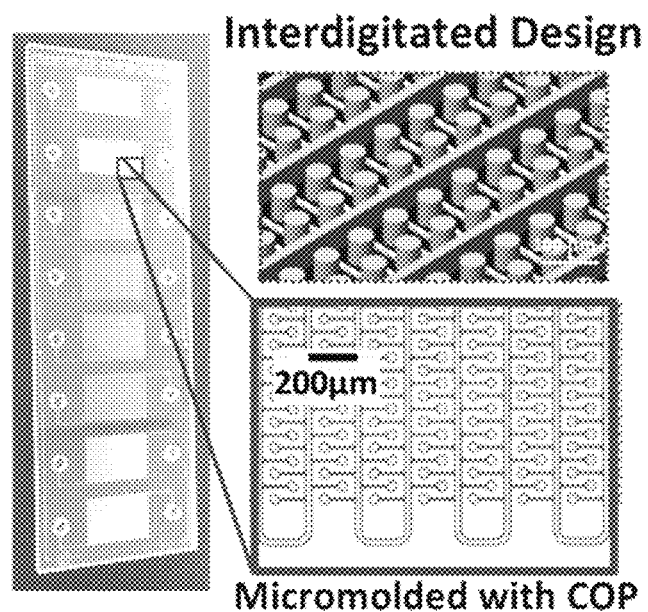
FIGS. 8A and 8B show the microfluidic device and sample partitioning.

Reagent partitioning is demonstrated using a microfluidic device fabricated using standard microscope slide dimensions. The total dimensions of the microfluidic device are 1 inch wide, 3 inches long, and 0.6 inches thick. The device contains four different microchamber array designs and a total of eight different arrays of microchambers. FIG. 8A shows the eight-unit device and an enlarged perspective of one of the four array designs. The microfluidic device is molded from a cyclo-olefin polymer (COP), Zeonor 790R (Zeon Chemicals, Japan) and sealed by thermal bonding with a 100 μm COP thin film, Zeonox ZF14 (Zeon Chemicals, Japan). The shown enlarged microfluidic segment has a serpentine microchannel connected to microchambers by siphon apertures. The microchambers are in a gridded configuration. The microchambers and microchannel have a depth of 40 μm the siphon apertures have a depth of 10 μm. Each isolated microfluidic segment has an inlet and an outlet channel. The inlet and outlet channels are mechanically drilled before the film is thermally bonded to the base of the microfluidic device. The inlet and outlet channels are 1.6 mm in diameter.

Figure 8B:
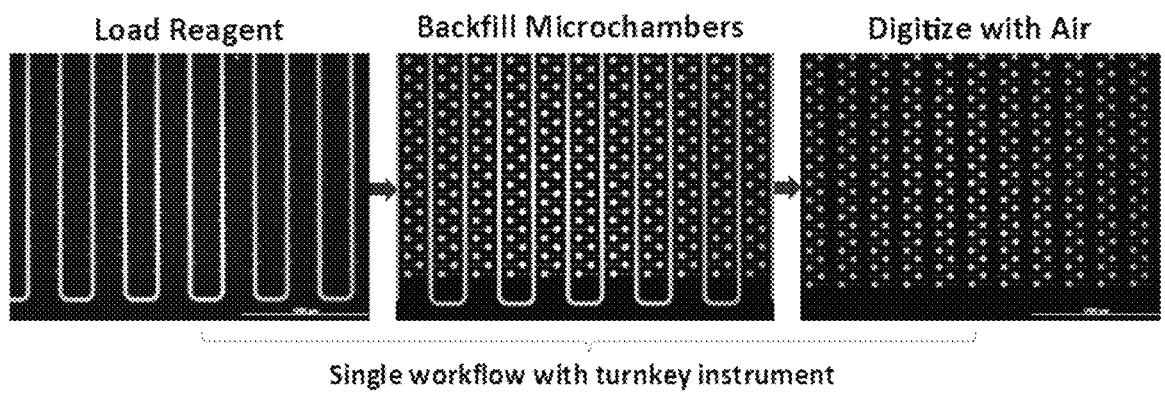

FIG. 8B shows fluorescent images of reagent loading, microchamber backfilling, and partitioning. Prior to loading the microfluidic device 2 microliters (μL) of a 4 kiloDalton (kDa) fluorescein conjugated dextran (Sigma-Aldrich, St. Louis, Mo.) is pipetted into the inlet. The microfluidic device is then contacted with a pneumatic controller. The pneumatic controller loads the microchannel of the microfluidic device by applying 4 psi of pressure to the inlet for 3 minutes. The microchambers are filled by pressurizing both the inlet and the outlet to 10 psi for 20 minutes. The reagent is then partitioned by flowing air at 4 psi from the inlet of the microfluidic device to clear reagent from the microchannel.

Figure 20A:
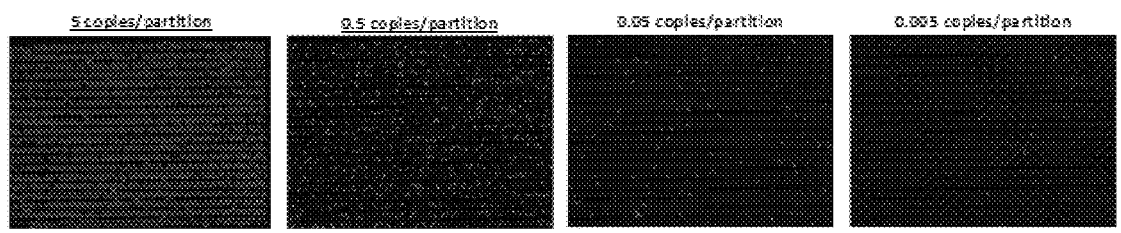
FIGS. 20A-20B show differential loading of a device useful sample processing and/or analysis.
Figure 20B:
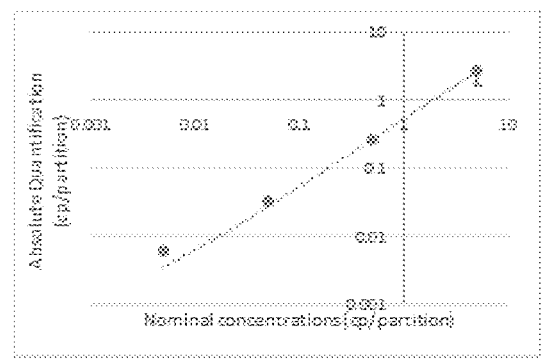
Figure 21:
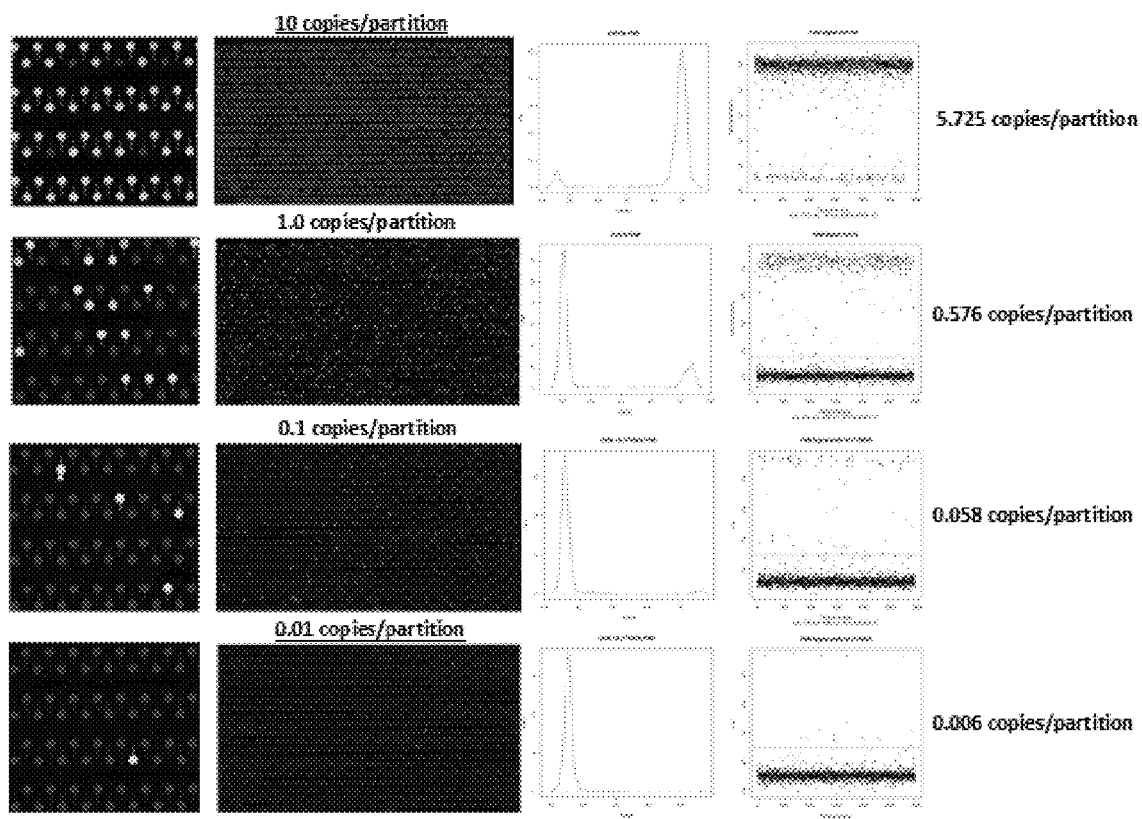
FIG. 21 shows images and corresponding density and partition occupation for differently loaded devices useful for sample processing and/or analysis.

FIG. 20A shows images corresponding to differential viral loading of a series of devices. The panels include images of partitions including 5, 0.5, 0.05, and 0.005 nucleic acid copies per partition. These images were taken subsequent to thermal cycling and were imaged using a fluorescent imager for FAM and ROX fluorophores. FIG. 20B shows the corresponding Poisson analysis of the images in FIG. 20A using Image J and R software. Similarly, FIG. 21 shows images corresponding to differential loading of a series of devices. The panels include images of partitions including 10, 1.0, 0.1, and 0.01 nucleic acid copies per partition. The rightmost panels show corresponding density and partition occupation corresponding to each device.

EXAMPLE 2

Single Instrument Workflow for dPCR

Figure 9:
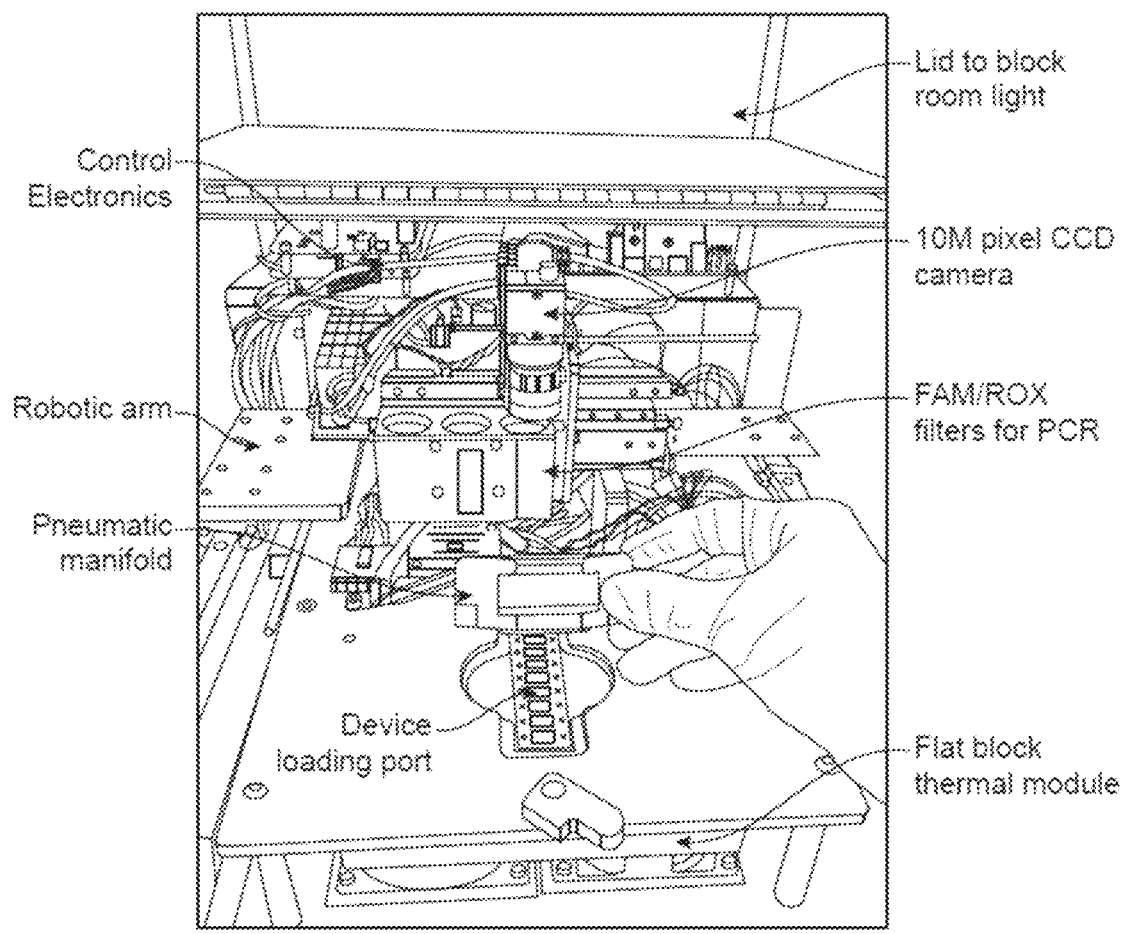
FIG. 9 shows an example system for processing a nucleic acid sample.

The methods for amplification and quantification of nucleic acids in the microfluidic device may be performed in a single instrument. The instrument may be capable of reagent partitioning, thermal cycling, image acquisition, and data analysis. FIG. 9 shows a prototype instrument capable of a single instrument work flow. The instrument is designed to accommodate up to four devices at a time and enable concurrent image acquisition and thermal cycling. The instrument contains a pneumatic unit for reagent partitioning, a thermal unit for temperature control and thermal cycling, an optical unit for imaging, and a scanning unit. The optical unit has two fluorescent imaging capabilities and is able to detect fluorescent emissions of approximately 520 nm and 600 nm, which correspond to the emission wavelengths of FAM and ROX fluorophores, respectively. The optical unit has a 25 mm by 25 mm field of view and a Numerical Aperture (NA) of 0.14.

Figure 10A:
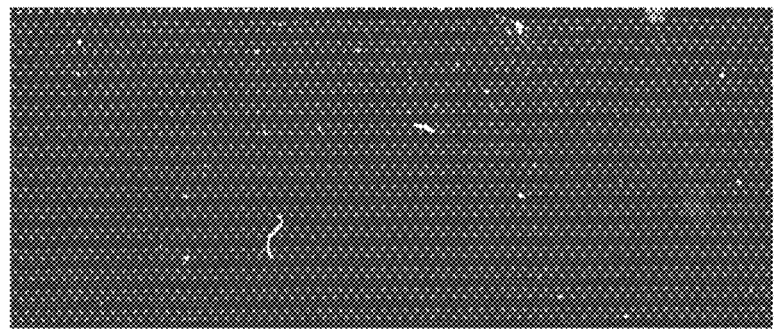
FIGS. 10A-10D show two color (one color representing sample signal and the other representing a normalization signal) fluorescent detection of nucleic acid amplification of partitions containing approximately one nucleic acid template copy on average and partitions containing zero nucleic acid template copies (no template control or NTC)
Figure 10B:
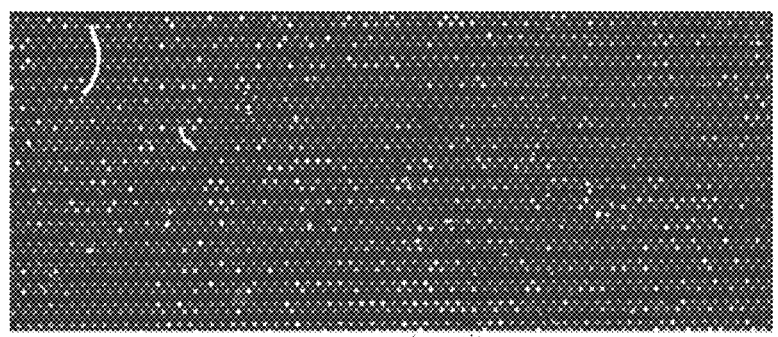
Figure 10C:
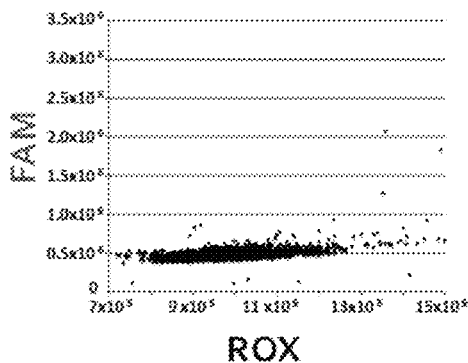
Figure 10D:
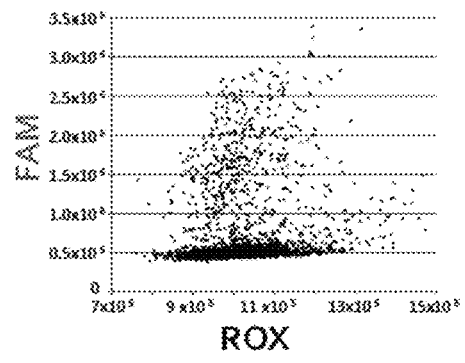

The single instrument workflow may be tested using a well-established qPCR assay utilizing a TaqMan probe as a reporter. Briefly, a nucleic acid sample is mixed with PCR reagents. The PCR reagents include forward primers, reverse primers, TaqMan probes, and a ROX indicator. The sequence of the forward primer is 5'-GCC TCA ATA AAG CTT GCC TTG A-3' (SEQ ID NO: 1). The sequence of the reverse primer is 5'-GGG GCG CAC TGC TAG AGA-3' (SEQ ID NO: 2). The sequence of the TaqMan probe is 5'-[FAM]-CCA GAG TCA CAC AAC AGA CGG GCA CA-[BHQ1]-3' (SEQ ID NO: 3). The nucleic acid sample and PCR reagents are loaded and partitioned within the microfluidic device following the above mentioned protocol. PCR amplification is performed by increasing the temperature of the microchambers to 95° C. and holding the temperature for 10 minutes followed by forty cycles ramping the temperature of the microchambers from 95° C. to 59° C. at a rate of 2.4° C. per second with a 1 minute hold at 59° C. prior to returning the temperature to 95° C. FIGS. 10A-10D show fluorescent images of samples containing approximately one nucleic acid template copy per partition and partitions containing zero nucleic acid template copies per partition (no template control or NTC) after PCR amplification and fluorescence intensity plots of samples containing approximately one nucleic acid copy per partition and NTC partitions after PCR amplification. FIG. 10A shows a fluorescent image of the partitioned sample containing no nucleic acid template and each grey dot represents a single microchamber containing the PCR reagents. The image is taken by exciting the ROX indicator within each microchamber with approximately 575 nm light and imaging the emission spectrum, which has a max emission at approximately 600 nm. FIG. 10B shows the partitioned sample containing approximately one nucleic acid template copy per partition after PCR amplification. After PCR amplification, imaging shows microchambers that contain the ROX indicator and microchambers that contain both the ROX indicator and emission from the FAM probe. The FAM probe has an excitation wavelength of approximately 495 nm and an emission wavelength maximum of approximately 520 nm. Individual microchambers contain the ROX indicator, the FAM probe, and the BHQ-1 quencher. As with FIG. 10A each grey dot represents a microchamber containing the partitioned sample with no nucleic acid template. The white dots represent microchambers that contain nucleic acid samples that have been successfully amplified. Upon successful PCR amplification, the FAM fluorophore and BHQ-1 quencher may be cleaved from the TaqMan probe, resulting in a detectable fluorescent signal. FIGS. 10C and 10D show a 2-dimensional scatter plot of the FAM fluorescent intensity as a function of the ROX fluorescent intensity for each microchamber for the partitioned and amplified microfluidic device, respectively. FIG. 10C shows a sample containing zero nucleic acid templates per partition, resulting in a FAM fluorescent intensity that is predominantly constant over a range of ROX fluorescent intensities. FIG. 10D shows a sample containing approximately one nucleic acid template copy per partition, resulting in a FAM fluorescent intensity that varies as a function of ROX fluorescent intensity due to the presence of amplification signals within the partition.

EXAMPLE 3 qdPCR

Figure 18:
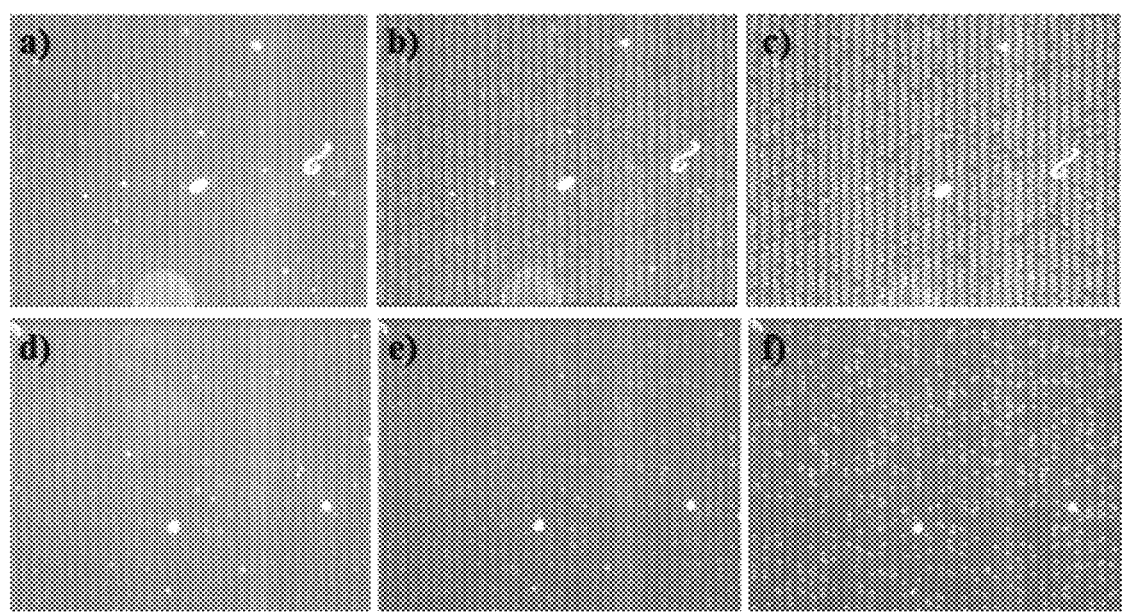
FIG. 18 shows sample images taken after amplification of a subset of partitions under different conditions in a device useful for sample processing and/or analysis.
Figure 19:
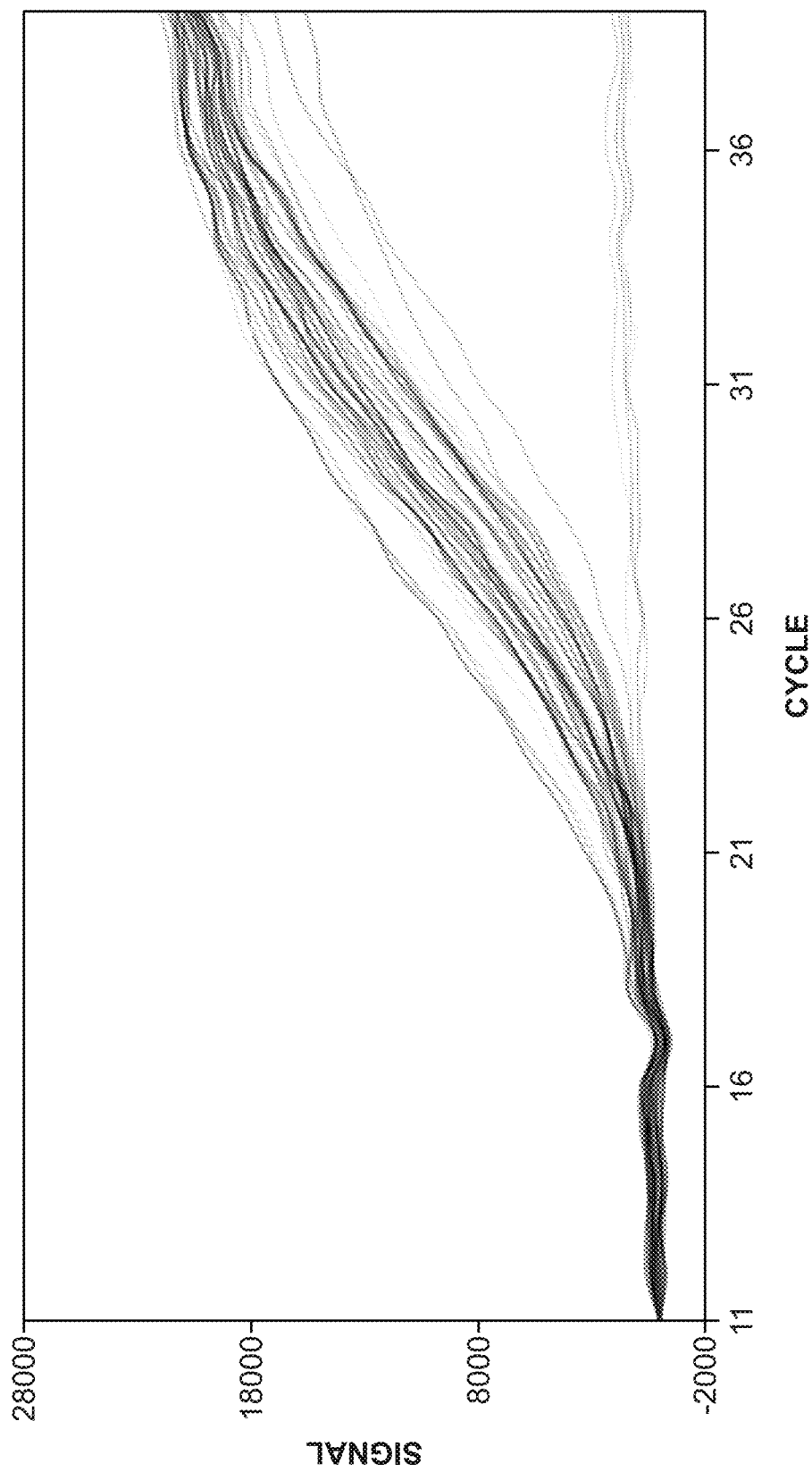
FIG. 19 shows sample qdPCR data taken using the example system of FIGS. 17A-17B and corresponding to the images of FIG. 18.

A known PCR reagent kit was used to prepare two reagent mixtures, the first with ten times the amount of target of the second. The reagents were loaded into two adjacent units of device and pneumatically prepared using an off-shelf controller and custom interface jig. The device (1708) was then removed and positioned within the system of FIGS. 17A-17B. Device 1708 was held on a standard flat-block thermal cycler 1703 by a piece of glass for good thermal contact. Device 1708 was thermal cycled 40 times using a standard 96-61° C.×40 PCR protocol. During the low temperature step (61° C.) of each cycle (cycles 11-40), an image was automatically taken using camera 1704. The images are shown in FIG. 18, in which images in the first column were taken at 20 cycles, images in the second column were taken at 30 cycles, and images in the third column were taken at 40 cycles. The top row of images corresponds to loading at a rate of 10 copies per partition, while the bottom row corresponds to 1 copy per partition. A custom ImageJ plugin was used to extract average intensity data for 53 selected points of the 10 times image set in each of the 30 cycle images. These data are plotted in FIG. 19 and are normalized for background variation.

EXAMPLE 4

HRM Analysis

Figure 25:
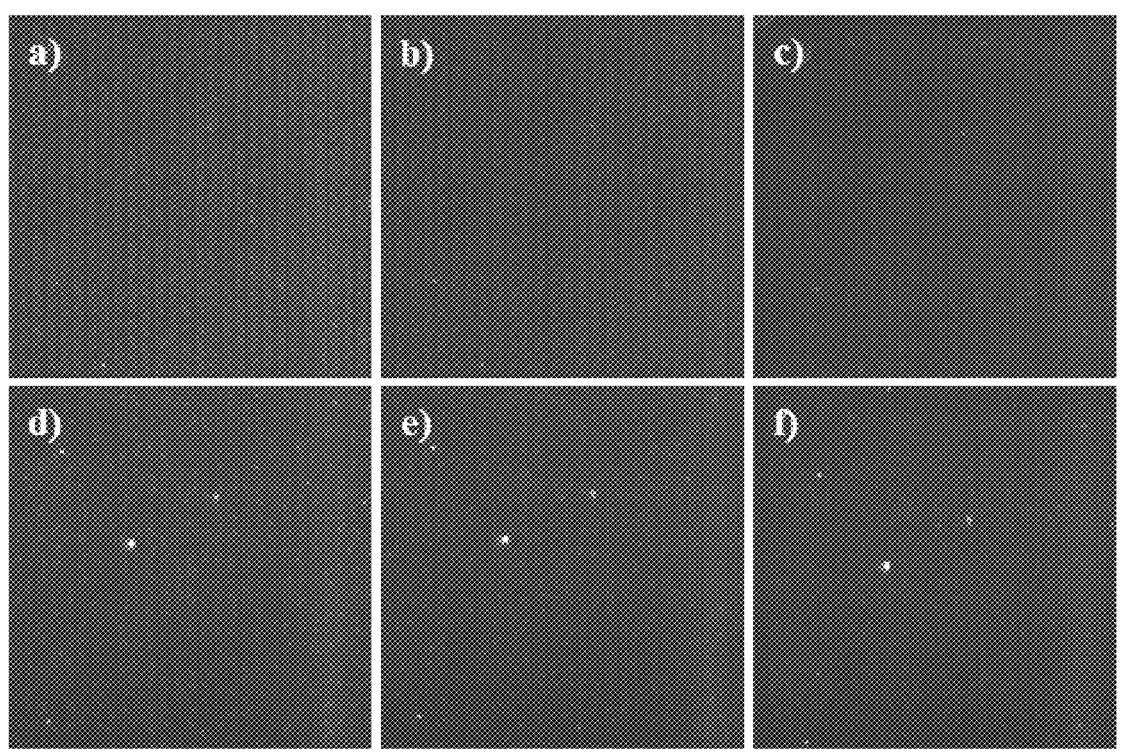
FIG. 25 shows sample images taken during an HRM analysis of a subset of partitions in a device useful for sample processing and/or analysis taken under different conditions.
Figure 26:
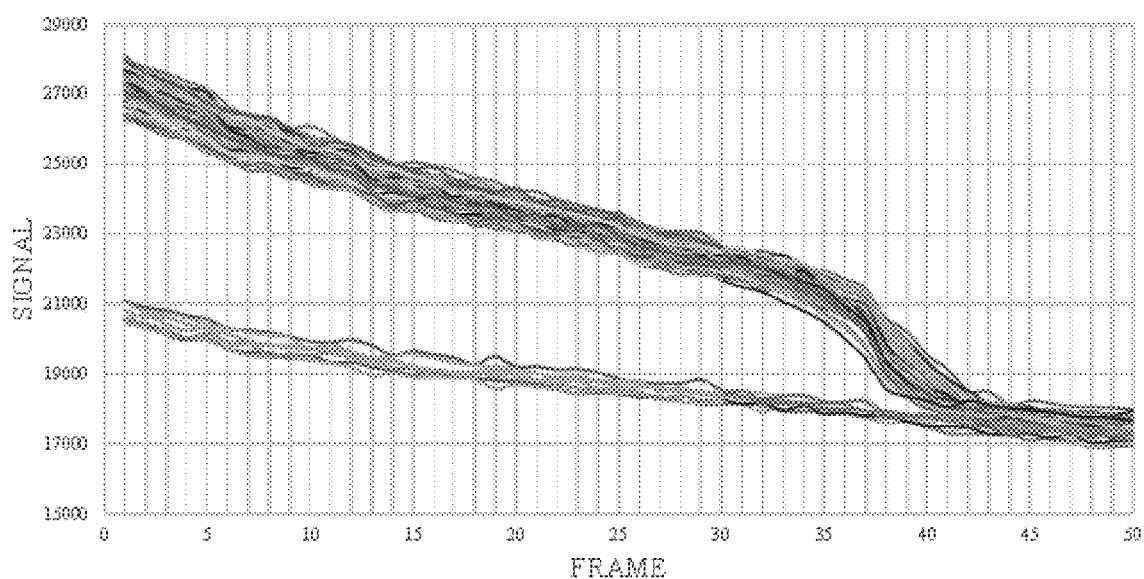
FIG. 26 shows sample HRM data corresponding to the images of FIG. 25.

A known reagent kit was used to prepare two reagent mixtures, the first with ten times the amount of target of the second. The reagents were loaded into two adjacent units of device and pneumatically prepared using an off-shelf controller and custom interface jig. The device (1708) was then removed and positioned within the system of FIGS. 17A-17B. Device 1708 was held on a standard flat-block thermal cycler 1703 by a piece of glass for good thermal contact. Device 1708 was thermal cycled 40 times using a standard 96-61° C.×40 PCR protocol to complete the dPCR step. Camera 1704 imaged the devices every 5 seconds continuously as thermal unit 1703 increased the temperature at a rate of about 0.1° C./s from about 60° C. to about 90° C. The images are shown in FIG. 25, in which images in the first column were taken at about 70° C., images in the first column were taken at about 80° C., and images in the third column were taken at about 90° C. The top row of images corresponds to loading at a rate of 10 copies per partition, while the bottom row corresponds to 1 copy per partition. A custom ImageJ plugin was used to extract average intensity data for 54 selected points in each image of the 10 times image set. These data are plotted in FIG. 26.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for analyzing a plurality of nucleic acid molecules, comprising:
   (a) providing a device comprising a plurality of partitions, wherein at least a subset of said plurality of partitions comprises said plurality of nucleic acid molecules, wherein each partition of said at least said subset of said plurality of partitions is configured to permit gas flow from said at least said subset of said plurality of partitions to an environment external to said at least said subset of said plurality of partitions through at least one thin film separating said at least said subset of said plurality of partitions from said external environment, wherein said at least one thin film is (i) substantially gas impermeable when a first pressure differential is applied across said at least one thin film and (ii) substantially gas permeable when a second pressure differential greater than said first pressure differential is applied across said at least one thin film;
   (b) using a fluid flow unit to apply a pressure differential across said at least one thin film to subject gas in said plurality of partitions to flow through said at least one thin film to said external environment;
   (c) while subjecting said at least said subset of said plurality of partitions to controlled heating, collecting signals from said at least said subset of said plurality of partitions; and
   (d) processing said signals collected in (c) to yield data indicative of at least one melting point of at least a subset of said plurality of nucleic acid molecules in said at least said subset of said plurality of partitions.

2. The method of claim 1, further comprising, prior to (a), performing nucleic acid amplification reactions on a nucleic acid sample under conditions sufficient to yield said plurality of nucleic acid molecules as amplification products of said nucleic acid sample.

3. The method of claim 2, further comprising loading said nucleic acid sample into said at least said subset of said plurality of partitions prior to performing said nucleic acid amplification reactions.

4. The method of claim 2, wherein performing nucleic acid amplification reactions on said nucleic acid sample comprises amplifying at least a portion of an internal transcribed spacer region of at least a subset of the nucleic acid molecules of said nucleic acid sample.

5. The method of claim 1, wherein (c) comprises imaging said at least said subset of said plurality of partitions to collect said signals.

6. The method of claim 1, wherein said processing in (d) comprises using said signals to generate signal versus temperature data for said at least said subset of said plurality of nucleic acid molecules in said at least said subset of said plurality of partitions.

7. The method of claim 1, wherein said plurality of nucleic acid molecules are derived from a sample containing or suspected of containing a pathogen.

8. The method of claim 7, wherein said pathogen is at least one bacterium.

9. The method of claim 8, further comprising, prior to (a), isolating or extracting said plurality of nucleic acid molecules, or a subset thereof, from said at least one bacterium.

10. The method of claim 7, further comprising using said data indicative of said melting point to determine a presence or absence of said pathogen in each partition of said at least said subset of said plurality of partitions.

11. The method of claim 1, further comprising loading said plurality of nucleic acid molecules into said plurality of partitions, wherein during said loading, gas in said at least said subset of said plurality of partitions is subjected to flow from said at least said subset of said plurality of partitions through said at least one thin film to said environment external to said at least said subset of said plurality of partitions.

12. The method of claim 1, wherein said plurality of nucleic acid molecules are derived from a blood sample.

13. The method of claim 1, further comprising using said at least one melting point to identify one or more variants within said plurality of nucleic acid molecules.

14. The method of claim 13, further comprising quantifying said one or more variants.

15. A method for analyzing a plurality of nucleic acid molecules, comprising:
(a) providing a device comprising a plurality of partitions, wherein at least a subset of said plurality of partitions comprises said plurality of nucleic acid molecules, wherein each partition of said at least said subset of said plurality of partitions is configured to permit gas flow from said at least said subset of said plurality of partitions to an environment external to said at least said subset of said plurality of partitions through at least one thin film separating said at least said subset of said plurality of partitions from said external environment, wherein said at least one thin film is (i) substantially gas impermeable when a first pressure differential is applied across said at least one thin film and (ii) substantially gas permeable when a second pressure differential greater than said first pressure differential is applied across said at least one thin film;
(b) using a fluid flow unit to apply a pressure differential across said at least one thin film to subject gas in said plurality of partitions to flow through said at least one thin film to said external environment;
(c) subjecting said at least said subset of said plurality of partitions to conditions sufficient to conduct nucleic acid amplification reactions using said plurality of nucleic acid molecules to generate amplification products from at least a subset of said plurality of nucleic acid molecules;
(d) while subjecting said at least said subset of said plurality of partitions to said conditions in (c), collecting signals from said at least said subset of said plurality of partitions over a plurality of time points; and
(e) processing said signals to determine a number of nucleic acid molecules in said at least said subset of said plurality of partitions.

16. The method of claim 15, wherein subjecting said at least said subset of said plurality of partitions to conditions sufficient to conduct nucleic acid amplification reactions in (c) comprises thermal cycling, and wherein said collecting signals in (d) comprises collecting signals from each partition of said at least said subset of said plurality of partitions more than once per thermal cycle.

17. The method of claim 15, wherein said thermal cycling is performed using a flat block thermal cycler.

18. The method of claim 15, wherein (d) comprises imaging said at least said subset of said plurality of partitions to collect said signals.

19. The method of claim 15, wherein (d) is performed using a detector that detects fluorescence emission at two or more wavelengths.

20. The method of claim 15, wherein (e) comprises determining an optical intensity for each partition of said at least said subset of said plurality of partitions, wherein said optical intensity is proportional to an amount of amplification products in each of said at least said subset of said plurality of partitions.

21. The method of claim 15, further comprising loading said plurality of nucleic acid molecules into said plurality of partitions, wherein during said loading, gas in said at least said subset of said plurality of partitions is subjected to flow from said at least said subset of said plurality of partitions through said at least one thin film to said environment external to said at least said subset of said plurality of partitions.

* * * * *